US012735475B2

(12) United States Patent
Ritter et al.

(10) Patent No.: US 12,735,475 B2
(45) Date of Patent: Sep. 15, 2026

(54) HUMANIZED AND VARIANT TGF-β3 SPECIFIC ANTIBODIES AND METHODS AND USES THEREOF

(71) Applicants: LUDWIG INSTITUTE FOR CANCER RESEARCH LTD., Zurich (CH); CENTRE HOSPITALIER UNIVERSITAIRE VAUDOIS, Lausanne (CH)

(72) Inventors: Gerd Ritter, New York, NY (US); Steven Dunn, Epalinges (CH)

(73) Assignees: LUDWIG INSTITUTE FOR CANCER RESEARCH LTD., Zurich (CH); CENTRE HOSPITALIER UNIVERSITAIRE VAUDOIS, Lausanne (CH)

( * ) Notice: Subject to any disclaimer, the term of this patent is extended or adjusted under 35 U.S.C. 154(b) by 1451 days.

(21) Appl. No.: 17/290,834

(22) PCT Filed: Nov. 4, 2019

(86) PCT No.: PCT/IB2019/001178
§ 371 (c)(1),
(2) Date: May 3, 2021

(87) PCT Pub. No.: WO2020/095104
PCT Pub. Date: May 14, 2020

(65) Prior Publication Data

US 2021/0388074 A1 Dec. 16, 2021

Related U.S. Application Data

(60) Provisional application No. 62/755,840, filed on Nov. 5, 2018.

(51) Int. Cl.
*C07K 16/22* (2006.01)
*A61K 39/395* (2006.01)

(52) U.S. Cl.
CPC .......... *C07K 16/22* (2013.01); *A61K 39/3955* (2013.01); *C07K 2317/24* (2013.01); *C07K 2317/33* (2013.01); *C07K 2317/565* (2013.01); *C07K 2317/622* (2013.01); *C07K 2317/76* (2013.01); *C07K 2317/92* (2013.01)

(58) Field of Classification Search
CPC ................ C07K 16/22; C07K 2317/24; C07K 2317/565; C07K 2317/622; C07K 2317/76; C07K 2317/92; C07K 2317/33; A61K 39/3955
USPC .......... 530/388.23, 388.24, 391.3; 424/158.1
See application file for complete search history.

(56) References Cited

FOREIGN PATENT DOCUMENTS

WO 2016/201282 * 12/2015

OTHER PUBLICATIONS

Bowers et al. (2012) J. Biol. Chem., vol. 288(11), 7688-7696.*
Kim et al. "Humanization by CDR Grafting and Specificity-Determining Residue Grafting" (2012) Patrick Chames (ed.), Antibody Engineering: Methods and Protocols, Second Edition, Methods in Molecular Biology, vol. 907, Chapter 13DOI 10. 1007/978-1-61779-974-7_13, pp. 237-245.*
Sela-Culang et al. (2013) Frontiers in Immunology, vol. 4, pp. 1-13.*
Vajdos et al. (2002) J. Mol. Biol., vol. 320, 415-428.*
Chen et al. (1992) J. Exp. Med., vol. 176, 855-866.*

* cited by examiner

*Primary Examiner* — Anne Marie S Wehbe
(74) *Attorney, Agent, or Firm* — Hoffmann & Baron LLP

(57) ABSTRACT

Antibodies, particularly humanized antibodies and variant antibodies and fragments thereof, which bind to transforming growth factor beta 3 (TGF-β3) are provided, recognizing human and mouse TGF-β3, particularly antibodies and fragments that do not recognize or bind TGF-β1 or TGF-β2. Humanized and variant antibodies are provided which specifically recognize and neutralize TGF-β3 and are useful in the diagnosis and treatment of conditions associated with activated or elevated TGF-β3, including cancer, and for modulating immune cells and immune response, including immune response to cancer or cancer antigens, and in fibrotic conditions. The anti-TGF-β3 antibodies, variable regions or CDR domain sequences thereof, and fragments thereof may also be used in lymphoid cell-mediated, including T cell-mediated, therapy and in therapy in combination with chemotherapeutics, immune modulators, or anti-cancer agents and/or with other antibodies or fragments thereof. Antibodies are exemplified by antibodies hereof, including antibodies 1901-1A, 1901-1B, 1901-1C and 1901-1D whose sequences are provided herein.

10 Claims, 29 Drawing Sheets

Specification includes a Sequence Listing.

FIG 1

>m1901_VH_genscript_DNA

*ATGGAATGGCCTTGTATCTTTCTCTTCCTCCTGTCAGTAACTGAAGGTGTCCACTCC*CAGGTTCTCCTGCAGCAGTCTGGACCTGAGCTGGTGAAGC
CTGGGGCCTCAGTGAAGATTTCCTGCAAGGCTTCTGGCTACGCATTCAGTAGCTCCTGGATACACTGGGTGAAGCAGAGGCCTGGAAA
GGGTCTTGAGTGGATTGGACGGATTTATCCGGGAGATGGAGATACTAACTATACTGGGAAGTTCAAGGGCAAGGCCACACTTACTGCA
GACAAATCCTCCAGCACAGCCTACATGCAACTCAGCAGCCTGACATCTGAGGACTCTGCGGTCTACTTCTGTGCAAGAAGGATGATTAC
GACTCAGGCGGCTATGGACTACTGGGGTCAAGGAACCTCAGTCACCGTCTCCTCA

>m1901_VH_genscript_AA

QVLLQQSGPELVKPGASVKISCKASGYAFSSSWIHWVKQRPGKGLEWIGRIYPGDGDTNYTGKFKGKATLTADKSSSTAYMQLSSLTSEDSAV
YFCARRMITTQAAMDYWGQGTSVTVSS

>m1901_VK_genscript_DNA

*ATGAAGTCACAGACCCAGGTCTTCGTATTTCTACTGCTCTGTGTGTCTGGTGCTCATGGG*AGTTTTGTGATGACCCAGACTCCCAAATTCCTGCTTGT
ATCAGCAGGAGACAGGGTTACCATAACCTGCAAGGCCAGTCAGAGTGTGATTAATGCTGTAGCTTGGTACCAACAGAAGCCAGGGCAG
TCTCCTAAACTGCTGATATACTATGCATCCAATCGCTACACTGGAGTCCCTGATCGCTTCACTGGCAATGGATATGGGACGGATTTCACTT
TCACCATCAGCACTGTGCAGGCTGAAGACCTGGCAGTTTATTTCTGTCAGCAGGATTATAGCTCTCCGTACACGTTCGGAGGGGGGACC
AAGCTGGAAATAAAA

>m1901_VK_genscript_AA

SFVMTQTPKFLLVSAGDRVTITCKASQSVINAVAWYQQKPGQSPKLLIYYASNRYTGVPDRFTGNGYGTDFTFTISTVQAEDLAVYFCQQDYSS
PYTFGGGTKLEIK

*XXXXXX* *Native signal peptides present in the Genscript sequences*

FIG 3

```
Murine_1901      --SFVMTQTPKFLLVSAGDRVTITCKASQSVINAVAWYQQKPGQSPKLLIYYASNRYTGV
1901_GLv1        --DIQMTQSPSSLSASVGDRVTITCKASQSVINAVAWYQQKPGKAPKLLIYYASNRYTGV
                   .: ***:*. * .*.**************************::***************

Murine_1901      PDRFTGNGYGTDFTFTISTVQAEDLAVYFCQQDYSSPYTFGGGTKLEIKRTVAARQEGGS
LCR1901_GLv1     PSRFSGSGSGTDFTLTISSLQPEDFATYYCQQDYSSPYTFGGGTKLEIKRTVAARQEGGS
                 *.**:*.* *****:***::* **:*.*:*********************

Murine_1901      GEGGSGESNAAAQVLLQQSGPELVKPGASVKISCKASGYAFSSSWIHWVKQRPGKGLEWI
LCR1901_GLv1     GEGGSGESNAAAQVQLVQSGAEVKKPGSSVKVSCKASGYAFSSSWIHWVRQAPGQGLEWI
                             ** * *** *: ***:***:*****************:* **:*****

Murine_1901      GRIYPGDGDTNYTGKFKGKATLTADKSSSTAYMQLSSLTSEDSAVYFCARRMITTQAAMD
LCR1901_GLv1     GRIYPGDGDTNYTGKFKGRVTITADKSTSTAYMELSSLRSEDTAVYYCARRMITTQAAMD
                 *****************:.*:*****:*****:**** ***:***:*************

Murine_1901      YWGQGTSVTVSSASTKAS
LCR1901_GLv1     YWGQGTSVTVSSASTKAS
                 ************
```

Grafting of IGKV1-39*01/IGHV1-69*08: Murine CDR cores in bold; Vernier residues are underlined; scFv linker in italics (CLUSTAL O(1.2.1) multiple sequence alignment)

Homology: ( * ) conserved sequence
( : ) conservative mutation
( . ) semi-conservative mutation
( ) non-conservative mutation

FIG 6

| LCR1901_GLv_VH Suggested correction | Final corrections in VH LCR1901 VH_1G10 | LCR1901_GLv_VK Suggested correction | Final correction in VK | Potential Liability |
|---|---|---|---|---|
| **A29>T29** | A29>T29 | K24>R24 | K24 maintained | mu/hu homology mismatch |
| **I53>M53** | I53 retained | | | mu/hu homology mismatch |
| **N66>(N/S/D)66** | N66>D66 | | | putative N-glycon motif |
| **T68> (T/A/S)68** | T68>S68 | | | putative N-glycon motif |
| **G69> (G/Q/P/R/E/A)69** | G69>E69 | | | mu/hu homology mismatch |
| **K72>Q72** | K72>Q72 | | | mu/hu homology mismatch |
| **M108> (M/L/V)108** | M108 retained | | | methionine oxidation risk |
| **M115>(M/L/V)115** | M115>L115 | | | methionine oxidation risk |

FIG 7

| | VH Protein Sequence |
|---|---|
| **Murine 1901 VH** | QVLLQQSGPELVKPGASVKISCKAS**GYAFSSSWIH**WVKQRPGKGLE**WIGRIYPGDGDTNYTGKFK**GKATLTADKSSSTAYMQLSSLTSEDSAVYFC**ARRMITTQAAM**DYWGQGTSVTVSS |
| **LCR1901_GLv1 grafted onto huIGHV1-69*08 framework^** | QVQLVQSGAEVKKPGSSVKVSCKAS**GYAFSSSWIH**WVRQAPGQGLE**WIGRIYPGDGDTNYTGKFK**GRVTITADKSTSTAYMELSSLRSEDTAVYYC**ARRMITTQAAM**DYWGQGTSVTVSS |
| **LCR1901 VH_1G10 Corrections of sequence liabilities^^** | QVQLVQSGAEVKKPGSSVKVSCKAS**GYTFSSSWIH**WVRQAPGQGLE**WIGRIYPGDGDTDYSEKFQ**GRVTITADKSTSTAYMELSSLRSEDTAVYYC**ARRMITTQAAL**DYWGQGTSVTVSS<br>* * |
| **LCR1901 VH_1G10m Corrections of sequence liabilities for IgG4^^^** | QVQLVQSGAEVKKPGSSVKVSCKAS**GYTFSSSWIH**WVRQAPGQGLE**WIGRIYPGDGDTDYSEKFQ**GRVTITADKSTSTAYMELSSLRSEDTAVYYC**ARRMITTQAAL**DYWGQGTLVTVSS<br>* * |
| **LCR1901 VH_1G10m_GLv1_03 (K) ^^^^** | QVQLVQSGAEVKKPGSSVKVSCKAS**GYTFSSSWIH**WVKQRPGKGLE**WIGRIYPGDGDTDYSEKFQ**GRVTITADKSTSTAYMELSSLRSEDTAVYYC**ARRMITTQAAL**DYWGQGTLVTVSS<br># # # * * |
| **LCR1901 VH_1G10m_02(J)** | QVQLVQSGAEVKKPGSSVKVSCKAS**GYTFSSSWIH**WVRQAPGKGLE**WIGRIYPGDGDTDYSEKFQ**GRVTITADKSTSTAYMELSSLRSEDTAVYYC**ARRMITTQAAL**DYWGQGTLVTVSS<br># * * |

X = alterations from original graft;
X* = mouse residues maintained;
# = back-mutation of human to original mouse;
IMGT numbering for amino acid residue sequence numbers CDRs (in bold) and Vernier regions grafted; parental IGHJ retained ^^ - A29>T (dominant hu CDR1 residue)
- I53 (CDR2 junction) > parental retained
- N66,T68,G69 (CDR2 N-glycon)> D66, S68, E69
- K72 (CDR2 junction) > Q72
- M108, M115 (CDR3 sulfoxide risk) > M108 (preferred), L115

^^^ - S123>L123 (correction to hu IGHJ4)

^^^^ huFR2 back mutations to mouse FR2: R43->K43; A45->R45; Q48->K48

FIG 8

| | VL (Kappa) Protein Sequence |
|---|---|
| **Murine 1901 VL** | SFVMTQTPKFLLVSAGDRVTITC**KASQSVINAVAWY**QQKPGQSPK**LLIYYASNRYT**GVPDRFTGNGYGTDFTFTISTVQAEDLAVYFC**QQDYSSPY**TFGGGTKLEIK |
| **LCR1901_GLv1 Grafted onto huIGKV1-39*01 framework^** | DIQMTQSPSSLSASVGDRVTITC**KASQSVINAVAWY**QQKPGKAPK**LLIYYASNRYT**GVPSRFSGSGSGTDFTLTISSLQPEDFATYYC**QQDYSSPY**TFGGGTKVEIK |
| **Back-mutations to original mouse sequence** | |
| **Final LCR1901 VK_GLv1_03(F)^^** | DIQMTQSPSSLSASVGDRVTITC**KASQSVINAVAWY**QQKPGQSPK**LLIYYASNRYT**GVPDRFSGSGYGTDFTFTISSLQAEDVAVYYC**QQDYSSPY**TFGGGTKVEIK<br>## # # # # # |
| **Final LCR1901 VK_GLv1_05(H)^^^** | DIQMTQSPSSLSASVGDRVTITC**KASQSVINAVAWY**QQKPGKAPK**LLIYYASNRYT**GVPDRFSGSGYGTDFTFTISSLQAEDVAVYYC**QQDYSSPY**TFGGGTKVEIK<br># # # # # |

X = alterations from original graft;
X*= mouse residues maintained;
#= back-mutation of human to original mouse IMGT numbering for amino acid residue sequence numbers
^ Parental CDRs (in bold)_/Vernier residues grafted onto IGKV1-39*01 framework regions; L124>V124 (correction to hu IGKJ4)
^^ FR2: K48>Q48; A49>S49;
FR3: S74>D74; S83>Y83; L89>F89; P96>A96; T101>V101; F99>V99 (not mouse; mouse=L)
^^^ FR3: S74>D74; S83>Y83; L89>F89; P96>A96; T101>V101; F99>V99 (not mouse; mouse=L)

FIG 9

| VH | Homology^ | VK | Homology^ |
|---|---|---|---|
| 1901 mouse-VH | ~64 (81)% | 1901 mouse_VK | ~64 (80)% |
| LCR1901_VH_GLv1 | ~86 (88)% | LCR1901_VK_GLv1 | ~85 (93)% |
| LCR1901_VH_1G10m | ~87 (91)% | LCR1901_VK_GLv1_03(F) | ~81 (87)% |
| LCR1901_VH_1G10m_03(K) | ~84 (90)% | LCR1901_VK_GLv1_05(H) | ~81 (87)% |

FIG 10

*Protein Sequences of LCR_1901_VH_1G10m – VK_GLv1_03 (F) (1901-1C)*

Heavy Chain: VH_1G10m

Signal: MDWPVHLLVLLLFWIPGAMA

VH:

QVQLVQSGAEVKKPGSSVKVSCKASGYTFSSSWIHWVRQAPGQGLEWIGRIYPGDGDTDYSEKFQGRVTITADKSTSTAYME
LSSLRSEDTAVYYCARRMITTQAALDYWGQGTLVTVSS

CDRs are in bold

CH: IgG4(S228P)

ASTKGPSVFPLAPCSRSTSESTAALGCLVKDYFPEPVTVSWNSGALTSGVHTFPAVLQSSGLYSLSSVVTVPSSSLGTKTYTCNVD
HKPSNTKVDKRVESKYGPPCPPCPAPEFLGGPSVFLFPPKPKDTLMISRTPEVTCVVVDVSQEDPEVQFNWYVDGVEVHNAKT
KPREEQFNSTYRVVSVLTVLHQDWLNGKEYKCKVSNKGLPSSIEKTISKAKGQPREPQVYTLPPSQEEMTKNQVSLTCLVKGFYP
SDIAVEWESNGQPENNYKTTPPVLDSDGSFFLYSRLTVDKSRWQEGNVFSCSVMHEALHNHYTQKSLSLSLGK

Light Chain: VK_GLv1_03 (F)

Signal: MDWPVHLLVLLLFWIPGVRA

VK:

DIQMTQSPSSLSASVGDRVTITCKASQSVINAVAWYQQKPGQSPKLLIYYASNRYTGVPDRFSGSGYGTDFTFTISSLQAEDVA
VYYCQQDYSSPYTFGGGTKVEIK

CDRs are in bold

CK: IGKC*01

RTAAAPSVFIFPPSDEQLKSGTASVVCLLNNFYPREAKVQWKVDNALQSGNSQESVTEQDSKDSTYSLSSTLTLSKADYEKHKVY
ACEVTHQGLSSPVTKSFNRGEC

FIG 11

*Protein Sequences of LCR1901_VH_1G10m – VK_GLv1_05 (H) (1901-1A)*

Heavy Chain: VH_1G10m

Signal: MDWPVHLLVLLLFWIPGAMA

VH:

QVQLVQSGAEVKKPGSSVKVSCKASGYTFSSSWIHWVRQAPGQGLEWIGRIYPGDGDTDYSEKFQGRVTITADKSTSTAYMELSSLRSEDTAVYYCARRMITTQAALDYWGQGTLVTVSS

CDRs are in bold.

CH: IgG4(S228P)

ASTKGPSVFPLAPCSRSTSESTAALGCLVKDYFPEPVTVSWNSGALTSGVHTFPAVLQSSGLYSLSSVVTVPSSSLGTKTYTCNVDHKPSNTKVDKRVESKYGPPCPPCPAPEFLGGPSVFLFPPKPKDTLMISRTPEVTCVVVDVSQEDPEVQFNWYVDGVEVHNAKTKPREEQFNSTYRVVSVLTVLHQDWLNGKEYKCKVSNKGLPSSIEKTISKAKGQPREPQVYTLPPSQEEMTKNQVSLTCLVKGFYPSDIAVEWESNGQPENNYKTTPPVLDSDGSFFLYSRLTVDKSRWQEGNVFSCSVMHEALHNHYTQKSLSLSLGK

Light Chain: VK_GLv1_05 (H)

Signal: MDWPVHLLVLLLFWIPGVRA

VK:

DIQMTQSPSSLSASVGDRVTITCKASQSVINAVAWYQQKPGKAPKLLIYYASNRYTGVPDRFSGSGYGTDFTFTISSLQAEDVAVYYCQQDYSSPYTFGGGTKVEIK

CDRs are in bold.

CK: IGKC*01

RTAAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC

FIG 12

*Protein Sequences of LCR1901_VH_1G10m_03 (K) – VK_GLv1_03 (F) (1901-1D)*

Heavy Chain: VH_1G10m_03 (K)

Signal: MDWPVHLLVLLLFWIPGAMA

VH:

QVQLVQSGAEVKKPGSSVKVSCKASGYTFSSSWIHWVKQRPGKGLEWIGRIYPGDGDTDYSEKFQGRVTITADKSTSTAYMELSSLRSEDTAVYYCARRMITTQAALDYWGQGTLVTVSS

CDRs in bold

CH: IgG4(S228P)

ASTKGPSVFPLAPCSRSTSESTAALGCLVKDYFPEPVTVSWNSGALTSGVHTFPAVLQSSGLYSLSSVVTVPSSSLGTKTYTCNVDHKPSNTKVDKRVESKYGPPCPPCPAPEFLGGPSVFLFPPKPKDTLMISRTPEVTCVVVDVSQEDPEVQFNWYVDGVEVHNAKTKPREEQFNSTYRVVSVLTVLHQDWLNGKEYKCKVSNKGLPSSIEKTISKAKGQPREPQVYTLPPSQEEMTKNQVSLTCLVKGFYPSDIAVEWESNGQPENNYKTTPPVLDSDGSFFLYSRLTVDKSRWQEGNVFSCSVMHEALHNHYTQKSLSLSLGK

Light Chain: VK_GLv1_03 (F)

Signal: MDWPVHLLVLLLFWIPGVRA

VL:

DIQMTQSPSSLSASVGDRVTITCKASQSVINAVAWYQQKPGQSPKLLIYYASNRYTGVPDRFSGSGYGTDFTFTISSLQAEDVAVYYCQQDYSSPYTFGGGTKVEIK

CDRs in bold.

CK: IGKC*01

RTAAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC

FIG 13

*Protein Sequences of LCR1901_VH_1G10m_03 (K) – VK_GLv1_05 (H) (1901-1B)*

Heavy Chain: VH_1G10m_03 (K)

Signal: MDWPVHLLVLLLFWIPGAMA

VH:

QVQLVQSGAEVKKPGSSVKVSCKASGYTFSSSWIHWVKQRPGKGLEWIGRIYPGDGDTDYSEKFQGRVTITADKSTSTAYME LSSLRSEDTAVYYCARRMITTQAALDYWGQGTLVTVSS

CDRs are in bold.

CH: IgG4(S228P)

ASTKGPSVFPLAPCSRSTSESTAALGCLVKDYFPEPVTVSWNSGALTSGVHTFPAVLQSSGLYSLSSVVTVPSSSLGTKTYTCNVD HKPSNTKVDKRVESKYGPPCPPCPAPEFLGGPSVFLFPPKPKDTLMISRTPEVTCVVVDVSQEDPEVQFNWYVDGVEVHNAKT KPREEQFNSTYRVVSVLTVLHQDWLNGKEYKCKVSNKGLPSSIEKTISKAKGQPREPQVYTLPPSQEEMTKNQVSLTCLVKGFYP SDIAVEWESNGQPENNYKTTPPVLDSDGSFFLYSRLTVDKSRWQEGNVFSCSVMHEALHNHYTQKSLSLSLGK

Light Chain: VK_GLv1_05 (H)

Signal: MDWPVHLLVLLLFWIPGVRA

VL:

DIQMTQSPSSLSASVGDRVTITCKASQSVINAVAWYQQKPGKAPKLLIYYASNRYTGVPDRFSGSGYGTDFTFTISSLQAEDVA VYYCQQDYSSPYTFGGGTKVEIK

CDRs are in bold.

CK: IGKC*01

RTAAAPSVFIFPPSDEQLKSGTASVVCLLNNFYPREAKVQWKVDNALQSGNSQESVTEQDSKDSTYSLSSTLTLSKADYEKHKVY ACEVTHQGLSSPVTKSFNRGEC

FIG 14

| | |
|---|---|
| 1901_VH_1G10m_03 (K) / 1901_VK_GLv1_03 (F) | **-41** |
| 1901_VH_1G10m / 1901_VK_GLv1_05(H) | **-41** |
| 1901_VH_Glv1 / 1901_VK_GLv1 [original graft] | **-41.4** |
| LCR1901_VH / LCR1901_VK [mouse Ab] | **-46.7** |

FIG 15
A
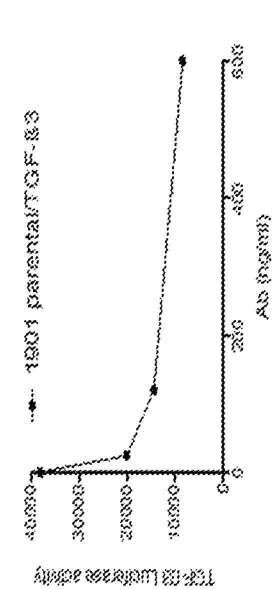
B
1901 1A/TGF-ß3
TGF-ß3 Luciferase activity
Ab (ng/ml)
C
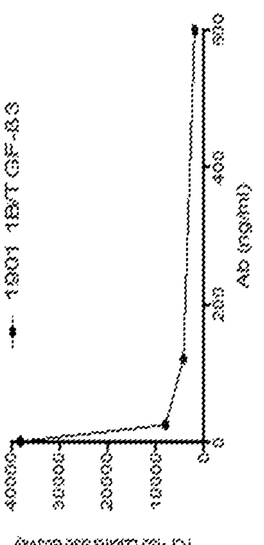
D
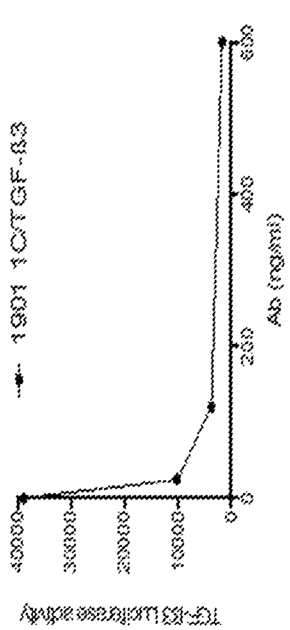
E
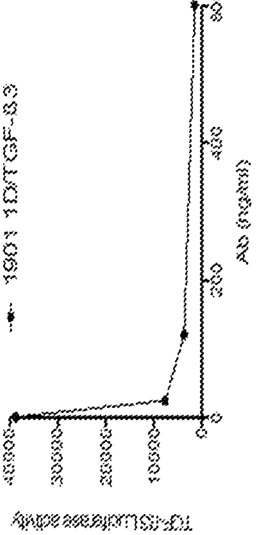

FIG 18
A
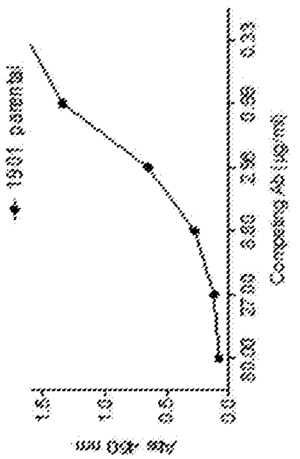
B
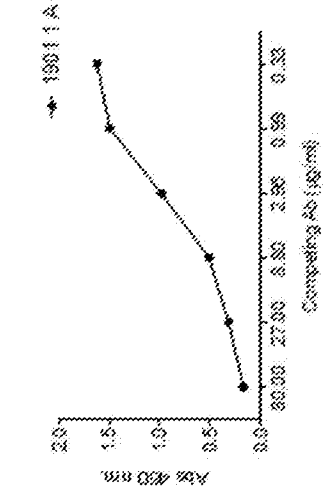
C
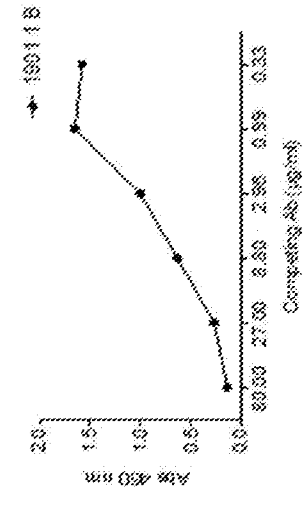
D
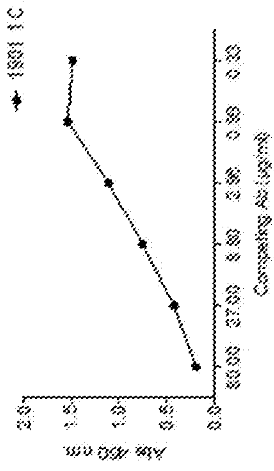
E
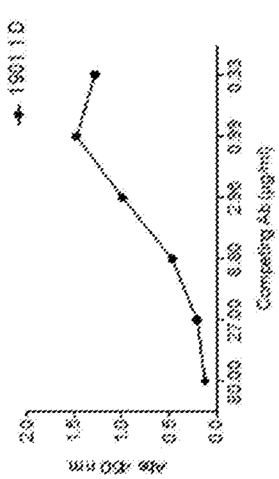

VH_1G10m - VK_GLv1_03
180618_1901_1C 001
mAU
70
60
50
40
30
20
10
0
1.79
1.57
0.19
Elution
-1
0
1
2
3
4
5
6
ml
UV
Cond
Conc B VH_1G10m_03_VK_GLv1_03
180618_1901_1D 001
mAU
45
40
35
30
25
20
15
10
5
0
1.80
1.56
0.20
Elution
-1
0
1
2
3
4
5
6
ml VH_1G10m - VK_GLv1_05
Melt Curve
Tm1
Tm2
Derivative Reporter (-Rn)
Temperature (°C)

VH_1G10m_03 - VK_GLv1_05
Melt Curve
Derivative Reporter (-Rn)
Temperature (°C)

FIG 23

| **Molecule** | *Tm1 (IgG4 CH2)* | Tm2 (Fab) |
| --- | --- | --- |
| VH_1G10m - VK_GLv1_05 | *65.9* | 84.2 |
| VH_1G10m_03 - VK_GLv1_05 | *65.9* | 82.9 |
| VH_1G10m - VK_GLv1_03 | *65.2* | 83.4 |
| VH_1G10m_03 - VK_GLv1_03 | *65.9* | 82.7 |

^ Fab transition overlapping with CH2 unfolding – no discrete Tm2

A

| Molecule | Expressed Yield (mg/L) |
|---|---|
| VH_1G10m - VK_GLv1_05 (1901_1A) | ~50-100 |
| VH_1G10m_03 - VK_GLv1_05 (1901_1B) | ~250-350 |
| VH_1G10m_VK - GLv1_03 (1901_1C) | ~250-350 |
| VH_GLv1_03_VK_GLv1_03 (1901_1D) | ~250-350 |

B

SEQUENCE LISTING

```
<160> NUMBER OF SEQ ID NOS: 55

<210> SEQ ID NO 1
<211> LENGTH: 5
<212> TYPE: PRT
<213> ORGANISM: Mus musculus

<400> SEQUENCE: 1

Ser Ser Trp Ile His
1               5


<210> SEQ ID NO 2
<211> LENGTH: 17
<212> TYPE: PRT
<213> ORGANISM: Mus musculus

<400> SEQUENCE: 2

Arg Ile Tyr Pro Gly Asp Gly Asp Thr Asn Tyr Thr Gly Lys Phe Lys
1               5                   10                  15

Gly


<210> SEQ ID NO 3
<211> LENGTH: 11
<212> TYPE: PRT
<213> ORGANISM: Mus musculus

<400> SEQUENCE: 3

Arg Met Ile Thr Thr Gln Ala Ala Met Asp Tyr
1               5                   10


<210> SEQ ID NO 4
<211> LENGTH: 11
<212> TYPE: PRT
<213> ORGANISM: Mus musculus

<400> SEQUENCE: 4

Lys Ala Ser Gln Ser Val Ile Asn Ala Val Ala
1               5                   10


<210> SEQ ID NO 5
<211> LENGTH: 7
<212> TYPE: PRT
<213> ORGANISM: Mus musculus

<400> SEQUENCE: 5

Tyr Ala Ser Asn Arg Tyr Thr
1               5


<210> SEQ ID NO 6
<211> LENGTH: 8
<212> TYPE: PRT
<213> ORGANISM: Mus musculus

<400> SEQUENCE: 6

Gln Gln Asp Tyr Ser Ser Pro Thr
1               5


<210> SEQ ID NO 7
<211> LENGTH: 112
<212> TYPE: PRT
```

<213> ORGANISM: Mus musculus

<400> SEQUENCE: 7

```
Ala Leu Asp Thr Asn Tyr Cys Phe Arg Asn Leu Glu Glu Asn Cys Cys
1               5                   10                  15

Val Arg Pro Leu Tyr Ile Asp Phe Arg Gln Asp Leu Gly Trp Lys Trp
            20                  25                  30

Val His Glu Pro Lys Gly Tyr Tyr Ala Asn Phe Cys Ser Gly Pro Cys
        35                  40                  45

Pro Tyr Leu Arg Ser Ala Asp Thr Thr His Ser Thr Val Leu Gly Leu
    50                  55                  60

Tyr Asn Thr Leu Asn Pro Glu Ala Ser Ala Ser Pro Cys Cys Val Pro
65                  70                  75                  80

Gln Asp Leu Glu Pro Leu Thr Ile Leu Tyr Tyr Val Gly Arg Thr Pro
                85                  90                  95

Lys Val Glu Gln Leu Ser Asn Met Val Val Lys Ser Cys Lys Cys Ser
            100                 105                 110
```

<210> SEQ ID NO 8
<211> LENGTH: 112
<212> TYPE: PRT
<213> ORGANISM: Homo sapiens

<400> SEQUENCE: 8

```
Ala Leu Asp Thr Asn Tyr Cys Phe Arg Asn Leu Glu Glu Asn Cys Cys
1               5                   10                  15

Val Arg Pro Leu Tyr Ile Asp Phe Arg Gln Asp Leu Gly Trp Lys Trp
            20                  25                  30

Val His Glu Pro Lys Gly Tyr Tyr Ala Asn Phe Cys Ser Gly Pro Cys
        35                  40                  45

Pro Tyr Leu Arg Ser Ala Asp Thr Thr His Ser Thr Val Leu Gly Leu
    50                  55                  60

Tyr Asn Thr Leu Asn Pro Glu Ala Ser Ala Ser Pro Cys Cys Val Pro
65                  70                  75                  80

Gln Asp Leu Glu Pro Leu Thr Ile Leu Tyr Tyr Val Gly Arg Thr Pro
                85                  90                  95

Lys Val Glu Gln Leu Ser Asn Met Val Val Lys Ser Cys Lys Cys Ser
            100                 105                 110
```

<210> SEQ ID NO 9
<211> LENGTH: 417
<212> TYPE: DNA
<213> ORGANISM: Mus musculus

<400> SEQUENCE: 9

```
atggaatggc cttgtatctt tctcttcctc ctgtcagtaa ctgaaggtgt ccactcccag     60

gttctcctgc agcagtctgg acctgagctg gtgaagcctg gggcctcagt gaagatttcc    120

tgcaaggctt ctggctacgc attcagtagc tcctggatac actgggtgaa gcagaggcct    180

ggaaagggtc ttgagtggat tggacggatt tatccgggag atggagatac taactatact    240

gggaagttca agggcaaggc cacacttact gcagacaaat cctccagcac agcctacatg    300

caactcagca gcctgacatc tgaggactct gcggtctact tctgtgcaag aaggatgatt    360

acgactcagg cggctatgga ctactggggt caaggaacct cagtcaccgt ctcctca       417
```

<210> SEQ ID NO 10
<211> LENGTH: 120

```
<212> TYPE: PRT
<213> ORGANISM: Mus musculus

<400> SEQUENCE: 10

Gln Val Leu Leu Gln Gln Ser Gly Pro Glu Leu Val Lys Pro Gly Ala
1               5                   10                  15

Ser Val Lys Ile Ser Cys Lys Ala Ser Gly Tyr Ala Phe Ser Ser Ser
            20                  25                  30

Trp Ile His Trp Val Lys Gln Arg Pro Gly Lys Gly Leu Glu Trp Ile
        35                  40                  45

Gly Arg Ile Tyr Pro Gly Asp Gly Asp Thr Asn Tyr Thr Gly Lys Phe
    50                  55                  60

Lys Gly Lys Ala Thr Leu Thr Ala Asp Lys Ser Ser Ser Thr Ala Tyr
65                  70                  75                  80

Met Gln Leu Ser Ser Leu Thr Ser Glu Asp Ser Ala Val Tyr Phe Cys
                85                  90                  95

Ala Arg Arg Met Ile Thr Thr Gln Ala Ala Met Asp Tyr Trp Gly Gln
            100                 105                 110

Gly Thr Ser Val Thr Val Ser Ser
        115                 120


<210> SEQ ID NO 11
<211> LENGTH: 381
<212> TYPE: DNA
<213> ORGANISM: Mus musculus

<400> SEQUENCE: 11

atgaagtcac agacccaggt cttcgtattt ctactgctct gtgtgtctgg tgctcatggg     60

agttttgtga tgacccagac tcccaaattc ctgcttgtat cagcaggaga cagggttacc    120

ataacctgca aggccagtca gagtgtgatt aatgctgtag cttggtacca acagaagcca    180

gggcagtctc ctaaactgct gatatactat gcatccaatc gctacactgg agtccctgat    240

cgcttcactg gcaatggata tgggacggat ttcactttca ccatcagcac tgtgcaggct    300

gaagacctgg cagtttattt ctgtcagcag gattatagct ctccgtacac gttcggaggg    360

gggaccaagc tggaaataaa a                                              381


<210> SEQ ID NO 12
<211> LENGTH: 107
<212> TYPE: PRT
<213> ORGANISM: Mus musculus

<400> SEQUENCE: 12

Ser Phe Val Met Thr Gln Thr Pro Lys Phe Leu Leu Val Ser Ala Gly
1               5                   10                  15

Asp Arg Val Thr Ile Thr Cys Lys Ala Ser Gln Ser Val Ile Asn Ala
            20                  25                  30

Val Ala Trp Tyr Gln Gln Lys Pro Gly Gln Ser Pro Lys Leu Leu Ile
        35                  40                  45

Tyr Tyr Ala Ser Asn Arg Tyr Thr Gly Val Pro Asp Arg Phe Thr Gly
    50                  55                  60

Asn Gly Tyr Gly Thr Asp Phe Thr Phe Thr Ile Ser Thr Val Gln Ala
65                  70                  75                  80

Glu Asp Leu Ala Val Tyr Phe Cys Gln Gln Asp Tyr Ser Ser Pro Tyr
                85                  90                  95

Thr Phe Gly Gly Gly Thr Lys Leu Glu Ile Lys
            100                 105
```

<210> SEQ ID NO 13
<211> LENGTH: 256
<212> TYPE: PRT
<213> ORGANISM: Artificial sequence
<220> FEATURE:
<223> OTHER INFORMATION: murine 1901 VL-VH grafted construct

<400> SEQUENCE: 13

```
Ser Phe Val Met Thr Gln Thr Pro Lys Phe Leu Leu Val Ser Ala Gly
1               5                   10                  15

Asp Arg Val Thr Ile Thr Cys Lys Ala Ser Gln Ser Val Ile Asn Ala
            20                  25                  30

Val Ala Trp Tyr Gln Gln Lys Pro Gly Gln Ser Pro Lys Leu Leu Ile
        35                  40                  45

Tyr Tyr Ala Ser Asn Arg Tyr Thr Gly Val Pro Asp Arg Phe Thr Gly
    50                  55                  60

Asn Gly Tyr Gly Thr Asp Phe Thr Phe Thr Ile Ser Thr Val Gln Ala
65                  70                  75                  80

Glu Asp Leu Ala Val Tyr Phe Cys Gln Gln Asp Tyr Ser Ser Pro Tyr
                85                  90                  95

Thr Phe Gly Gly Gly Thr Lys Leu Glu Ile Lys Arg Thr Val Ala Ala
            100                 105                 110

Arg Gln Glu Gly Gly Ser Gly Glu Gly Gly Ser Gly Glu Ser Asn Ala
        115                 120                 125

Ala Ala Gln Val Leu Leu Gln Gln Ser Gly Pro Glu Leu Val Lys Pro
    130                 135                 140

Gly Ala Ser Val Lys Ile Ser Cys Lys Ala Ser Gly Tyr Ala Phe Ser
145                 150                 155                 160

Ser Ser Trp Ile His Trp Val Lys Gln Arg Pro Gly Lys Gly Leu Glu
                165                 170                 175

Trp Ile Gly Arg Ile Tyr Pro Gly Asp Gly Asp Thr Asn Tyr Thr Gly
            180                 185                 190

Lys Phe Lys Gly Lys Ala Thr Leu Thr Ala Asp Lys Ser Ser Ser Thr
        195                 200                 205

Ala Tyr Met Gln Leu Ser Ser Leu Thr Ser Glu Asp Ser Ala Val Tyr
    210                 215                 220

Phe Cys Ala Arg Arg Met Ile Thr Thr Gln Ala Ala Met Asp Tyr Trp
225                 230                 235                 240

Gly Gln Gly Thr Ser Val Thr Val Ser Ser Ala Ser Thr Lys Ala Ser
                245                 250                 255
```

<210> SEQ ID NO 14
<211> LENGTH: 256
<212> TYPE: PRT
<213> ORGANISM: Artificial sequence
<220> FEATURE:
<223> OTHER INFORMATION: LCR1901_Glv1 VL-VH grafted construct

<400> SEQUENCE: 14

```
Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Ser Val Ile Asn Ala
            20                  25                  30

Val Ala Trp Tyr Gln Gln Lys Pro Gly Lys Ala Pro Lys Leu Leu Ile
        35                  40                  45

Tyr Tyr Ala Ser Asn Arg Tyr Thr Gly Val Pro Ser Arg Phe Ser Gly
```

```
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Asp Tyr Ser Ser Pro Tyr
                85                  90                  95

Thr Phe Gly Gly Gly Thr Lys Leu Glu Ile Lys Arg Thr Val Ala Ala
            100                 105                 110

Arg Gln Glu Gly Gly Ser Gly Glu Gly Gly Ser Gly Glu Ser Asn Ala
        115                 120                 125

Ala Ala Gln Val Gln Leu Val Gln Ser Gly Ala Glu Val Lys Lys Pro
    130                 135                 140

Gly Ser Ser Val Lys Val Ser Cys Lys Ala Ser Gly Tyr Ala Phe Ser
145                 150                 155                 160

Ser Ser Trp Ile His Trp Val Arg Gln Ala Pro Gly Gln Gly Leu Glu
                165                 170                 175

Trp Ile Gly Arg Ile Tyr Pro Gly Asp Gly Asp Thr Asn Tyr Thr Gly
            180                 185                 190

Lys Phe Lys Gly Arg Val Thr Ile Thr Ala Asp Lys Ser Thr Ser Thr
        195                 200                 205

Ala Tyr Met Glu Leu Ser Ser Leu Arg Ser Glu Asp Thr Ala Val Tyr
    210                 215                 220

Tyr Cys Ala Arg Arg Met Ile Thr Thr Gln Ala Ala Met Asp Tyr Trp
225                 230                 235                 240

Gly Gln Gly Thr Ser Val Thr Val Ser Ser Ala Ser Thr Lys Ala Ser
                245                 250                 255


<210> SEQ ID NO 15
<211> LENGTH: 120
<212> TYPE: PRT
<213> ORGANISM: Mus musculus

<400> SEQUENCE: 15

Gln Val Leu Leu Gln Gln Ser Gly Pro Glu Leu Val Lys Pro Gly Ala
1               5                   10                  15

Ser Val Lys Ile Ser Cys Lys Ala Ser Gly Tyr Ala Phe Ser Ser Ser
            20                  25                  30

Trp Ile His Trp Val Lys Gln Arg Pro Gly Lys Gly Leu Glu Trp Ile
        35                  40                  45

Gly Arg Ile Tyr Pro Gly Asp Gly Asp Thr Asn Tyr Thr Gly Lys Phe
    50                  55                  60

Lys Gly Lys Ala Thr Leu Thr Ala Asp Lys Ser Ser Ser Thr Ala Tyr
65                  70                  75                  80

Met Gln Leu Ser Ser Leu Thr Ser Glu Asp Ser Ala Val Tyr Phe Cys
                85                  90                  95

Ala Arg Arg Met Ile Thr Thr Gln Ala Ala Met Asp Tyr Trp Gly Gln
            100                 105                 110

Gly Thr Ser Val Thr Val Ser Ser
        115                 120


<210> SEQ ID NO 16
<211> LENGTH: 120
<212> TYPE: PRT
<213> ORGANISM: Artificial sequence
<220> FEATURE:
<223> OTHER INFORMATION: LCR1901_Glv1 VH

<400> SEQUENCE: 16
```

```
Gln Val Gln Leu Val Gln Ser Gly Ala Glu Val Lys Lys Pro Gly Ser
1               5                   10                  15

Ser Val Lys Val Ser Cys Lys Ala Ser Gly Tyr Ala Phe Ser Ser Ser
            20                  25                  30

Trp Ile His Trp Val Arg Gln Ala Pro Gly Gln Gly Leu Glu Trp Ile
        35                  40                  45

Gly Arg Ile Tyr Pro Gly Asp Gly Asp Thr Asn Tyr Thr Gly Lys Phe
    50                  55                  60

Lys Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Arg Met Ile Thr Thr Gln Ala Ala Met Asp Tyr Trp Gly Gln
            100                 105                 110

Gly Thr Ser Val Thr Val Ser Ser
        115                 120


<210> SEQ ID NO 17
<211> LENGTH: 120
<212> TYPE: PRT
<213> ORGANISM: Artificial sequence
<220> FEATURE:
<223> OTHER INFORMATION: LCR1901_VH_1G10

<400> SEQUENCE: 17

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Ser Ser Ser
            20                  25                  30

Trp Ile His Trp Val Arg Gln Ala Pro Gly Gln Gly Leu Glu Trp Ile
        35                  40                  45

Gly Arg Ile Tyr Pro Gly Asp Gly Asp Thr Asp Tyr Ser Glu Lys Phe
    50                  55                  60

Gln Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Arg Met Ile Thr Thr Gln Ala Ala Leu Asp Tyr Trp Gly Gln
            100                 105                 110

Gly Thr Ser Val Thr Val Ser Ser
        115                 120


<210> SEQ ID NO 18
<211> LENGTH: 120
<212> TYPE: PRT
<213> ORGANISM: Artificial sequence
<220> FEATURE:
<223> OTHER INFORMATION: LCR1901_VH_1G10m

<400> SEQUENCE: 18

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Ser Ser Ser
            20                  25                  30

Trp Ile His Trp Val Arg Gln Ala Pro Gly Gln Gly Leu Glu Trp Ile
        35                  40                  45

Gly Arg Ile Tyr Pro Gly Asp Gly Asp Thr Asp Tyr Ser Glu Lys Phe
```

```
    50                  55                  60

Gln Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Arg Met Ile Thr Thr Gln Ala Ala Leu Asp Tyr Trp Gly Gln
            100                 105                 110

Gly Thr Leu Val Thr Val Ser Ser
        115                 120


<210> SEQ ID NO 19
<211> LENGTH: 120
<212> TYPE: PRT
<213> ORGANISM: Artificial sequence
<220> FEATURE:
<223> OTHER INFORMATION: LCR1901_VH_1G10m_Glv1_03(K)

<400> SEQUENCE: 19

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Ser Ser Ser
            20                  25                  30

Trp Ile His Trp Val Lys Gln Arg Pro Gly Lys Gly Leu Glu Trp Ile
        35                  40                  45

Gly Arg Ile Tyr Pro Gly Asp Gly Asp Thr Asp Tyr Ser Glu Lys Phe
    50                  55                  60

Gln Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Arg Met Ile Thr Thr Gln Ala Ala Leu Asp Tyr Trp Gly Gln
            100                 105                 110

Gly Thr Leu Val Thr Val Ser Ser
        115                 120


<210> SEQ ID NO 20
<211> LENGTH: 107
<212> TYPE: PRT
<213> ORGANISM: Mus musculus

<400> SEQUENCE: 20

Ser Phe Val Met Thr Gln Thr Pro Lys Phe Leu Leu Val Ser Ala Gly
1               5                   10                  15

Asp Arg Val Thr Ile Thr Cys Lys Ala Ser Gln Ser Val Ile Asn Ala
            20                  25                  30

Val Ala Trp Tyr Gln Gln Lys Pro Gly Gln Ser Pro Lys Leu Leu Ile
        35                  40                  45

Tyr Tyr Ala Ser Asn Arg Tyr Thr Gly Val Pro Asp Arg Phe Thr Gly
    50                  55                  60

Asn Gly Tyr Gly Thr Asp Phe Thr Phe Thr Ile Ser Thr Val Gln Ala
65                  70                  75                  80

Glu Asp Leu Ala Val Tyr Phe Cys Gln Gln Asp Tyr Ser Ser Pro Tyr
                85                  90                  95

Thr Phe Gly Gly Gly Thr Lys Leu Glu Ile Lys
            100                 105


<210> SEQ ID NO 21
```

<211> LENGTH: 107
<212> TYPE: PRT
<213> ORGANISM: Artificial sequence
<220> FEATURE:
<223> OTHER INFORMATION: LCR1901_Glv1

<400> SEQUENCE: 21

```
Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Ser Val Ile Asn Ala
            20                  25                  30

Val Ala Trp Tyr Gln Gln Lys Pro Gly Lys Ala Pro Lys Leu Leu Ile
        35                  40                  45

Tyr Tyr Ala Ser Asn Arg Tyr Thr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Asp Tyr Ser Ser Pro Tyr
                85                  90                  95

Thr Phe Gly Gly Gly Thr Lys Val Glu Ile Lys
            100                 105
```

<210> SEQ ID NO 22
<211> LENGTH: 107
<212> TYPE: PRT
<213> ORGANISM: Artificial sequence
<220> FEATURE:
<223> OTHER INFORMATION: LCR1901_VK_Glv1_03(F)

<400> SEQUENCE: 22

```
Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Ser Val Ile Asn Ala
            20                  25                  30

Val Ala Trp Tyr Gln Gln Lys Pro Gly Gln Ser Pro Lys Leu Leu Ile
        35                  40                  45

Tyr Tyr Ala Ser Asn Arg Tyr Thr Gly Val Pro Asp Arg Phe Ser Gly
    50                  55                  60

Ser Gly Tyr Gly Thr Asp Phe Thr Phe Thr Ile Ser Ser Leu Gln Ala
65                  70                  75                  80

Glu Asp Val Ala Val Tyr Tyr Cys Gln Gln Asp Tyr Ser Ser Pro Tyr
                85                  90                  95

Thr Phe Gly Gly Gly Thr Lys Val Glu Ile Lys
            100                 105
```

<210> SEQ ID NO 23
<211> LENGTH: 107
<212> TYPE: PRT
<213> ORGANISM: Artificial sequence
<220> FEATURE:
<223> OTHER INFORMATION: LCR1901_VK_Glv1_05(H)

<400> SEQUENCE: 23

```
Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Ser Val Ile Asn Ala
            20                  25                  30

Val Ala Trp Tyr Gln Gln Lys Pro Gly Lys Ala Pro Lys Leu Leu Ile
        35                  40                  45
```

```
Tyr Tyr Ala Ser Asn Arg Tyr Thr Gly Val Pro Asp Arg Phe Ser Gly
    50                  55                  60

Ser Gly Tyr Gly Thr Asp Phe Thr Phe Thr Ile Ser Ser Leu Gln Ala
65                  70                  75                  80

Glu Asp Val Ala Val Tyr Tyr Cys Gln Gln Asp Tyr Ser Ser Pro Tyr
                85                  90                  95

Thr Phe Gly Gly Gly Thr Lys Val Glu Ile Lys
            100                 105


<210> SEQ ID NO 24
<211> LENGTH: 327
<212> TYPE: PRT
<213> ORGANISM: Artificial sequence
<220> FEATURE:
<223> OTHER INFORMATION: CH IgG4(S228P)

<400> SEQUENCE: 24

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Pro Cys Pro Ala Pro
            100                 105                 110

Glu Phe Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
    130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
    210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser
    290                 295                 300
```

```
Cys Ser Val Met His Glu Ala Leu His Asn His Tyr Thr Gln Lys Ser
305                 310                 315                 320

Leu Ser Leu Ser Leu Gly Lys
                325


<210> SEQ ID NO 25
<211> LENGTH: 107
<212> TYPE: PRT
<213> ORGANISM: Artificial sequence
<220> FEATURE:
<223> OTHER INFORMATION: CK  IGKC*01

<400> SEQUENCE: 25

Arg Thr Ala Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105


<210> SEQ ID NO 26
<211> LENGTH: 6
<212> TYPE: PRT
<213> ORGANISM: Mus musculus

<400> SEQUENCE: 26

Ser Ser Ser Trp Ile His
1               5


<210> SEQ ID NO 27
<211> LENGTH: 16
<212> TYPE: PRT
<213> ORGANISM: Mus musculus

<400> SEQUENCE: 27

Arg Ile Tyr Pro Gly Asp Gly Asp Thr Asn Tyr Thr Gly Lys Phe Lys
1               5                   10                  15


<210> SEQ ID NO 28
<211> LENGTH: 10
<212> TYPE: PRT
<213> ORGANISM: Artificial sequence
<220> FEATURE:
<223> OTHER INFORMATION: VH CDR1 humanized antibody

<400> SEQUENCE: 28

Gly Tyr Thr Phe Ser Ser Ser Trp Ile His
1               5                   10


<210> SEQ ID NO 29
<211> LENGTH: 19
<212> TYPE: PRT
<213> ORGANISM: Artificial sequence
<220> FEATURE:
<223> OTHER INFORMATION: VH CDR2 humanized
```

<400> SEQUENCE: 29

Trp Ile Gly Arg Ile Tyr Pro Gly Asp Gly Asp Thr Asp Tyr Ser Glu
1 5 10 15

Lys Phe Gln

<210> SEQ ID NO 30
<211> LENGTH: 11
<212> TYPE: PRT
<213> ORGANISM: Artificial sequence
<220> FEATURE:
<223> OTHER INFORMATION: VH CDR3 humanized

<400> SEQUENCE: 30

Ala Arg Arg Met Ile Thr Thr Gln Ala Ala Leu
1 5 10

<210> SEQ ID NO 31
<211> LENGTH: 13
<212> TYPE: PRT
<213> ORGANISM: Artificial sequence
<220> FEATURE:
<223> OTHER INFORMATION: VL CDR1 humanized

<400> SEQUENCE: 31

Lys Ala Ser Gln Ser Val Ile Asn Ala Val Ala Trp Tyr
1 5 10

<210> SEQ ID NO 32
<211> LENGTH: 11
<212> TYPE: PRT
<213> ORGANISM: Artificial sequence
<220> FEATURE:
<223> OTHER INFORMATION: VL CDR2 humanized

<400> SEQUENCE: 32

Leu Leu Ile Tyr Tyr Ala Ser Asn Arg Tyr Thr
1 5 10

<210> SEQ ID NO 33
<211> LENGTH: 8
<212> TYPE: PRT
<213> ORGANISM: Artificial sequence
<220> FEATURE:
<223> OTHER INFORMATION: VL CDR3 humanized

<400> SEQUENCE: 33

Gln Gln Asp Tyr Ser Ser Pro Tyr
1 5

<210> SEQ ID NO 34
<211> LENGTH: 16
<212> TYPE: PRT
<213> ORGANISM: Artificial sequence
<220> FEATURE:
<223> OTHER INFORMATION: VH CDR2 variant humanized

<400> SEQUENCE: 34

Arg Ile Tyr Pro Gly Asp Gly Asp Thr Asp Tyr Ser Glu Lys Phe Gln
1 5 10 15

<210> SEQ ID NO 35
<211> LENGTH: 11
<212> TYPE: PRT
<213> ORGANISM: Artificial sequence
<220> FEATURE:

```
<223> OTHER INFORMATION: VH CDR3 variant humanized

<400> SEQUENCE: 35

Arg Met Ile Thr Thr Gln Ala Ala Leu Asp Tyr
1               5                   10


<210> SEQ ID NO 36
<211> LENGTH: 120
<212> TYPE: PRT
<213> ORGANISM: Artificial sequence
<220> FEATURE:
<223> OTHER INFORMATION: VH LCR1901_VH_1G10m_02(J)

<400> SEQUENCE: 36

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Ser Ser Ser
            20                  25                  30

Trp Ile His Trp Val Arg Gln Ala Pro Gly Lys Gly Leu Glu Trp Ile
        35                  40                  45

Gly Arg Ile Tyr Pro Gly Asp Gly Asp Thr Asp Tyr Ser Glu Lys Phe
    50                  55                  60

Gln Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Arg Met Ile Thr Thr Gln Ala Ala Leu Asp Tyr Trp Gly Gln
            100                 105                 110

Gly Thr Leu Val Thr Val Ser Ser
        115                 120


<210> SEQ ID NO 37
<211> LENGTH: 9
<212> TYPE: PRT
<213> ORGANISM: Artificial Sequence
<220> FEATURE:
<223> OTHER INFORMATION: VH CDR3 humanized

<400> SEQUENCE: 37

Arg Met Ile Thr Thr Gln Ala Ala Leu
1               5


<210> SEQ ID NO 38
<211> LENGTH: 25
<212> TYPE: DNA
<213> ORGANISM: Artificial Sequence
<220> FEATURE:
<223> OTHER INFORMATION: primer

<400> SEQUENCE: 38

ctgaaaggaa ggatatagaa tgtgc                                          25


<210> SEQ ID NO 39
<211> LENGTH: 20
<212> TYPE: DNA
<213> ORGANISM: Artificial Sequence
<220> FEATURE:
<223> OTHER INFORMATION: Primer

<400> SEQUENCE: 39

gtcgtctttc cagacgttag                                                20
```

<210> SEQ ID NO 40
<211> LENGTH: 33
<212> TYPE: DNA
<213> ORGANISM: Artificial Sequence
<220> FEATURE:
<223> OTHER INFORMATION: Primer

<400> SEQUENCE: 40
gagggtggtt ctggcgagtc caatgcsgcs gca 33

<210> SEQ ID NO 41
<211> LENGTH: 33
<212> TYPE: DNA
<213> ORGANISM: Artificial Sequence
<220> FEATURE:
<223> OTHER INFORMATION: Primer

<400> SEQUENCE: 41
gagggtggtt ctggcgagtc caatgccryg gca 33

<210> SEQ ID NO 42
<211> LENGTH: 33
<212> TYPE: DNA
<213> ORGANISM: Artificial Sequence
<220> FEATURE:
<223> OTHER INFORMATION: Primer

<400> SEQUENCE: 42
gagggtggtt ctggcgagtc caatgccatg gca 33

<210> SEQ ID NO 43
<211> LENGTH: 43
<212> TYPE: DNA
<213> ORGANISM: Artificial Sequence
<220> FEATURE:
<223> OTHER INFORMATION: Primer

<400> SEQUENCE: 43
atggaccctt ggtcgacgct gaggagacgg tgaccagggt tcc 43

<210> SEQ ID NO 44
<211> LENGTH: 43
<212> TYPE: DNA
<213> ORGANISM: Artificial Sequence
<220> FEATURE:
<223> OTHER INFORMATION: Primer

<400> SEQUENCE: 44
atggaccctt ggtcgacgct gaggagacgg tgaccgtggt ccc 43

<210> SEQ ID NO 45
<211> LENGTH: 43
<212> TYPE: DNA
<213> ORGANISM: Artificial Sequence
<220> FEATURE:
<223> OTHER INFORMATION: Primer

<400> SEQUENCE: 45
atggaccctt ggtcgacgct gaggagacrg tgaccagggt scc 43

<210> SEQ ID NO 46
<211> LENGTH: 43
<212> TYPE: DNA
<213> ORGANISM: Artificial Sequence
<220> FEATURE:
<223> OTHER INFORMATION: Primer

<400> SEQUENCE: 46
atggaccctt ggtcgacgct gaagagacgg tgaccattgt ccc 43

<210> SEQ ID NO 47
<211> LENGTH: 33
<212> TYPE: DNA
<213> ORGANISM: Artificial Sequence
<220> FEATURE:
<223> OTHER INFORMATION: Primer

<400> SEQUENCE: 47
ctggctcttg gcgcggctag ccctgcsats gct 33

<210> SEQ ID NO 48
<211> LENGTH: 33
<212> TYPE: DNA
<213> ORGANISM: Artificial Sequence
<220> FEATURE:
<223> OTHER INFORMATION: Primer

<400> SEQUENCE: 48
ctggctcttg gcgcggctag ccctgcgmkc gct 33

<210> SEQ ID NO 49
<211> LENGTH: 33
<212> TYPE: DNA
<213> ORGANISM: Artificial Sequence
<220> FEATURE:
<223> OTHER INFORMATION: Primer

<400> SEQUENCE: 49
ctggctcttg gcgcggctag ccctgtgcgc gct 33

<210> SEQ ID NO 50
<211> LENGTH: 44
<212> TYPE: DNA
<213> ORGANISM: Artificial Sequence
<220> FEATURE:
<223> OTHER INFORMATION: Primer

<400> SEQUENCE: 50
accaccagat ggtgcggccg cagttcgttt gatytccacc ttgg 44

<210> SEQ ID NO 51
<211> LENGTH: 44
<212> TYPE: DNA
<213> ORGANISM: Artificial Sequence
<220> FEATURE:
<223> OTHER INFORMATION: Primer

<400> SEQUENCE: 51
accaccagat ggtgcggccg cagttcgttt gatctccagc ttgg 44

<210> SEQ ID NO 52
<211> LENGTH: 44
<212> TYPE: DNA
<213> ORGANISM: Artificial Sequence
<220> FEATURE:
<223> OTHER INFORMATION: Primer

<400> SEQUENCE: 52
accaccagat ggtgcggccg cagttcgttt gatatccact ttgg 44

<210> SEQ ID NO 53
<211> LENGTH: 44

-continued

```
<212> TYPE: DNA
<213> ORGANISM: Artificial Sequence
<220> FEATURE:
<223> OTHER INFORMATION: Primer

<400> SEQUENCE: 53

accaccagat ggtgcggccg cagttcgttt aatctccagt cgtg                      44


<210> SEQ ID NO 54
<211> LENGTH: 21
<212> TYPE: DNA
<213> ORGANISM: Artificial Sequence
<220> FEATURE:
<223> OTHER INFORMATION: Primer

<400> SEQUENCE: 54

gaggatttga tattcacctg g                                               21


<210> SEQ ID NO 55
<211> LENGTH: 24
<212> TYPE: DNA
<213> ORGANISM: Artificial Sequence
<220> FEATURE:
<223> OTHER INFORMATION: Primer

<400> SEQUENCE: 55

gaattcgatc aggactgaac agag                                            24
```

HUMANIZED AND VARIANT TGF-β3 SPECIFIC ANTIBODIES AND METHODS AND USES THEREOF

CROSS REFERENCE TO RELATED APPLICATIONS

The present application is a national stage application which claims priority from PCT Application No. PCT/IB2019/001178 filed Nov. 4, 2019, which in turn, claims priority from U.S. Provisional Application Ser. No. 62/755,840 filed Nov. 5, 2018. Applicant claims the benefits of 35 U.S.C. § 120 as to the PCT application and priority under 35 U.S.C. § 119 as to the said U.S. Provisional application, and the entire disclosures of all applications are incorporated herein by reference in their entireties.

FIELD OF THE INVENTION

The present invention relates to specific binding members, particularly antibodies, particularly humanized antibodies and variant antibodies and fragments thereof, which bind to transforming growth factor beta 3 (TGF-β3), particularly recognizing human and mouse TGF-β3 and not recognizing or binding TGF-β1 or TGF-β2. The humanized and variant antibodies are useful in the diagnosis and treatment of conditions associated with activated or elevated TGF-β3, including cancer, and for modulating immune cells and immune response, including immune response to cancer or cancer antigens. The antibodies, variable regions or CDR domain sequences thereof, and fragments thereof may also be used in lymphoid cell-mediated, including T cell-mediated, therapy and in therapy in combination with chemotherapeutics, radiation therapy, immune modulators, cancer vaccines, cancer antigens, or anti-cancer agents and/or with other antibodies or fragments.

BACKGROUND OF THE INVENTION

The transforming growth factor beta (TGF-β) family forms a group of three isoforms, TGF-β1, TGF-β2, and TGF-β3, with their structure formed by interrelated dimeric polypeptide chains. Pleiotropic and redundant functions of the TGF-β family relate to control of numerous aspects and effects of cell functions in all tissues of the human body, including aspects of proliferation, differentiation, and migration (Poniatowski L A, et al, 2015, Mediators Inflamm, 2015; 137823). Although the isoforms are similar in sequence (TGF-ß3 active domain shares 86% similarity with TGF-ß1 and 91% with TGF-ß2), protein crystal structure and NMR studies have shown that TGF-ß3 active domain structure is different from TGF-ß1. Comparison of the TGF-ß3 with the structure of TGF-ß2 (Schlunegger M P, Grater M G, 1992, Nature 358:430-434; Daopin S, Piez K A, Ogawa Y, Davies D R, 1992, Science 257:369-373) reveals a virtually identical central core. Differences exist in the conformations of the N-terminal alpha-helix and in the beta-sheet loops (Mittl P R1, Priestle J P, Cox D A, McMaster G, Cerletti N, Grater M G, 1996, Protein Science July 5 (7): 1261-1271).

In most cells, three types of cell surface proteins mediate TGF-β signaling: TGF-β receptor I (TβRI), II (TβRII) and III (TβRIII) (Cheifetz S, Like B, Massagué J, J Biol Chem. 1986 Jul. 25; 261(21):9972-8). Bioactive forms of TGF-βs are dimers held together by hydrophobic interactions and, in most cases, by an intersubunit disulfide bond as well. The dimeric structure of these ligands suggests that they function by bringing together pairs of type I and II receptors, forming heterotetrameric receptor complexes (Sun P D, Davies D R, Annu Rev Biophys Biomol Struct. 1995; 24:269-91). Binding of TGF-β to extracellular domains of both receptors also induces proper conformation of the intracellular kinase domains. These receptors are subject to reversible post-translational modifications (phosphorylation, ubiquitylation and sumoylation) that regulate stability and availability of receptors as well as SMAD and non-SMAD pathway activation.

Receptor phosphorylation activates the TGF-β signaling pathway the ligand binds to TβRII first, followed by subsequent phosphorylation of a Gly-Ser regulatory region (GS-domain) within TβRI. This leads to incorporation of TβRI and formation of a large ligand-receptor complex that consists of dimeric TGF-β ligand and two pairs of TβRI and TβRII (Shi Y, Massagué J, Cell. 2003 Jun. 13; 113(6):685-700). TGF-β1 and TGF-β3 bind to TβRII without participation of type I receptor, whereas TGF-β2 interacts only with combination of both receptors (Derynck R, Feng X H, Biochim Biophys Acta. 1997 Oct. 24; 1333(2):F105-50). It has been observed that different ligand/receptor engagements of the TGF-β family may contribute to qualitative and quantitative differences in signaling events and biological outcomes (Hart P J et al Nat Struct Biol 2002 9(3):203-208). Furthermore, temporal-spatial expression of some of the TGF-β isoforms in embryogenesis is very different, indicating uncompensated, non-overlapping functions throughout development (Akhurst R J et al Development 1990 110(2): 445-460).

Expression of transforming growth factor β (TGF-β) is frequently associated with tumor metastasis and poor prognosis in animal models of cancer and cancer patients (Donkor M K et al., 2012, OncoImmunology, 1(2):162-171). Members of the TGF-β family are potent regulatory cytokines that affect multiple cell types of the immune system mediating pro-inflammatory or anti-inflammatory responses. The effect of TGF-β on T-cells is highly versatile. In concert with other soluble factors, it controls the maturation, differentiation and activity of various T cell subsets that either prevent or actuate infections, graft-versus-host reactions, immune diseases, and cancer formation (Schon H T et al., 2014, Hepatobiliary Surg Nutr, 2014, Dec. 3(6): 386-406). Several studies indicate that TGF-β can promote cancer growth and metastasis through effects on the tumor microenvironment, by promoting tumor cell invasion and by inhibiting the function of immune cells (Flavell et a, 2010, Nat Rev Imm August; 10(8): 554-67).

Studies have demonstrated that blockade of TGF-β, using mouse TGF-β generic antibody 1D11 (which recognizes TGF-β1, TGF-β2 and TGF-β3), synergistically enhances tumor vaccines in animal models via $CD8^+$ T cells (Terabe M et al (2009) Clin Cancer Res 15:6560-6569; Takaku S et al (2010) Int J Cancer 126(7):1666). Also, TGFβ production by tumor cells, myeloid-derived suppressor cells (MDSC) and stromal cells, such as cancer associated fibroblasts (CAFs), present at tumor sites along with TGFβ immune suppressive activity at the tumor site implicates blocking TGFβ to enhance antigen uptake, presentation, and activation of antitumor immune response mediated by therapeutic vaccines. TGF-β has also been indicated in driving the appearance of immunosuppressive plasma cells in various tumor types, for example hepatocellular carcinoma (Shalapour et al Nature. 2017 Nov. 16; 551(7680):340-345, Shalapour et al. Nature. 2015 May 7; 521(7550):94-8). Combining an anti TGF-β blockade with programmed cell death protein 1 (PD1) blockade have shown induction of anti tumor immunity and tumor regression in different tumor models (Mariathasan et al., Nature. 2018 Feb. 22; 554 (7693):544-548. Tauriello et al. Nature. 2018 Feb. 22; 554 (7693):538-543).

TGF-β ligands have been shown to be upregulated in many fibrotic conditions and many of the TGF-β ligands are potent drivers of extracellular matrix formation which is a hallmark of fibrotic conditions (Biernacka et al. Growth Factors. 2011 October; 29(5): 196-202). This also includes many types of cancers where fibrotic conditions have been indicated in tumor growth and spreading of metastasis (Principe et al. Cancer Res. 2016 May 1; 76(9):2525-39. Caja et al. Int J Mol Sci. 2018 Apr. 26; 19(5)). Therefore anti TGF-β targeting has been proposed and are currently being tested as treatment for various fibrotic conditions (Walton et al. Front Pharmacol. 2017 Jul. 14; 8:461), including kidney, lung, cardiac and skin. Other diseases where TGF-β has been implicated are, among others, allergic diseases (Tirado-Rodriguez et al. J Immunol Res. 2014; 2014:318481) and Fanconi Anemia (Tummala and Dokal, Cell Stem Cell. 2016 May 5; 18(5):567-8).

Several publications show differences in expression of TGF-ß isoforms in various tissues, diseases, tumors and tumor microenvironments. For example Van Belle et al showed that TGF-ß1 is expressed by some melanocytes and almost uniformly by nevi and melanomas while TGF-ß2 and TGF-ß3 were not detected in normal melanocytes but were found in nevi and in all forms of melanomas (early and advanced primary and metastatic melanomas) in a tumor progression related manner (P. Van Belle 1996 American J. of Pathology 148(6):1887-1894). There are many other examples of where variant expression of the isoforms have been shown, among other, in glioblastoma, breast cancer, wound healing and fibrosis (Roy et al. Int J Mol Sci. 2018 Apr. 8; 19(4), Hachim et al., Tumour Biol. 2018 January; 40(1), Lichtman et al., Wound Repair Regen. 2016 March; 24(2):215-22).

Also, TGF-ß3 but not TGF-ß1 immunostaining was reported to correlate in breast carcinomas with poor survival prognosis, and when combined with lymph node involvement, TGF-ß3 was a highly significant prognostic factor for survival (Ghellal A1 2000 Anticancer Res 20: 4413). Moreover, plasma levels of TGF-ß3 and complexes of TGF-ß3 and its receptor CD105 (TGF-ß3-CD105) were significantly elevated in breast cancer patients with positive lymph nodes compared to those without node metastasis, and their levels correlated with lymph node status (Li C1 1998 Int. J. Cancer 79:455). In glioma models TGF-β3 has been proposed as a gatekeeper controlling downstream signalling and have therefore been proposed as a target in glioma (Mol Cancer Ther. 2017 June; 16(6):1177-1186).

Particularly, studies have demonstrated TGF-ß3's involvement in the following: contributing to epithelial mesenchymal transition (EMT); elevated TGF-ß3 levels in breast cancer and prostate metastasis; and elevated levels of TGF-ß3 detected in late stage tumors and aggressive tumors such as breast, prostate, and lung.

Thus, it is apparent that, by targeting specific isoforms of TGF-ß, one could avoid damaging inflammatory consequences of blocking all isoforms of TGF-ß. Moreover, the differential expression patterns of TGF-ß isoforms in different cancer types gives researchers a unique opportunity to target cancer cells more specifically and with greater efficacy. There is an unmet need in the field to generate therapeutic TGF-ß antibodies against its isoforms, including particularly against TGF-ß3. In addition, the tools developed for recognizing different TGF-ß isoforms are powerful diagnostic and prognostic sources. Further, targeted TGF-β therapy is in need of available, effective and neutralizing humanized antibodies directed against specific TGF-β isoforms, particularly TGF-β3, to provide a clinically applicable therapeutic which reduces immunogenicity and patient immune response while having stability and longevity in a human. The present invention addresses such unmet needs in the field and particularly with regard to TGF-β3.

The citation of references herein shall not be construed as an admission that such is prior art to the present invention.

SUMMARY OF THE INVENTION

In a general aspect, the present invention provides novel transforming growth factor beta TGF-β antibodies directed against human TGF-β3, particularly humanized antibodies. In an aspect, the TGF-β3 antibodies of the invention are more specific for TGF-β3 binding than their binding to TGF-β1 or to TGF-β2. In an aspect, the TGF-β3 antibodies of the invention do not cross react or bind to other members of the TGF-beta family, and particularly do not cross react or bind to TGF-β1 or to TGF-β2. In an aspect, the invention provides an isolated specific binding member, particularly an antibody or fragment thereof, including an Fab fragment and a single chain or domain antibody, which specifically recognizes TGF-β3. In a particular aspect, the antibody or active fragment thereof neutralizes TGF-β3 activity.

The invention provides antibodies specifically directed against TGFβ3 for diagnostic and therapeutic purposes. In particular, antibodies specific for TGFβ3 are provided, wherein said antibodies are humanized and recognize and are capable of binding and neutralizing human (and mouse) TGFβ3, and do not recognize other forms of TGF-beta, TGF-β1 or TGF-β2.

The antibodies of the present invention have diagnostic and therapeutic use in cancer and in immune modulation, including modulating the immune response to cancer and in cancer vaccines. In a further aspect, the antibodies of the invention have diagnostic and therapeutic use in fibrotic conditions and fibrotic diseases. The antibodies of the invention are applicable in characterizing and in modulating the activity of TGF-β3, particularly in neutralizing TGF-β3 activity.

In a further aspect, the present invention provides an antibody or fragment thereof, particularly including a humanized antibody or fragment thereof which recognizes TGF-β3 and is selected from antibody 1901-1C comprising the heavy chain sequence of LCR1901_VH_1G10m (SEQ ID NO:18), and light chain sequence LCR1901_VK_GLv1_03(F) (SEQ ID NO:22); antibody 1901-1A comprising the heavy chain sequence of LCR1901_VH_1G10m (SEQ ID NO:18), and light chain sequence LCR1901_VK_GLv1_05(H) (SEQ ID NO:23); antibody 1901-1D comprising the heavy chain sequence of LCR1901_VH_1G10m_03(K) (SEQ ID NO:19), and light chain sequence LCR1901_VK_GLv1_03(F) (SEQ ID NO:22); and antibody 1901-1B comprising the heavy chain sequence of LCR1901_VH_1G10m_03(K) (SEQ ID NO:19), and light chain sequence LCR1901_VK_GLv1_05 (H) (SEQ ID NO:23). In a particular aspect the invention provides an antibody or active fragment thereof that specifically recognizes and neutralizes TGF-β3 and is selected from antibody 1901-1C comprising the heavy chain sequence of LCR1901_VH_1G10m (SEQ ID NO:18), and light chain sequence LCR1901_VK_GLv1_03(F) (SEQ ID NO:22); antibody 1901-1A comprising the heavy chain sequence of LCR1901_VH_1G10m (SEQ ID NO:18), and light chain sequence LCR1901_VK_GLv1_05(H) (SEQ ID NO:23); antibody 1901-1D comprising the heavy chain sequence of LCR1901_VH_1G10m_03(K) (SEQ ID NO:19), and light chain sequence LCR1901_VK_GLv1_03 (F) (SEQ ID NO:22); and antibody 1901-1B comprising the heavy chain sequence of LCR1901_VH_1G10m_03(K) (SEQ ID NO:19), and light chain sequence LCR1901_VK_GLv1_05(H) (SEQ ID NO:23).

In another aspect, antibody or active fragment thereof is provided herein comprising the heavy chain 1901 VH_1G10m_02(J) (SEQ ID NO:36). In one such aspect the antibody further comprises light chain sequence LCR1901_VK_GLv1_03(F) (SEQ ID NO:22).

The binding of an antibody to its target antigen is mediated through the complementarity-determining regions (CDRs) of its heavy and light chains. Accordingly, specific binding members based on the CDR regions of the heavy or light chain, or of both the heavy and light chain, of the antibodies of the invention, particularly of any of antibodies 1901-1A, 1901-1B, 1901-1C or 1901-1D, will be useful specific binding members for therapy and/or diagnostics. In an aspect, the invention provides TGF-β3 antibody capable of binding and neutralizing TGF-β3 comprising the light chain and heavy chain variable region CDR1, CDR2 and CDR3 sequences as provided herein and set out in FIGS. 7 and 8. In a particular aspect the invention provides TGF-β3 specific antibody capable of specifically binding and neutralizing TGF-β3, wherein the antibody does not bind or neutralize TGF-β1 or TGF-β2, comprising the light chain and heavy chain variable region CDR1, CDR2 and CDR3 sequences as provided herein and set out in FIGS. 7 and 8. In one such aspect, antibody comprising heavy chain variable region CDRs comprising a CDR1 sequence SSWIH (SEQ ID NO:1), a CDR2 sequence RIYPGDGDTDYSEKFQ (SEQ ID NO:34), and a CDR3 sequence RMITTQAALDY (SEQ ID NO:35) or ARRMITTQAAL (SEQ ID NO:30) is provided. In one further such aspect, antibody comprising heavy chain variable region CDRs comprising a CDR1 sequence SSWIH (SEQ ID NO:1) or GYTFSSSWIH (SEQ ID NO:28), a CDR2 sequence RIYPGDGDTDYSEKFQ (SEQ ID NO:34) or WIGRIYPGDGDTDYSEKFQ (SEQ ID NO:29), and a CDR3 sequence RMITTQAALDY (SEQ ID NO:35) or ARRMITTQAAL (SEQ ID NO:30) is provided. In a further aspect, antibody further comprising light chain variable region CDRs comprising a CDR1 sequence KASQSVINAVA (SEQ ID NO:4), a CDR2 sequence YASNRYT (SEQ ID NO:5), and a CDR3 sequence QQDYSSPY (SEQ ID NO:33) is provided. In another further aspect, antibody comprising light chain variable region CDRs comprising a CDR1 sequence KASQSVINAVA (SEQ ID NO:4) or KASQSVINAVAWY (SEQ ID NO:31), a CDR2 sequence YASNRYT (SEQ ID NO:5) or LLIYYASNRYT (SEQ ID NO:32), and a CDR3 sequence QQDYSSPY (SEQ ID NO:33) or QQDYSSPYT (SEQ ID NO:6) is provided.

In an aspect, the invention provides an antibody directed against TGF-β3 comprising a heavy chain variable region comprising CDRs comprising a CDR1 sequence SSWIH (SEQ ID NO:1), a CDR2 sequence RIYPGDGDTDYSEKFQ (SEQ ID NO:34), and a CDR3 sequence comprising the sequence RMITTQAAL (SEQ ID NO:37). In one such aspect, the antibody comprises a heavy chain variable region comprising a CDR1 sequence SSWIH (SEQ ID NO:1), a CDR2 sequence RIYPGDGDTDYSEKFQ (SEQ ID NO:34), and a CDR3 sequence comprising RMITTQAAL (SEQ ID NO:37). In an aspect, the antibody comprises a heavy chain variable region comprising a CDR1 sequence SSWIH (SEQ ID NO:1), a CDR2 sequence RIYPGDGDTDYSEKFQ (SEQ ID NO:34), and a CDR3 sequence RMITTQAAL (SEQ ID NO:37). In a further aspect, antibody further comprising light chain variable region CDRs comprising a CDR1 sequence KASQSVINAVA (SEQ ID NO:4), a CDR2 sequence YASNRYT (SEQ ID NO:5), and a CDR3 sequence QQDYSSPY (SEQ ID NO:33) is provided. In another further aspect, antibody comprising light chain variable region CDRs comprising a CDR1 sequence KASQSVINAVA (SEQ ID NO:4) or KASQSVINAVAWY (SEQ ID NO:31), a CDR2 sequence YASNRYT (SEQ ID NO:5) or LLIYYASNRYT (SEQ ID NO:32), and a CDR3 sequence QQDYSSPY (SEQ ID NO:33) or QQDYSSPYT (SEQ ID NO:6) is provided. In one aspect, the antibody specifically binds and neutralizes TGF-β3 and does not bind and/or does not neutralize TGF-β1 or TGF-β2. The invention provides an antibody directed against TGF-β3 comprising a heavy chain variable region sequence comprising a CDR1 sequence SSWIH (SEQ ID NO:1), a CDR2 sequence RIYPGDGDTDYSEKFQ (SEQ ID NO:34), and a CDR3 sequence RMITTQAALDY (SEQ ID NO:35); or a CDR1 sequence GYTFSSSWIH (SEQ ID NO:28), a CDR2 sequence WIGRIYPGDGDTDYSEKFQ (SEQ ID NO:29), and a CDR3 sequence ARRMITTQAAL (SEQ ID NO:30). In an aspect, the invention provides an antibody further comprising a light chain variable region sequence comprising a CDR1 sequence KASQSVINAVA (SEQ ID NO:4), a CDR2 sequence YASNRYT (SEQ ID NO:5), and a CDR3 sequence QQDYSSPY (SEQ ID NO:33) or QQDYSSPYT (SEQ ID NO:6); or a CDR1 sequence KASQSVINAVAWY (SEQ ID NO:31), a CDR2 sequence LLIYYASNRYT (SEQ ID NO:32), and a CDR3 sequence QQDYSSPY (SEQ ID NO:33) or QQDYSSPYT (SEQ ID NO:6). In an aspect, the antibody comprises variable region sequences which are humanized or are altered or modified to increase their similarity to antibodies produced naturally in humans. In an aspect, the antibody comprises variable region sequences which are humanized or are altered or modified in the framework regions to increase their similarity to antibodies produced naturally in humans.

In a particular aspect, the isolated antibody or fragment of the invention neutralizes TGF-β3. In a particular aspect, the isolated antibody or fragment of the invention does not react with TGF-β1 or TGF-β2. In an aspect, the isolated antibody or fragment of the invention binds and neutralizes TGF-β3 and does not react with or does not bind to TGF-β1 or TGF-β2.

In one aspect, the invention provides an antibody specifically directed against and neutralizing TGF-β3, wherein the antibody does not bind or neutralize TGF-β1 or TGF-β2, comprising a heavy chain variable region sequence comprising a CDR1 sequence SSWIH (SEQ ID NO:1), a CDR2 sequence RIYPGDGDTDYSEKFQ (SEQ ID NO:34), and a CDR3 sequence RMITTQAALDY (SEQ ID NO:35) or ARRMITTQAAL (SEQ ID NO:30). In a further aspect, the invention provides an antibody specifically directed against and neutralizing TGF-β3, wherein the antibody does not bind or neutralize TGF-β1 or TGF-β2, comprising a heavy chain variable region sequence comprising a CDR1 sequence SSWIH (SEQ ID NO:1), a CDR2 sequence RIYPGDGDTDYSEKFQ (SEQ ID NO:34), and a CDR3 sequence RMITTQAALDY (SEQ ID NO:35) or ARRMITTQAAL (SEQ ID NO:30), and a light chain variable region sequence comprising a CDR1 sequence KASQSVINAVA (SEQ ID NO:4), a CDR2 sequence YASNRYT (SEQ ID NO:5), and a CDR3 sequence QQDYSSPY (SEQ ID NO:33).

In an aspect, the invention provides an antibody specifically directed against and neutralizing TGF-β3, wherein the antibody does not bind or neutralize TGF-β1 or TGF-β2, comprising a heavy chain variable region sequence comprising a CDR1 sequence SSWIH (SEQ ID NO:1), a CDR2 sequence RIYPGDGDTDYSEKFQ (SEQ ID NO:34), and a CDR3 sequence RMITTQAALDY (SEQ ID NO:35) or ARRMITTQAAL (SEQ ID NO:30), and a light chain variable region sequence comprising a CDR1 sequence KASQSVINAVA (SEQ ID NO:4), a CDR2 sequence YASNRYT (SEQ ID NO:5), and a CDR3 sequence QQDYSSPY (SEQ ID NO:33) or QQDYSSPYT (SEQ ID NO:6); or a CDR1 sequence KASQSVINAVAWY (SEQ ID NO:31), a CDR2 sequence LLIYYASNRYT (SEQ ID NO:32), and a CDR3 sequence QQDYSSPY (SEQ ID NO:33) or QQDYSSPYT (SEQ ID NO:6).

In one aspect, the invention provides an antibody specifically directed against and neutralizing TGF-β3, wherein the antibody does not bind or neutralize TGF-β1 or TGF-β2, comprising a heavy chain variable region sequence comprising a CDR1 sequence SSWIH (SEQ ID NO:1), a CDR2 sequence RIYPGDGDTDYSEKFQ (SEQ ID NO:34), and a CDR3 sequence RMITTQAALDY (SEQ ID NO:35); or a CDR1 sequence GYTFSSSWIH (SEQ ID NO:28), a CDR2 sequence WIGRIYPGDGDTDYSEKFQ (SEQ ID NO:29), and a CDR3 sequence ARRMITTQAAL (SEQ ID NO:30), and a light chain variable region sequence comprising a CDR1 sequence KASQSVINAVA (SEQ ID NO:4), a CDR2 sequence YASNRYT (SEQ ID NO:5), and a CDR3 sequence QQDYSSPY (SEQ ID NO:33) or QQDYSSPYT (SEQ ID NO:6); or a CDR1 sequence KASQSVINAVAWY (SEQ ID NO:31), a CDR2 sequence LLIYYASNRYT (SEQ ID NO:32), and a CDR3 sequence QQDYSSPY (SEQ ID NO:33) or QQDYSSPYT (SEQ ID NO:6).

In one aspect, the invention provides an antibody specifically directed against and neutralizing TGF-β3, wherein the antibody does not bind or neutralize TGF-β1 or TGF-β2, comprising a heavy chain variable region sequence comprising a CDR1 sequence SSWIH (SEQ ID NO:1) or GYTFSSSWIH (SEQ ID NO:28), a CDR2 sequence RIYPGDGDTDYSEKFQ (SEQ ID NO:34) or WIGRIYPGDGDTDYSEKFQ (SEQ ID NO: 29), and a CDR3 sequence RMITTQAALDY (SEQ ID NO:35) or ARRMITTQAAL (SEQ ID NO:30), and a light chain variable region sequence comprising a CDR1 sequence KASQSVINAVA (SEQ ID NO:4) or KASQSVINAVAWY (SEQ ID NO:31), a CDR2 sequence YASNRYT (SEQ ID NO:5) or LLIYYASNRYT (SEQ ID NO:32), and a CDR3 sequence QQDYSSPY (SEQ ID NO:33) or QQDYSSPYT (SEQ ID NO:6).

In a further aspect, the invention provides an antibody, particularly a humanized antibody, comprising a heavy chain variable region sequence LCR1901_VH_1G10m (SEQ ID NO:18) or LCR1901_VH_1G10m_03(K) (SEQ ID NO:19) or a variant thereof having at least 90% amino acid identity to the heavy chain variable region sequence LCR1901_VH_1G10m (SEQ ID NO:18) or LCR1901_VH_1G10m_03(K) (SEQ ID NO:19) or comprising 1 to 3 amino acid substitutions in one or more heavy chain CDR region of FIG. 7 (SEQ ID NOs: 1, 34 and 35 or 30, SEQ ID NO:s 28, 29 and 30 or SEQ ID NO:s 1, 34 and 35), wherein said variant retains TGF-β3 reactivity and neutralization and lack of TGF-β1 and TGF-β2 reactivity. In a particular aspect, the invention provides a humanized antibody comprising a heavy chain variable region sequence LCR1901_VH_1G10m (SEQ ID NO:18) or LCR1901_VH_1G10m_03(K) (SEQ ID NO:19).

In a further aspect, the invention provides an antibody, particularly a humanized antibody, comprising a heavy chain variable region sequence LCR1901_VH_1G10m_02 (J) (SEQ ID NO:36) or a variant thereof having at least 90% amino acid identity to the heavy chain variable region sequence LCR1901_VH_1G10m_02(J) (SEQ ID NO:36) or comprising 1 to 3 amino acid substitutions in one or more heavy chain CDR region of FIG. 7 (SEQ ID NOs: 1, 34 and 35 or 30, SEQ ID NO:s 28, 29 and 30 or SEQ ID NO:s 1, 34 and 35), wherein said variant retains TGF-β3 reactivity and neutralization and lack of TGF-β1 and TGF-β2 reactivity. In a particular aspect, the invention provides a humanized antibody comprising a heavy chain variable region sequence LCR1901_VH_1G10m_02(J) (SEQ ID NO:36).

The antibody of the invention may comprise the heavy chain variable region CDR domain region sequences CDR1 sequence SSWIH (SEQ ID NO:1), a CDR2 sequence RIYPGDGDTDYSEKFQ (SEQ ID NO:34), and a CDR3 sequence RMITTQAALDY (SEQ ID NO:35) or ARRMITTQAAL (SEQ ID NO:30); CDR1 sequence SSWIH (SEQ ID NO:1), a CDR2 sequence RIYPGDGDTDYSEKFQ (SEQ ID NO:34), and a CDR3 sequence RMITTQAALDY (SEQ ID NO:35); or a CDR1 sequence GYTFSSSWIH (SEQ ID NO:28), a CDR2 sequence WIGRIYPGDGDTDYSEKFQ (SEQ ID NO:29), and a CDR3 sequence ARRMITTQAAL (SEQ ID NO:30), and a light chain variable region. The antibody of the invention may comprise the heavy chain variable region CDR domain region sequences CDR1 sequence SSWIH (SEQ ID NO:1) or GYTFSSSWIH (SEQ ID NO:28), a CDR2 sequence RIYPGDGDTDYSEKFQ (SEQ ID NO:34) or WIGRIYPGDGDTDYSEKFQ (SEQ ID NO:29), and a CDR3 sequence RMITTQAALDY (SEQ ID NO:35) or ARRMITTQAAL (SEQ ID NO:30), and a light chain variable region. In an aspect, the TGF-β3 antibody further comprises the light chain variable region CDR sequences CDR1 sequence KASQSVINAVA (SEQ ID NO:4), a CDR2 sequence YASNRYT (SEQ ID NO:5), and a CDR3 sequence QQDYSSPY (SEQ ID NO:33) or QQDYSSPYT (SEQ ID NO:6); or a CDR1 sequence KASQSVINAVAWY (SEQ ID NO:31), a CDR2 sequence LLIYYASNRYT (SEQ ID NO:32), and a CDR3 sequence QQDYSSPY (SEQ ID NO:33) or QQDYSSPYT (SEQ ID NO:6). In an aspect of the invention, the TGF-β3 specific neutralizing antibodies with alternative heavy and light chain CDR sequences compete with one another for TGF-β3 binding.

In an aspect, the TGF-β3 specific antibody of the invention comprises the heavy chain variable amino acid SEQ ID NO: 18 or SEQ ID NO: 19. In an aspect, the TGF-β3 specific antibody of the invention comprises the heavy chain variable amino acid SEQ ID NO: 18, SEQ ID NO: 19 or SEQ ID NO:36. In a particular aspect, a TGF-β3 antibody of the invention comprises the heavy chain and light chain variable region amino acid sequence as set out in any of FIG. 10 (SEQ ID NOs: 18 and 22), FIG. 11 (SEQ ID NOs: 18 and 23), FIG. 12 (SEQ ID NOs: 19 and 22), or FIG. 13 (SEQ ID NOs: 19 and 23). A TGF-β3 antibody of the invention may comprise an amino acid sequence having at least 80%, at least 90%, at least 95%, at least 98%, at least 99% amino acid identity to the heavy chain variable region amino acid sequence and the light chain variable region amino acid sequence as set out in FIG. 10, 11, 12 or 13 (SEQ ID NOs: 18 and 22, 18 and 23, 19 and 22, 19 and 23). In an aspect, the TGF-β3 antibody of the invention comprises the heavy chain variable region SEQ ID NO:36. In a further aspect, the TGF-β3 antibody of the invention comprises the heavy chain variable region SEQ ID NO:36 and light chain variable region SEQ ID NO:22. In a further aspect, the TGF-β3 antibody of the invention comprises the heavy chain variable region SEQ ID NO:36 and light chain variable region SEQ ID NO:22 or SEQ ID NO:23. A TGF-β3 specific antibody of the invention, capable of specifically binding TGF-β3 and which does not bind TGF-β1 or TGF-β2, may comprise an amino acid sequence having at least 80%, at least 90%, at least 95%, at least 98%, at least 99% amino acid identity to the heavy chain variable region amino acid sequence SEQ ID NO: 18 or SEQ ID NO: 19. A TGF-β3 specific antibody of the invention, capable of specifically binding TGF-β3 and which does not bind TGF-β1 or TGF-β2, may comprise an amino acid sequence having at least 80%, at least 90%, at least 95%, at least 98%, at least 99% amino acid identity to the heavy chain variable region amino acid sequence SEQ ID NO:36. In a further aspect a TGF-β3 specific antibody of the invention, capable of specifically binding TGF-β3 and which does not bind TGF-β1 or TGF-β2, may comprise an amino acid sequence having at least 80%, at least 90%, at least 95%, at least 98%, at least 99% amino acid identity to the light chain variable region amino acid sequence SEQ ID NO: 22 or SEQ ID NO:23.

A TGF-β3 specific antibody of the invention, capable of specifically binding TGF-β3 and which does not bind TGF-β1 or TGF-β2, may comprise an amino acid sequence having at least 80%, at least 90%, at least 95%, at least 98%, at least 99% amino acid identity to the heavy chain variable region amino acid sequence SEQ ID NO: 18 or SEQ ID NO: 19 and further having at least 80%, at least 90%, at least 95%, at least 98%, at least 99% amino acid identity to the light chain variable region amino acid sequence SEQ ID NO: 22 or SEQ ID NO:23. A TGF-β3 specific antibody of the invention, capable of specifically binding TGF-β3 and which does not bind TGF-β1 or TGF-β2, may comprise an amino acid sequence having at least 80%, at least 90%, at least 95%, at least 98%, at least 99% amino acid identity to the heavy chain variable region amino acid sequence SEQ ID NO: 18 or SEQ ID NO: 19 or SEQ ID NO: 36 and further having at least 80%, at least 90%, at least 95%, at least 98%, at least 99% amino acid identity to the light chain variable region amino acid sequence SEQ ID NO: 22 or SEQ ID NO:23.

In a particular aspect, the antibody or active fragment thereof of the present invention neutralizes human and mouse TGF-β3. In an aspect, antibody of the invention neutralizes and blocks TGF-β3-mediated signaling in vivo in a mammal, particularly in a human or in a mouse. In an aspect, the antibody or active fragment thereof of the present invention neutralizes and blocks TGF-β3-mediated signaling in vivo in a mammal, without neutralizing or blocking TGF-β1 or TGF-β2 signaling in vivo in a mammal.

Accordingly, specific binding proteins such as antibodies which are based on the CDRs of the antibody(ies), particularly including the heavy chain CDRs identified herein, will be useful for targeting TGF-β3, particularly TGF-β3 expressing cells, or TGF-β3 activity in immune response, in diseases or in cancers. As the target of antibodies of the invention is specifically TGF-β3 and not TGF-β1 and/or TGF-β2, in an aspect of the invention the antibodies of the invention do no significantly bind to TGF-β forms or family members other than TGF-β3 and it is anticipated that there will be less toxicity and inflammatory response or untoward immune response or reaction in cell targets or in animals with the present TGF-β3 specific antibodies, particularly as compared to a more non-specific TGF-β antibody, such as a pan-TGF-β antibody which recognizes more than one form of TGF-β or all forms of TGF-β.

In another aspect of the invention, provided herein is an antibody(ies) or antigen-binding fragment(s) thereof that competes with an antibody or antigen-binding fragment thereof described herein for binding to TGF-β3 (e.g., human TGF-β3). In a specific embodiment, provided herein is an antibody(ies) or antigen-binding fragment(s) thereof that competes with antibody or antigen-binding fragment thereof described herein for binding to TGF-β3 (e.g., human TGF-β3) to the extent that the antibody or antigen-binding fragment thereof described herein self-competes for binding to TGF-β3 (e.g., human TGF-β3).

In another specific embodiment, provided herein is a first antibody or antigen-binding fragment thereof that competes with an antibody or antigen-binding fragment thereof described herein for binding to TGF-β3 (e.g., human TGF-β3), wherein the competition is exhibited as reduced binding of first antibody or antigen-binding fragment thereof to TGF-β3 (e.g., human TGF-β3) by more than 60% (e.g., 65%, 70%, 75%, 85%, 90%, 95%, or 98%, or between 60% to 65%, 65% to 70%, 70% to 75%, 75% to 80%, 80% to 85%, 85% to 95%, or 95% to 100%). In another specific embodiment, provided herein is a first antibody or antigen-binding fragment thereof that competes with an antibody or antigen-binding fragment thereof described herein for binding to TGF-β3 (e.g., human TGF-β3), wherein the competition is exhibited as reduced binding of antibody or antigen binding fragment of one or more of antibody 1901-1A, 1901-1B, 1901-1C or 1901-1D by more than 60% (e.g., 65%, 70%, 75%, 85%, 90%, 95%, or 98%, or between 60% to 65%, 65% to 70%, 70% to 75%, 75% to 80%, 80% to 85%, 85% to 95%, or 95% to 100%) in the presence and/or after binding of the first antibody or antigen-binding fragment thereof.

In specific aspects, provided herein is an antibody which competes (e.g., in a dose dependent manner) for specific binding to TGF-β3 (e.g., human TGF-β3), with an antibody comprising (i) a VL domain comprising a VL CDR1, VL CDR2, and VL CDR3 having the amino acid sequences of the VL CDRs of an antibody listed in FIG. 8 or in FIGS. 10-13; and (ii) a VH domain comprising a VH CDR1, VH CDR2, and VH CDR3 having the amino acid sequences of the CDRs of an antibody listed in FIG. 7 or in FIGS. 10-13. In a specific aspect, provided herein is an antibody which competes (e.g., in a dose dependent manner) for specific binding to TGF-β3 (e.g., human TGF-β3), with an antibody comprising a VH domain comprising CDR1 sequence SSWIH (SEQ ID NO:1), a CDR2 sequence RIYPGDGDTDYSEKFQ (SEQ ID NO:34), and a CDR3 sequence RMITTQAALDY (SEQ ID NO:35) or ARRMITTQAAL (SEQ ID NO:30), optionally further comprising or further comprising a VL domain comprising a CDR1 KASQSVINAVA (SEQ ID NO:4)), a CDR2 sequence YASNRYT (SEQ ID NO:5), and a CDR3 sequence QQDYSSPY (SEQ ID NO:33).

In a particular embodiment, provided herein is an antibody that competes (e.g., in a dose-dependent manner), for specific binding to TGF-β3 (e.g., human TGF-β3), with an antibody comprising the VH CDRs of 1901-1A, 1901-1B, 1901-1C or 1901-1D, particularly SEQ ID NOs: 1, 34 and 35 or 30, SEQ ID NOs: 28-30 or SEQ ID NO: 1, 34 and 35. In a particular embodiment, provided herein is an antibody that competes (e.g., in a dose-dependent manner), for specific binding to TGF-β3 (e.g., human TGF-β3), with an antibody comprising the VL CDRs of 1901-1A, 1901-1B, 1901-1C or 1901-1D, particularly SEQ ID NOs: 4, 5 and 33, SEQ ID NOs: 31-33 or SEQ ID NOs: 4-6.

In a specific embodiment, an antibody described herein is one that is competitively blocked (e.g., in a dose dependent manner) by an antibody comprising a VH domain having the amino acid sequence SEQ ID NO: 18 or SEQ ID NO:19 for specific binding to TGF-β3 (e.g., human TGF-β3). In a specific embodiment, an antibody described herein is one that is competitively blocked (e.g., in a dose dependent manner) by an antibody comprising a VH domain having the amino acid sequence SEQ ID NO: 18 or SEQ ID NO:19 or SEQ ID NO:36 for specific binding to TGF-β3 (e.g., human TGF-β3). In a specific embodiment, an antibody described herein is one that is competitively blocked (e.g., in a dose dependent manner) by an antibody comprising a VH domain having the amino acid sequence SEQ ID NO: 18 or SEQ ID NO:19 or SEQ ID NO: 36 and a VL domain having the amino acid sequence SEQ ID NO:22 or SEQ ID NO:23, for specific binding to TGF-β3 (e.g., human TGF-β3).

In further aspects, the invention provides an isolated nucleic acid which comprises a sequence encoding a specific binding member or antibody as defined above or herein, and methods of preparing specific binding members or antibodies of the invention which comprise expressing said nucleic acids under conditions to bring about expression of said binding member or antibody, and recovering the binding member or antibody. In one such aspect, a nucleic acid encoding antibody variable region sequence having the heavy chain amino acid sequences as set out in FIG. 10, 11, 12 or 13 is provided or an antibody having heavy chain CDR domain sequences as set out in FIG. 7 and SEQ ID NOs:1, 34, 35, 28, 29, 30, or in FIG. 10, 11 12 or 13 is provided. In an aspect, nucleic acid encoding an antibody light chain variable region having the light chain amino acid sequences as set out in FIG. 10, 11, 12 or 13 is provided or an antibody having light chain CDR domain sequences as set out in FIG. 8 and in SEQ ID NOs:4, 5, 6, 31, 32, 33, or in FIG. 10, 11, 12 or 13 is provided. The present invention also relates to a recombinant DNA molecule or cloned gene, or a degenerate variant thereof, which encodes an antibody of the present invention; preferably a nucleic acid molecule, in particular a recombinant DNA molecule or cloned gene, encoding the antibody VH, particularly the CDR region sequences, and optionally additionally encoding the VL, particularly the CFR region sequences, which is capable of encoding a heavy chain sequence SEQ ID NO:18 or 19 or 36 and a light chain sequence SEQ ID NO: 22 or 23, or combinations of such heavy and light chain variable region sequences, including as set out on FIGS. 10, 11 12 and 13.

The unique specificity and affinity of the antibodies and fragments of the invention provides diagnostic and therapeutic uses to identify, characterize and target conditions associated with TGF-β3 expression, activity or activation. Thus, methods and aspects thereof are provided in accordance with the invention. In one aspect, antibodies of the invention targeting TGF-β3 are useful in modulating immune response, including in modulating immune response against cancer, cancer or tumor cells, and cancer or tumor antigens. In another aspect, antibodies of the invention targeting TGF-β3 are useful in therapeutic treatment or management of cancer, in enhancing the anti-cancer immune response and in enhancing cancer vaccines. The antibodies have applicability in enhancing the therapeutic effect including the anti-cancer and/or anti-cellular effect of cancer therapy(ies), including traditional anti-cancer agents and compounds and cell therapies including cancer-targeting T cell therapies. The antibodies have applicability in enhancing the therapeutic effect including the anti-cancer and/or anti-cellular effect of radiation therapy(ies). In a particular aspect the antibodies of the invention are applicable in treatment, management and/or prevention of cancers, including in cancer recurrence and metastasis. In an aspect, the TGF-β3 antibodies of the invention have applicability in treatment or modulation of breast, melanoma, prostate or lung cancer.

In accordance with the invention, methods for treatment, alleviation or modulation of cancer comprising administering the antibodies of the invention or pharmaceutical compositions thereof are provided herein. In a further aspect, methods for stimulating or enhancing an immune response to a vaccine or antigen or an immunomodulatory agent or radiation therapy in a mammal comprising administering the antibodies of the invention or pharmaceutical compositions thereof are provided herein.

In an aspect of the invention TGF-β3 antibody(ies), particularly TGF-β3 neutralizing antibody(ies) as provided herein, particularly humanized antibodies, may be administered in conjunction with or in a composition of cancer antigen(s) and adjuvant(s), including to patients to promote a more robust priming and activation of the adaptive anti-tumor response to enhance immune therapies directed at cancers. Additional inhibitors to TGFβ activity, such as small molecules, antisense or aptamers can also be used to inhibit TGFβ activity, including or specifically TGF-β3.

Thus, in an aspect of the invention the anti-TGF-β3 antibody(ies) may be administered alone or in combination with other treatments, therapeutics or agents or cell therapies, either simultaneously or sequentially dependent upon the condition to be treated. Immune modulators may be included in a composition with or administered with TGF-β3 antibody(ies) and/or administered at a different time to enhance immune modulation and/or cancer therapy, including immune therapies or cell therapies directed against cancer. An immune modulator may be an adjuvant. In a further aspect, the TGF-β3 antibodies of the invention can also be used as immunostimulant(s) or adjuvant(s) in combined use with antigenic materials such as, without limitation, proteins, peptides, or nucleic acids and so forth in order to produce a protective immune response, such as a T-cell or CTL response to the administered antigen.

The invention provides a method for improving, facilitating or enhancing chimeric antigen receptor (CAR) T cell therapy comprising administering one or more anti-TGF-β3 antibody(ies) or a fragment thereof, either simultaneously or sequentially with the CAR T cell(s). In an aspect of the method, the one or more anti-TGF-β3 antibody(ies) or a fragment thereof is added to CAR T cell culture before administration or infusion. In an aspect, the one or more anti-TGF-β3 antibody(ies) or a fragment thereof, such as an scfv thereof, are expressed by or on the CAR T cell(s). In another method of the invention, one or more anti-TGF-β3 antibody(ies) or a fragment thereof are administered in combination with activated T cells or T cells directed against a cancer antigen or cell cycle regulator.

In accordance with the invention, methods for treatment, alleviation or modulation of fibrotic conditions or fibrotic diseases comprising administering the antibodies of the invention or pharmaceutical compositions thereof are provided herein. In an aspect, methods for treatment, alleviation or modulation of conditions or diseases wherein extracellular matrix formation is altered are provided herein comprising administering the antibodies of the invention or pharmaceutical compositions thereof. In an aspect of these methods, the antibodies of the invention may be administered in conjunction with or combined with one or more anti-inflammatory agent, an immunosuppressant, an immune response modulator, an antioxidant or an antifibrotic drug or agent. In one such aspect, the antibody(ies) of the invention are combined with or administered in conjunction with treatments for fibrosis. In one such aspect, methods for treatment or modulation of pulmonary fibrosis are provided. In an aspect, antibody(ies) of the invention are combined with or administered in conjunction with fibrosis treatments, particularly selected from nintedanib (OFEV®) and pirfenidone (Esbriet®)

TGF-β3 antibodies, including TGF-β3 specific antibodies, are efficacious both in vitro and in vivo as has been shown. Hence, one aspect of the invention relates to stimulating an immune response in a subject, by administering one or more TGF-β3 antibody(ies) of the invention with or without an antigenic molecule, in an amount sufficient to stimulate a favorable immunologic response in such subject.

The invention includes compositions and or kits, comprising one or more TGF-β3 antibody(ies) of the invention together with one or more immunogenic proteins or peptides. The compositions include pharmaceutical compositions and immunological compositions. The antibodies or compositions of the invention may be administered systemically or in a targeted fashion, including administration to an affected organ or organ of interest to a tumor, at the region or location of a tumor, or directly to a tumor, such as in intratumoral injection.

The antibodies, fragments thereof and recombinant antibodies comprising the CDR domains according to the invention may be used in a method of treatment or diagnosis of the human or animal body, such as a method of treatment of a tumor in a human patient which comprises administering to said patient an effective amount of the antibodies, fragments thereof and recombinant antibodies of the invention. The antibodies, fragments thereof and recombinant antibodies comprising the CDR domains according to the invention may be used in a method of stimulating or enhancing an immune response to cancer, tumor cells or cancer or tumor antigen(s) in a mammal, particularly in a human, comprises administering to said mammal an effective amount of the antibodies, fragments thereof and recombinant antibodies of the invention. The antibodies, fragments thereof and recombinant antibodies comprising the CDR domains according to the invention may be used in a method of inhibiting or reducing recurrence or metastasis of cancer in a mammal, particularly in a human, comprises administering to said mammal an effective amount of the antibodies, fragments thereof and recombinant antibodies of the invention. The antibodies, fragments thereof and recombinant antibodies comprising the CDR domains according to the invention may be used in a method of inhibiting or blocking stimulation of TGFβ, particularly TGFβ3, in response to radiation or cancer therapy in a mammal, particularly in a human, comprising administering to said mammal an effective amount of the antibodies, fragments thereof and recombinant antibodies of the invention. In an aspect of the method, the TGF-β3 specific antibodies, fragments thereof and recombinant antibodies comprising the CDR domains according to the invention are administered in combination or subsequent to radiation therapy and/or cancer therapy in a mammal.

A therapeutic method of the invention is associated with the prevention or treatment of cancer, or the stimulation or enhancement of immune response to cancer, or the inhibition of immune-mediated protection of cancer cells, including melanoma, breast, prostate and lung cancer. In an aspect of the method, the specific TGF-β3 neutralizing antibodies of the invention, including active fragments thereof, serve to stimulate or enhance an immune response to cancer, including melanoma, breast, prostate and lung cancer. In an aspect, immune responses via a cancer vaccine or cancer immunotherapy or via cell therapies such as cancer targeted T cell therapy, including radiation therapy, are stimulated or enhanced by one or more specifically neutralizing TGF-β3 antibody or active fragment thereof of the invention.

The antibodies of the present invention, and in a particular embodiment the antibody having sequence represented in FIG. 10, 11, 12 or 13, or active fragments thereof, and single chain, recombinant or synthetic antibodies derived therefrom, particularly comprising the heavy chain CDR region sequences and the light chain CDR region sequences depicted in FIGS. 7 and 8, including comprising heavy chain CDRs SEQ ID NOs: 1, 34 and 35 or 30 and light chain CDRs SEQ ID NOs: 4, 5 and 33, can be expressed in immune cells, including lymphoid cells, including T cells. In one such aspect, the antibodies, or active fragments thereof, and single chain, recombinant or synthetic antibodies derived therefrom, are expressed and secreted by lymphoid cells, including T cells. The lymphoid cells, such as T cells, can be prepared and utilized for therapy, including immune modulation and for cancer therapy. In one aspect, the lymphoid cells, such as T cells, expressing one or more TGFβ3 antibody of the invention can be further engineered to express another/other protein(s), such as a receptor. In one aspect, the lymphoid cells, such as T cells, expressing one or more TGFβ3 antibody of the invention can be combined with lymphoid cells, such as T cells, engineered to express another/other protein(s), such as a receptor. In an aspect, the receptor is a chimeric antigen receptor (CAR). In an aspect, the receptor is a T cell receptor. In one aspect the another/other protein(s) is a cancer antigen or a tumor antigen or a tumor antigen antibody or fragment thereof or an immunomodulatory agent. The invention provides methods of treatment comprising administering to a mammal the lymphoid cells, such as T cells, expressing one or more TGFβ3 antibody of the invention. In an aspect, the method is directed to treatment of cancer or prevention of recurrence or metastasis of cancer. In an aspect, the method is directed to modulation of immune response, including in cancer or cancer therapy.

The binding members and antibodies of the present invention, and in a particular embodiment the antibody having sequence represented in FIG. 10, 11, 12 or 13, or active fragments thereof, and single chain, recombinant or synthetic antibodies derived therefrom, particularly comprising the heavy chain CDR region sequences and the light chain CDR region sequences depicted in FIGS. 7 and 8, including comprising heavy chain CDRs SEQ ID NOs: 1, 34 and 35 or 30 and light chain CDRs SEQ ID NOs: 4, 5 and 33, can be prepared in pharmaceutical compositions, including a suitable vehicle, carrier or diluent, or including an adjuvant and/or immune modulator, for administration. Such pharmaceutical compositions may also include means for modulating the half-life of the antibodies or fragments by methods known in the art such as pegylation.

Pharmaceutical compositions or immunogenic compositions of the invention may further comprise additional antibodies or therapeutic agents. In an aspect, such other agents or therapeutics may be selected from anti-cancer agents or therapeutics, anti-mitotic agents, apoptotic agents or antibodies, or immune modulators, or small molecule inhibitors to immune modulators. More generally these anti-cancer agents may be tyrosine kinase inhibitors or phosphorylation cascade inhibitors, post-translational modulators, cell growth or division inhibitors (e.g. anti-mitotics), inhibitors or signal transduction inhibitors. The composition may be administered with an immune modulator such as an adjuvant. The composition may also be administered with, or may include combinations along with other anti-TGFβ antibodies, other immunomodulatory antibodies or other anti-tumor antigen antibodies.

The diagnostic utility of the present invention extends to the use of the antibodies of the present invention in assays to characterize tumors or cellular samples or to screen for tumors or cancer, including in vitro and in vivo diagnostic assays. Antibodies of the invention may carry a detectable or functional label. The specific binding members may carry a radioactive label, such as the isotopes, $^{3}H$, $^{14}C$, $^{32}P$, $^{35}S$, $^{36}Cl$, $^{51}Cr$, $^{57}Co$, $^{58}Co$, $^{59}Fe$, $^{90}Y$, $^{121}I$, $^{124}I$, $^{125}I$, $^{131}I$, $^{111}In$, $^{117}Lu$, $^{211}At$, $^{198}Au$, $^{67}Cu$, $^{225}Ac$, $^{213}Bi$, $^{99}Tc$, and $^{186}RE$. In an aspect, the label may be an enzyme, including wherein detection may be accomplished by any of the presently utilized colorimetric, spectrophotometric, fluorospectrophotometric, amperometric or gasometric techniques known in the art.

Immunoconjugates or antibody fusion proteins of the present invention, wherein the specific binding members, particularly antibodies and fragments thereof, of the present invention are conjugated or attached to other molecules or agents further include, but are not limited to binding members conjugated to a chemical ablation agent, toxin, immunomodulator, cytokine, cytotoxic agent, chemotherapeutic agent or drug.

The present invention includes an assay system which may be prepared in the form of a test kit for the quantitative analysis of the extent of the presence of, for instance, TGFβ3. The system or test kit may comprise a labeled component prepared by one of the radioactive and/or enzymatic techniques discussed herein, coupling a label to the antibody, and one or more additional immunochemical reagents, at least one of which is a free or immobilized components to be determined or their binding partner(s).

Other objects and advantages will become apparent to those skilled in the art from a review of the ensuing detailed description, which proceeds with reference to the following illustrative drawings, and the attendant claims.

BRIEF DESCRIPTION OF THE DRAWINGS

FIG. 1 depicts the cloned hybridoma murine 1901 antibody parental VH and VK nucleic acid (denoted _genscript_DNA) (SEQ ID NOs: 9 and 11) and VH and VK amino acid sequences (denoted _genscript_AA) (SEQ ID NOs: 10 and 12). The grey shaded XXXXXX are native signal peptides present in the Genscript sequences.

FIG. 3 depicts the amino acid sequence of grafted murine 1901 (SEQ ID NO: 13) versus LCR1901_Glv1 (SEQ ID NO:14) and grafting of IGKV1-39*01/IGHV1-69*08. Murine CDR cores in bold; Vernier residues are underlined; scFv linker in grey italics (CLUSTAL 0(1.2.1) multiple sequence alignment). Homology: (*) conserved sequence; (:) conservative mutation; (.) semi-conservative mutation; ( ) non-conservative mutation.

FIG. 6 tabulates CDR/junctional VH and VK residues with potential sequence liabilities their suggested corrections and final selected residue based on a competive binding assay. IMGT numbering utilized for amino acid residue sequence numbers.

FIG. 7 provides VH protein sequences and the LCR-hu1901 CDR grafting outline for VH chains. The tabulated sequences are as follows: murine 1901 VH protein sequence (SEQ ID NO: 15), LCR1901_Glv1 (grafted onto huIgHV1-69*09 framework) (SEQ ID NO:16), LCR1901 VH_1G10 (SEQ ID NO:17), LCR1901 VH_1G10m (SEQ ID NO: 18), LCR1901 VH_1G10m_Glv1_03 (SEQ ID NO:19) and LCR1901 VH_1G10m_02(J) (SEQ ID NO:36). X=alterations from original graft; X*=mouse residues maintained; #=back-mutation of human to original mouse. IMGT numbering utilized for amino acid residue sequence numbers. CDRs (in bold) and Vernier regions grafted; parental IGHJ retained.

Figure 2:
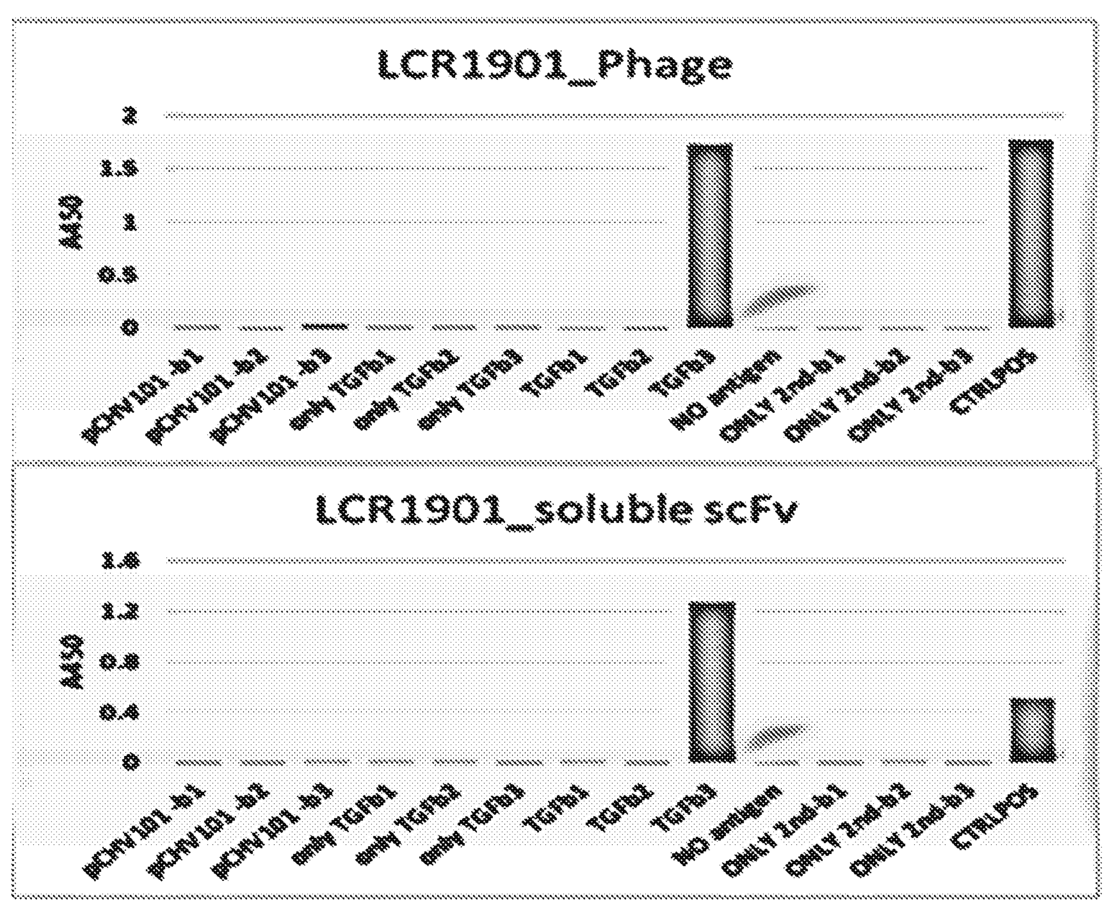
FIG. 2 graphs ELISA results of LCR1901_phage and LCR1901_soluble scFv, demonstrating that reformatting of murine mAb 1901 variable domains to scFv preserves binding and fine specificity recognition for TGFb3, as assessed by ELISA.

^^ A29>T (dominant hu CDR1 residue); 153 (CDR2 junction)>parental retained; N66, T68, G69 (CDR2 N-glycon)>D66, S68, E69; K72 (CDR2 junction)>Q72; M108, M115 (CDR3 sulfoxide risk)>M108 (preferred), L115

^^^ S123>L123 (correction to hu IGHJ4)

^^^^huFR2 back mutations to mouse FR2: R43->K43; A45->R45; Q48->K48

FIG. 8 provides VL (Kappa) protein sequences and the LCR-hu1901 CDR grafting outline for VK chains. The tabulated sequences are as follows: murine 1901 VL (Kappa) protein sequence (SEQ ID NO: 20), LCR1901_Glv1 (grafted onto huIgKV1-39*01 framework) (SEQ ID NO:21), LCR1901 VK_Glv1_03(F) (SEQ ID NO: 22) and LCR1901 VK_Glv1_05(H) (SEQ ID NO:23). X*=mouse residues maintained; #=back-mutation of human to original mouse. IMGT numbering utilized for amino acid residue sequence numbers.

^ Parental CDRs (in bold)/Vernier residues grafted onto IGKV1-39*01 framework regions; L124>V124 (correction to hu IGKJ4)

^^ FR2: K48>Q48; A49>549; FR3: 574>D74; 583>Y83; L89>F89; P96>A96; T101>V101; F99>V99 (not mouse; mouse=L)

^^^ FR3: 574>D74; 583>Y83; L89>F89; P96>A96; T101>V101; F99>V99 (not mouse; mouse=L)

FIG. 9 provides tabulation of V-region variable domain global germ line alignment homologies (IGKV elements; IMGT) ^ % positional identities (positional similarities); average of top 3 scoring functional alleles FIG. 10 provides the protein sequences of LCR_1901_VH_1G10m-VK_GLv1_03 (F) (1901-1C). The sequence comprises a VH heavy chain amino acid LCR_1901_VH_1G10m (SEQ ID NO:18) and a VL kappa light chain amino acid VK_Glv1_03(F) (SEQ ID NO: 22). CDRs are in bold. The constant region CH IgG4(S228P) sequence is shown (SEQ ID NO:24) and also the CK IGKC*01 (SEQ ID NO:25).

FIG. 11 provides the protein sequences of LCR1901_VH_1G10m-VK_GLv1_05 (H) (1901-1A). The sequence comprises a VH heavy chain amino acid LCR_1901_VH_1G10m_03(K) (SEQ ID NO:19) and a VL kappa light chain amino acid VK_Glv1_03(F) (SEQ ID NO: 22). CDRs are in bold. The constant region CH IgG4(S228P) sequence is shown (SEQ ID NO:24) and also the CK IGKC*01 (SEQ ID NO:25).

FIG. 12 provides the protein sequences of LCR1901_VH_1G10m_03 (K)-VK_GLv1_03 (F) (1901-1D). The sequence comprises a VH heavy chain amino acid LCR_1901_VH_1G10m (SEQ ID NO:18) and a VL kappa light chain amino acid VK_Glv1_05(H) (SEQ ID NO: 23). CDRs are in bold. The constant region CH IgG4(S228P) sequence is shown (SEQ ID NO:24) and also the CK IGKC*01 (SEQ ID NO:25).

FIG. 13 provides the protein sequences of LCR1901_VH_1G10m_03 (K)-VK_GLv1_05 (H) (1901-1B). The sequence comprises a VH heavy chain amino acid LCR_1901_VH_1G10m_03(K) (SEQ ID NO:19) and a VL kappa light chain amino acid VK_Glv1_05(H) (SEQ ID NO: 23). CDRs are in bold. The constant region CH IgG4(S228P) sequence is shown (SEQ ID NO:24) and also the CK IGKC*01 (SEQ ID NO:25).

FIG. 14 provides the predicted packing torsion angles (based on 568 PDB structures; PAPS, bioinf.org.uk/abs/paps/) The improved/re-acquired potency of the [K+F] GLv1 reversion mutant pairing is achieved despite a significantly different predicted VH/VK torsion angle from the murine parent. Both humanized VH and VK are predicted to contribute to the shift in angle. [K+F] predicts a subtle angle shift over the compromised GLv1 original graft—suggesting a possible explanation for the re-acquisition of neutralizing potency in the TMLEC assay. The minimally back-mutated pairing of VH_1G10m with the newly designed GLv1_05(H) kappa chain maintains the predicted [K+F] angle.

FIG. 15 depicts neutralization of TGFb3 induced luciferase expression in TMLEC by TGFb antibodies. Antibodies evaluated are the (A) 1901 parental, (B) 1901 1A (LCR1901_VH_1G10m-VK_GLv1_05 (H)), (C) 1901 1B (LCR1901_VH_1G10m_03 (K)-VK_GLv1_05 (H)), (D) 1901 1C (LCR_1901_VH_1G10m-VK_GLv1_03 (F)) and (E) 1901 1D (LCR1901_VH_1G10m_03 (K) VK_GLv1_03 (F)) antibodies.

Figure 16:
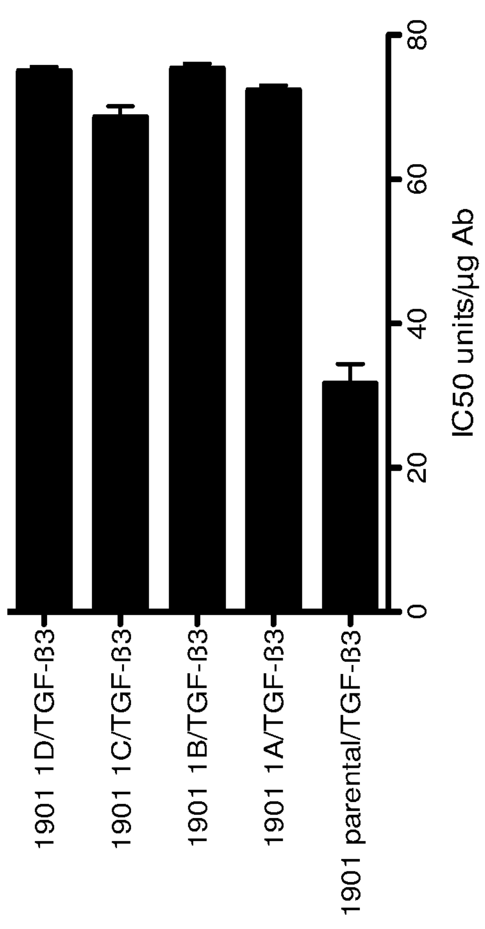

FIG. 16 provides inhibition of TGFb3 signaling in TMLEC assay (TGF-β3 inhibitory units per μg). The humanized LCR1901 IgG4 antibodies have improved functional neutralization compared to the parental murine 1901 antibody. Values are calculated from Ab concentration for 50% TGF-b3 (500 pg/ml) inhibition in TMLEC assay.

Figure 17:
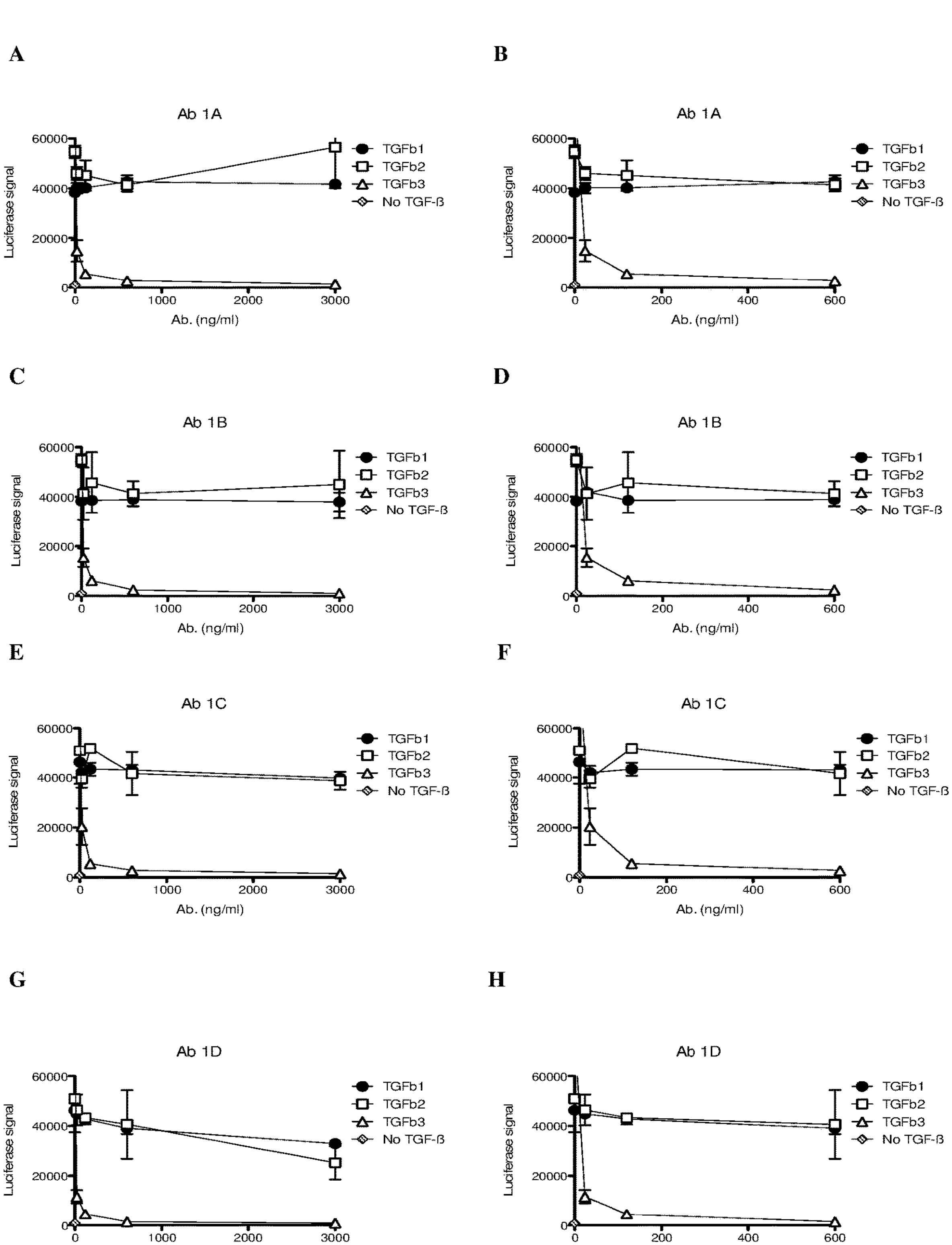

FIG. 17 depicts TGF-ß specificity of humanized 1901 constructs (A and B) 1901-A, (C and D) 1901-B, (E and F) 1901-C and (G and H) 1901D. The left set of panels (A, C, E and G) show higher concentration of antibody, while the right set of panels (B, D, F and H) depict a closer view of antibody concentrations up to 600 ng/ml.

FIG. 18 depicts competition ELISA binding curves of LCR1901 IgG4 variants 1A, 1B, 1C and 1D vs parental mouse 1901 antibody.

Figure 19:
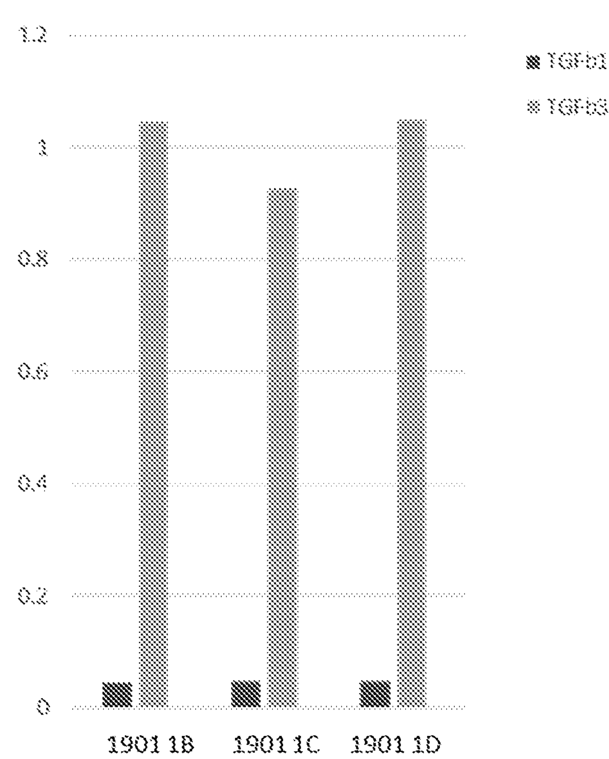

FIG. 19 depicts comparative ELISA Binding analysis of monovalent humanized 1901 candidate Fabs 1B, 1C and 1D against TGFb1 and TGFb3.

Figure 20:
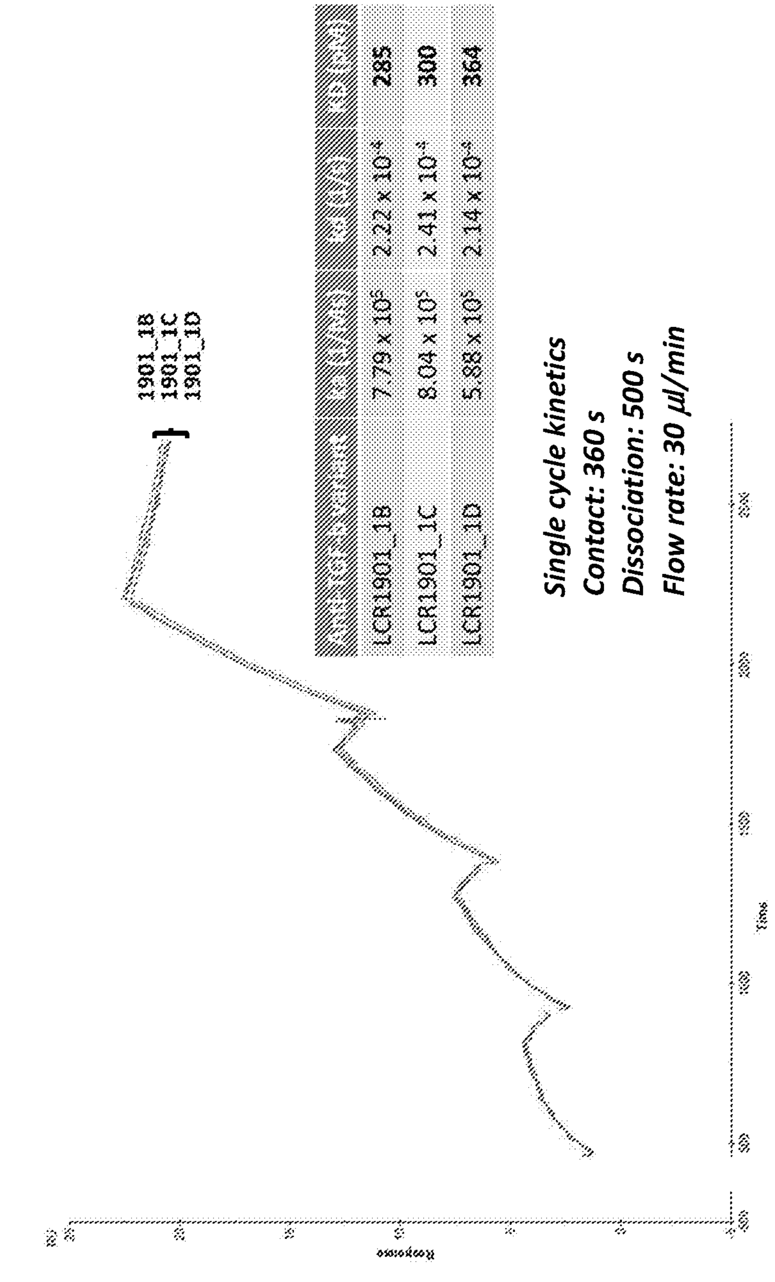

FIG. 20 provides representative Biacore single-cycle kinetic sensorgrams for monovalent humanized 1901 candidate Fabs versus benchmarks against immobilized TGFb3. TGFb3 immobilized directly; Fab as soluble analyte (0 2.5 nM). Single cycle kinetics were conducted as follows Contact: 360 s; Dissociation: 500 s; Flow rate: 30 μl/min.

Figures 21A, 21B:
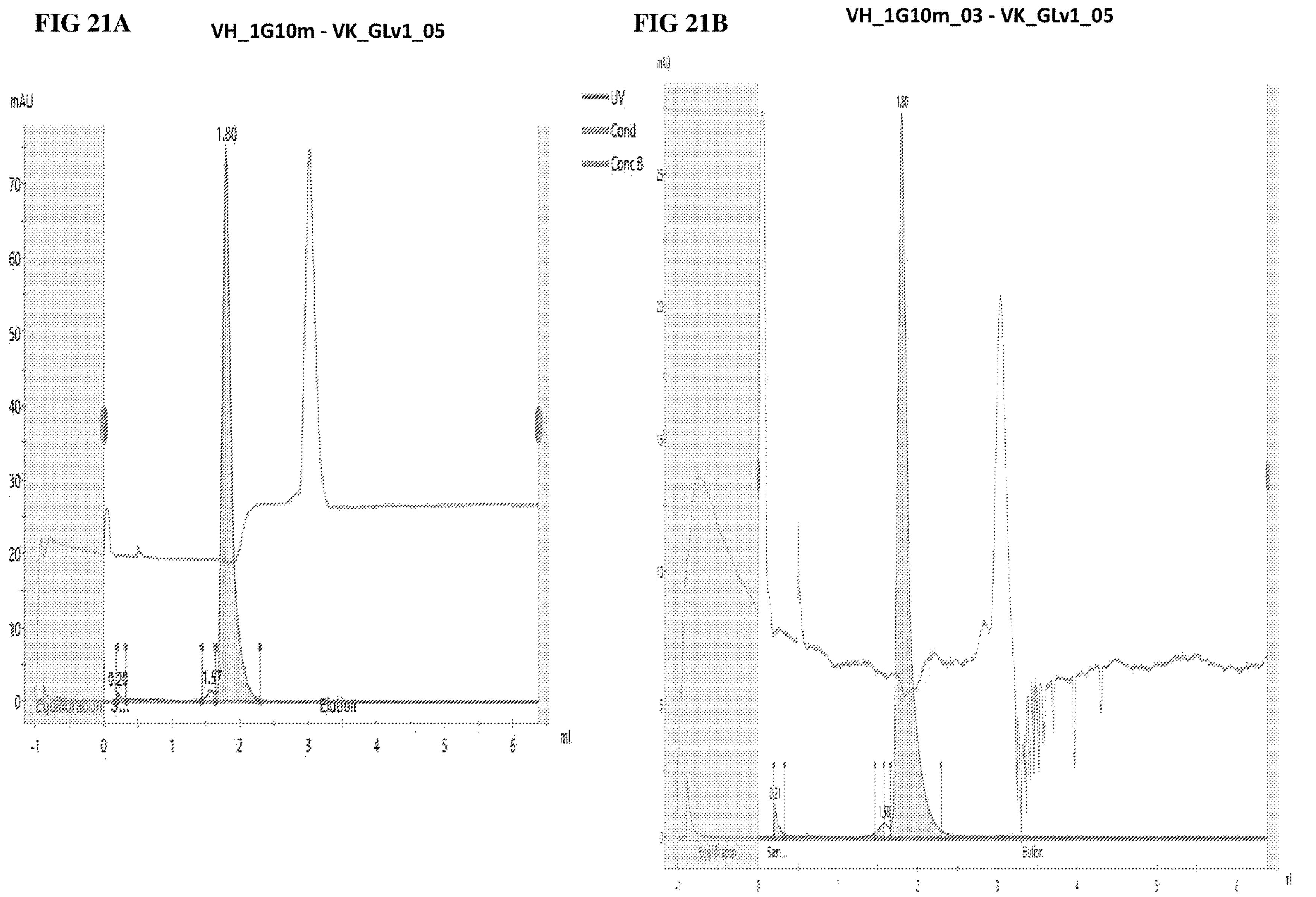
Figures 21C, 21D:
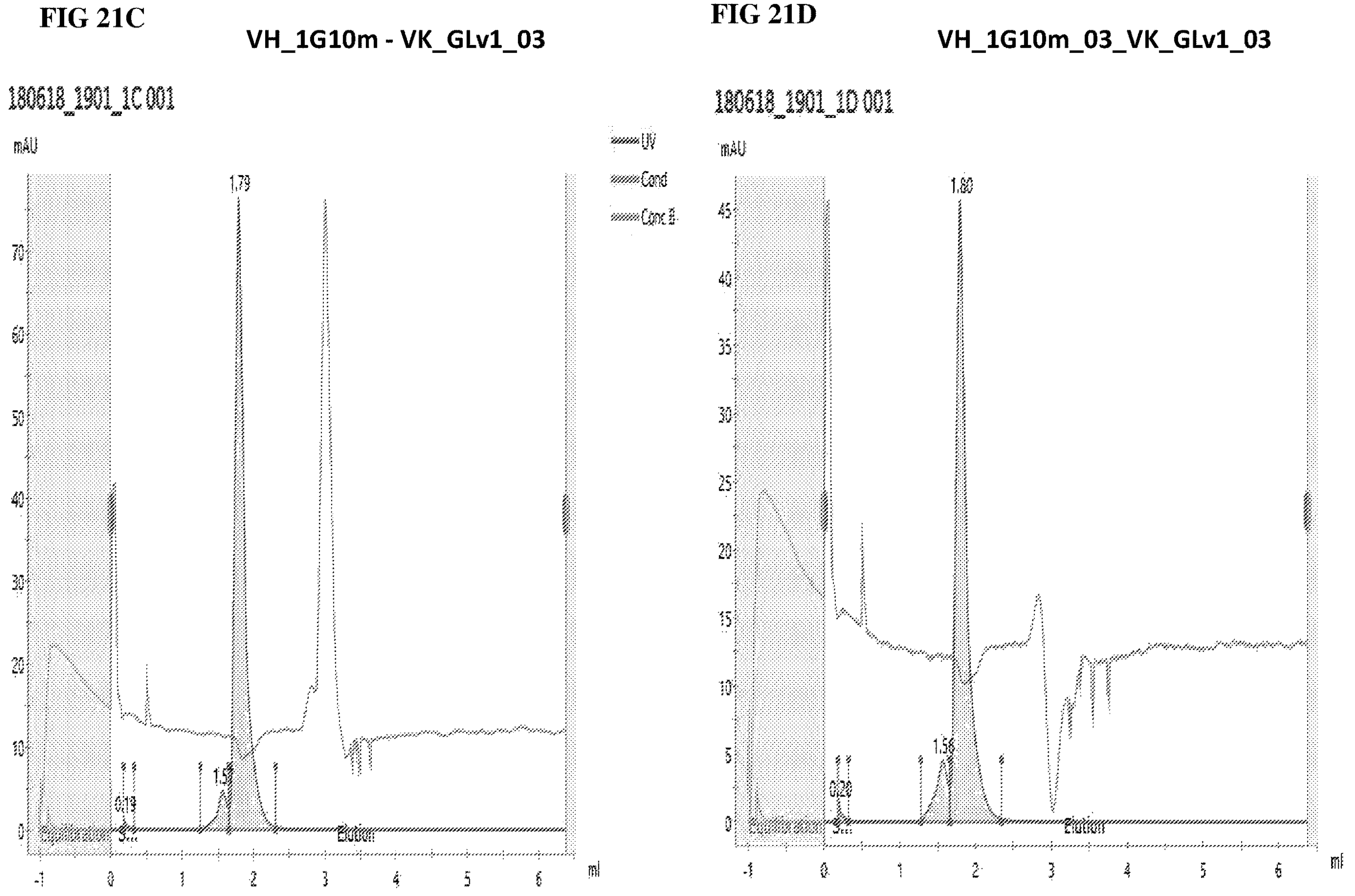

FIG. 21 provides SEC profiles for purified humanized 1901 candidate IgG4 antibodies (A) VH_1G10m-VK_Glv1_05 (1901-1A), (B) VH_1G10m_03-VK_Glv1_05 (1901-1B), (C) VH_1G10m-VK_Glv1_03 (1901-1C) and (D) VH_1G10m_03-VK_Glv1_03 (1901-1D).

Figures 22A, 22B:
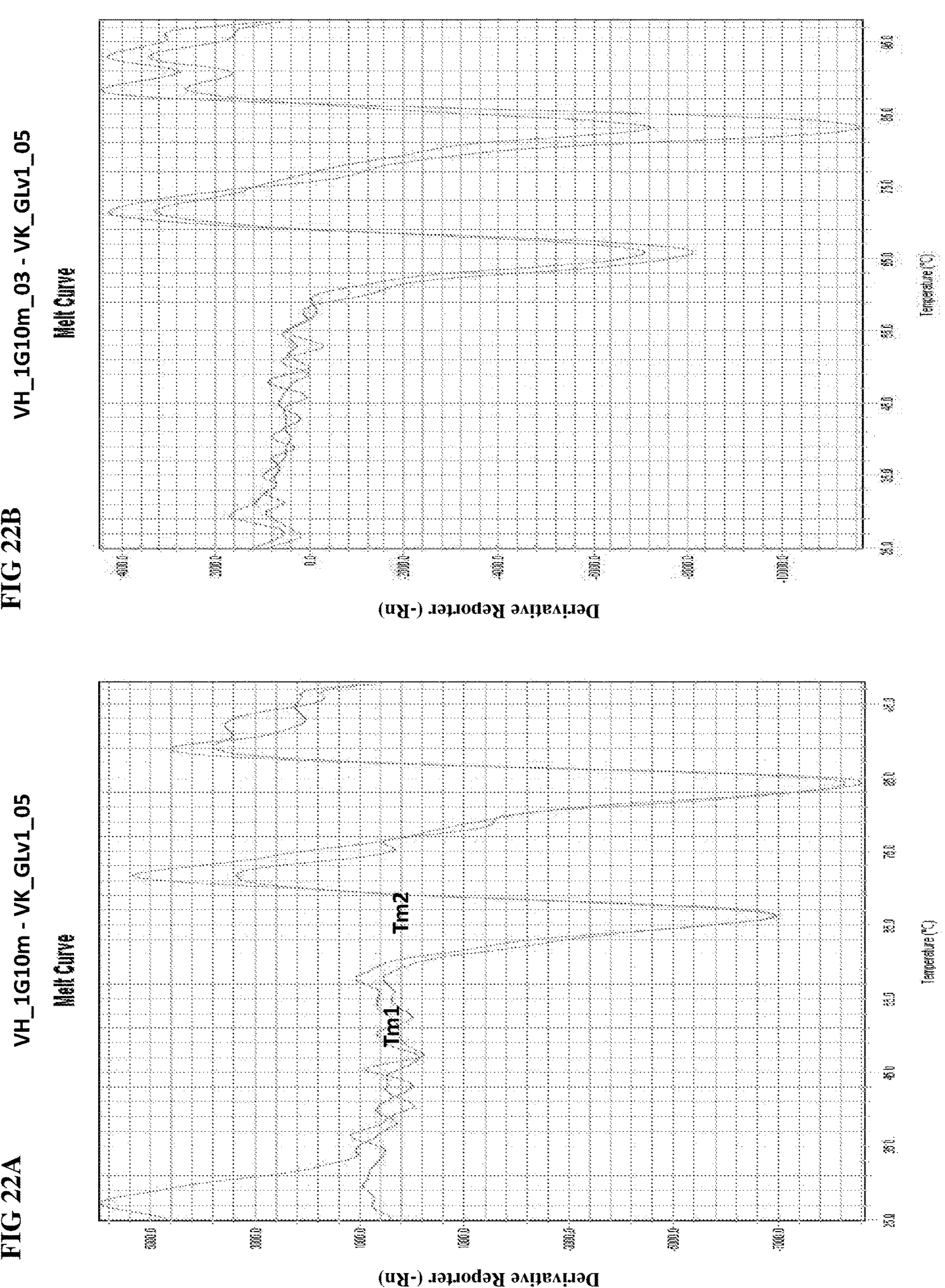
Figures 22C, 22D:
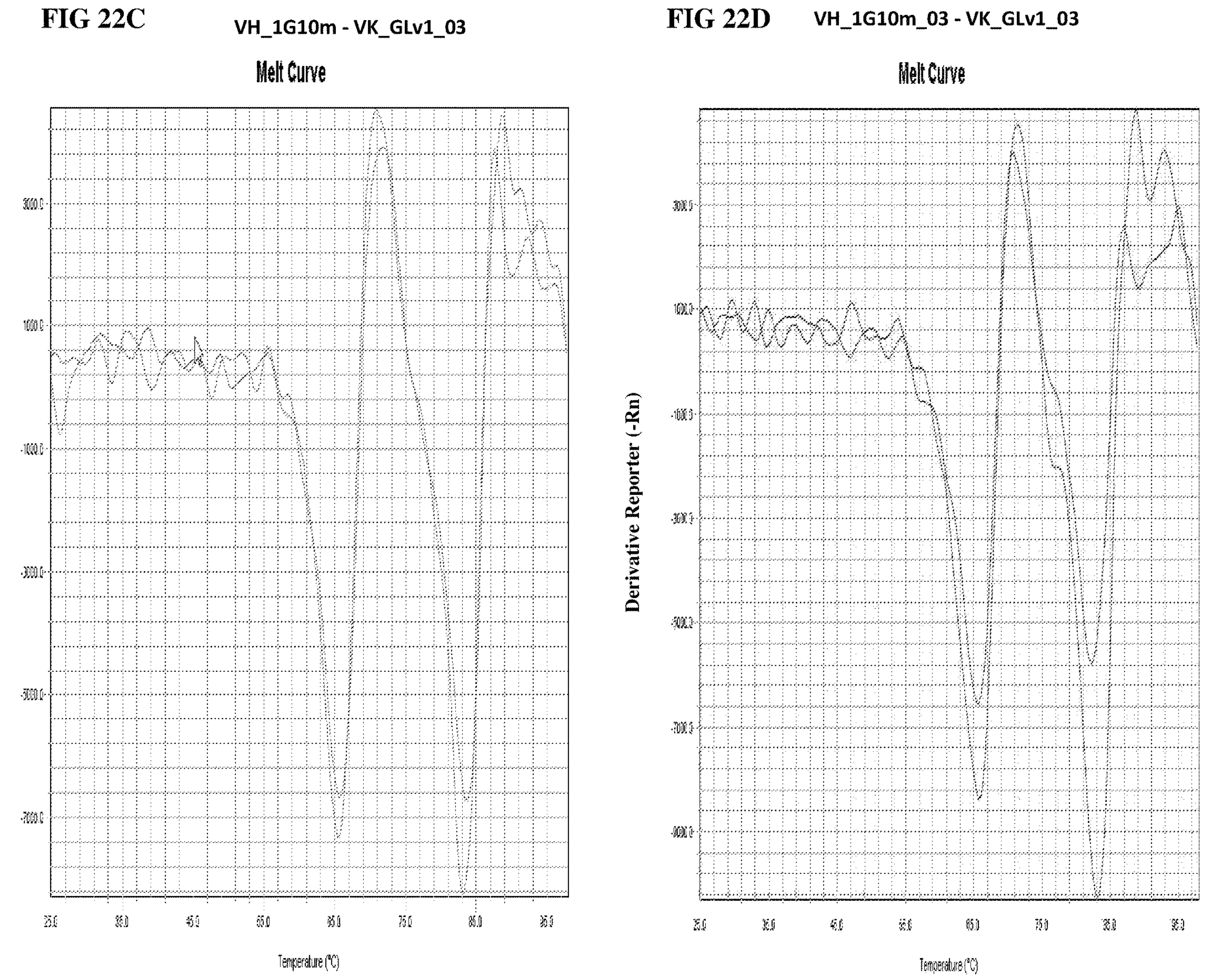

FIG. 22 shows representative DSF melting temperatures for purified humanized 1901 candidate IgG4 antibodies (A) VH_1G10m-VK_Glv1_05 (1901-1A), (B) VH_1G10m_03-VK_Glv1_05 (1901-1B), (C) VH_1G10m-VK_Glv1_03 (1901-1C) and (D) VH_1G10m_03-VK_Glv1_03 (1901-1D).

FIG. 23 tabulates DSF unfolding transitions and temperatures.

^ Fab transition overlapping with CH2 unfolding—no discrete Tm2.

Figure 24:
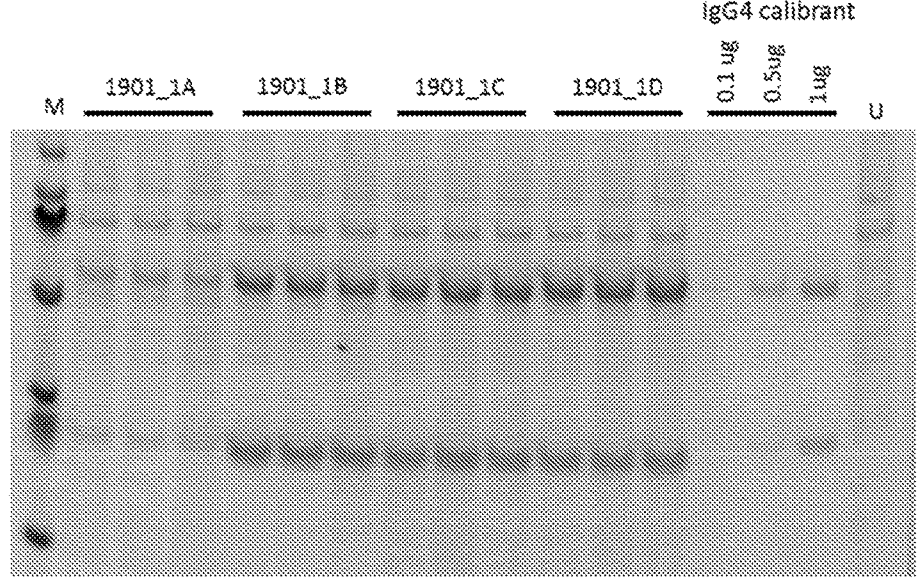

FIG. 24 provides (A) relative crude protein expression yields for humanized 1901 candidate IgG4 antibodies and (B) SDS-PAGE (denaturing) of the 1901 candidate antibodies 1a, 1B, 1C and 1D. 2 ml transfection cultures grown in triplicate; 10 μl supernatant loaded.

Figure 25:
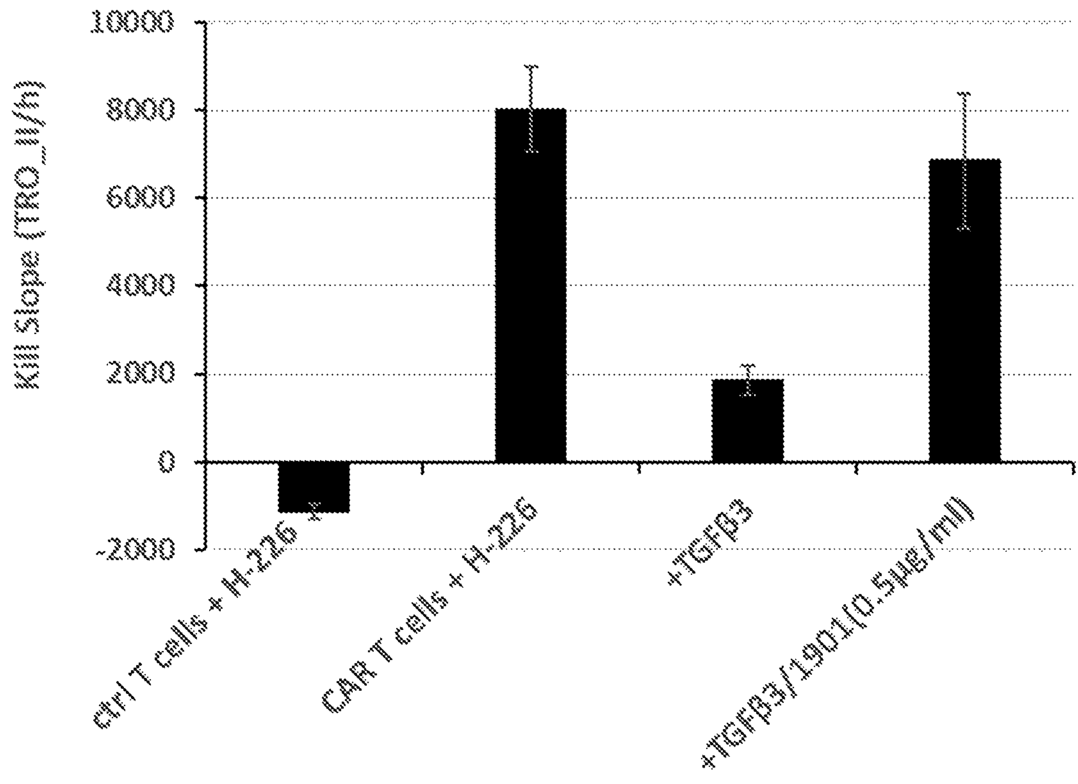

FIG. 25 depicts in vitro rescue of TGFb3-mediated inhibition of anti-MSLN CAR-T target cell killing by TGFb3 specific antibody mAb 1901-1B. Effector: Primary human T cells transfected with an anti-mesothelin CAR (hP4; US2014301993 A1). Target: H-226 human lung carcinoma (Meso++); E:T ratio 5:1 Additions: TGFb3 (1 ng/ml), 1901_1B TGFb3-selective huIgG4 Read-out: Incucyte: Cytotox Red accumulation by dead target cells (6-20 h kill slope; Total Red Image Integrated Intensity per Image).

Figure 26:
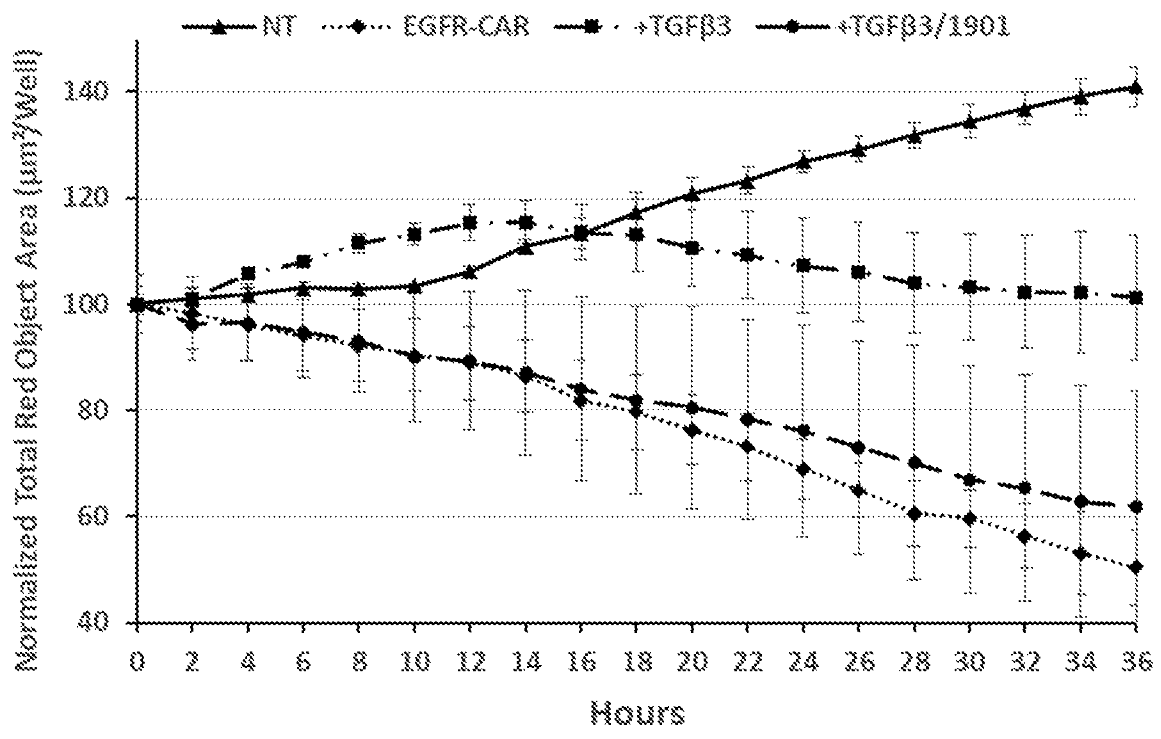

FIG. 26 depicts in vitro rescue of TGFb3-mediated inhibition of anti-EGFR CAR-T target cell killing by TGFb3 specific antibody mAb 1901-1B. Effector: Primary human T cells (CD3/CD28 activated & expanded PBMCs) transfected with an anti-EGFR CAR (reverse engineered scFv Panitumumab). Target: MDA-MB-231 human breast cancer (EGFR+); E:T ratio 5:1. Additions: TGFb3 (1 ng/ml), 1901_1B TGFb3-selective huIgG4 (500 ng/ml). Read-out: Incucyte: Time-dependent change in the numbers of pre-stained (CytolightRED) target cells.

Figure 27:
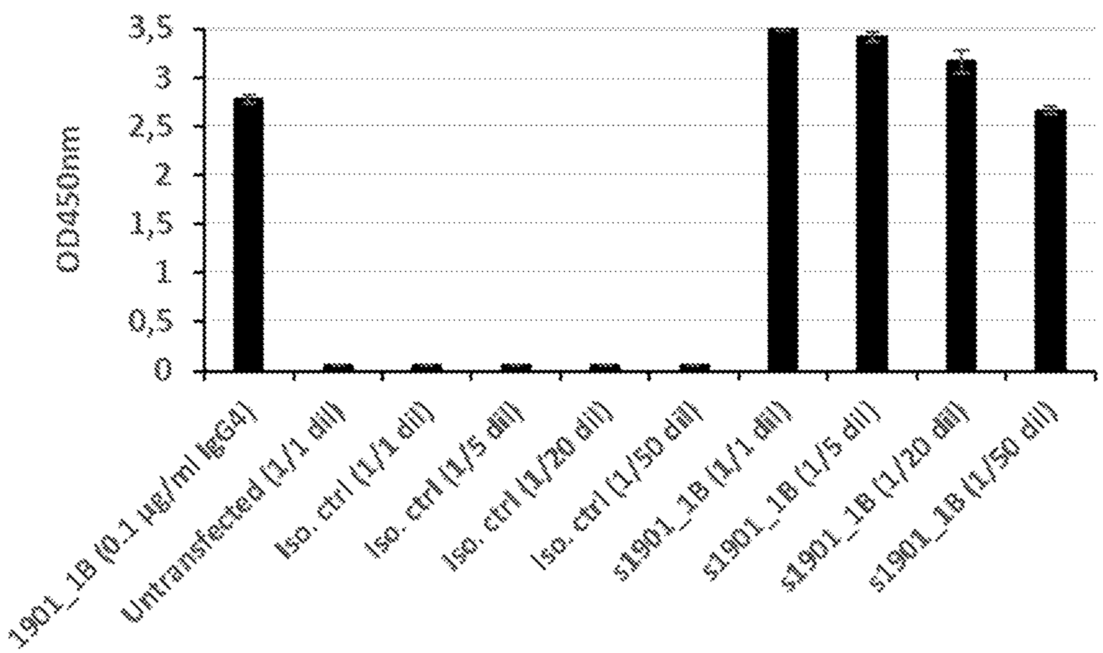

FIG. 27 depicts T cell-secreted 1901-1B antibody versus immobilized TGFβ3. Media supernatant from Jurkat T cell cultures expressing and secreting TGFβ3 antibody was evaluated for binding to TGFβ3. Iso ctrl is an isotype control antibody. 1901-1B antibody was added in one sample as a control for binding. Supernatants from the 1901-1B transfected T cells were added and also serially diluted up to 50 fold and demonstrated binding to immobilized TGFβ3 which was comparable to the added 1901-1B antibody control.

DETAILED DESCRIPTION

In accordance with the present invention there may be employed conventional molecular biology, microbiology, and recombinant DNA techniques within the skill of the art. Such techniques are explained fully in the literature. See, e.g., Sambrook et al, "Molecular Cloning: A Laboratory Manual" (1989); "Current Protocols in Molecular Biology" Volumes I-III [Ausubel, R. M., ed. (1994)]; "Cell Biology: A Laboratory Handbook" Volumes I-III [J. E. Celis, ed. (1994))]; "Current Protocols in Immunology" Volumes I-III [Coligan, J. E., ed. (1994)]; "Oligonucleotide Synthesis" (M. J. Gait ed. 1984); "Nucleic Acid Hybridization" [B. D. Hames & S. J. Higgins eds. (1985)]; "Transcription And Translation" [B. D. Hames & S. J. Higgins, eds. (1984)]; "Animal Cell Culture" [R. I. Freshney, ed. (1986)]; "Immobilized Cells And Enzymes" [IRL Press, (1986)]; B. Perbal, "A Practical Guide To Molecular Cloning" (1984).

Therefore, if appearing herein, the following terms shall have the definitions set out below.

A. Terminology

The term "TGF-ß3", "TGFb3" and "TGF-Beta3" refers to and includes both the human and the mouse protein, transforming growth factor beta isoform 3. Exemplary full length amino acid sequences of human and mouse TGF-β3 are provided herein.

The antibody "1901-1A" or "1A" is also denoted as LCR1901_VH_1G10m-LCR1901_VK_GLv1_05(H). Antibody 1901-1A comprises the heavy chain sequence of LCR1901_VH_1G10m (SEQ ID NO:18), and light chain sequence LCR1901_VK_GLv1_05(H) (SEQ ID NO:23)

The antibody "1901-1B" or "1B" is also denoted as LCR1901_VH_1G10m_03(K)-LCR1901_VK_GLv1_05 (H). Antibody 1901-1B comprises the heavy chain sequence of LCR1901_VH_1G10m_03(K) (SEQ ID NO:19), and light chain sequence LCR1901_VK_GLv1_05(H) (SEQ ID NO:23).

The antibody "1901-1C" or "1C" is also denoted as LCR1901_VH_1G10m-LCR1901_VK_GLv1_03(F) (1901-1C). Antibody 1901-1C comprises the heavy chain sequence of LCR1901_VH_1G10m (SEQ ID NO:18), and light chain sequence LCR1901_VK_GLv1_03(F) (SEQ ID NO:22).

The antibody "1901-1D" or "1D" is also denoted as LCR1901_VH_1G10m_03(K)-LCR1901_VK_GLv1_03 (F). Antibody 1901-1D comprises the heavy chain sequence of LCR1901_VH_1G10m_03(K) (SEQ ID NO:19), and light chain sequence LCR1901_VK_GLv1_03(F) (SEQ ID NO:22).

The term "specific binding member" describes a member of a pair of molecules which have binding specificity for one another. The members of a specific binding pair may be naturally derived or wholly or partially synthetically produced. One member of the pair of molecules has an area on its surface, or a cavity, which specifically binds to and is therefore complementary to a particular spatial and polar organisation of the other member of the pair of molecules. Thus the members of the pair have the property of binding specifically to each other. Examples of types of specific binding pairs are antigen-antibody, biotin-avidin, hormone-hormone receptor, receptor-ligand, enzyme-substrate. This application is concerned with antigen-antibody type reactions.

The term "antibody" describes an immunoglobulin whether natural or partly or wholly synthetically produced. The term also covers any polypeptide or protein having a binding domain which is, or is homologous to, an antibody binding domain. CDR grafted antibodies are also contemplated by this term. An "antibody" is any immunoglobulin, including antibodies and fragments thereof, that binds a specific epitope. The term encompasses polyclonal, monoclonal, and chimeric antibodies, the last mentioned described in further detail in U.S. Pat. Nos. 4,816,397 and 4,816,567. The term "antibody(ies)" includes a wild type immunoglobulin (Ig) molecule, generally comprising four full length polypeptide chains, two heavy (H) chains and two light (L) chains, or an equivalent Ig homologue thereof (e.g., a camelid nanobody, which comprises only a heavy chain); including full length functional mutants, variants, or derivatives thereof, which retain the essential epitope binding features of an Ig molecule, and including dual specific, bispecific, multispecific, and dual variable domain antibodies; Immunoglobulin molecules can be of any class (e.g., IgG, IgE, IgM, IgD, IgA, and IgY), or subclass (e.g., IgG1, IgG2, IgG3, IgG4, IgA1, and IgA2). Also included within the meaning of the term "antibody" are any "antibody fragment".

An "antibody fragment" means a molecule comprising at least one polypeptide chain that is not full length, including (i) a Fab fragment, which is a monovalent fragment consisting of the variable light (VL), variable heavy (VH), constant light (CL) and constant heavy 1 (CH1) domains; (ii) a F(ab')2 fragment, which is a bivalent fragment comprising two Fab fragments linked by a disulfide bridge at the hinge region; (iii) a heavy chain portion of an Fab (Fd) fragment, which consists of the VH and CH1 domains; (iv) a variable fragment (Fv), which consists of the VL and VH domains of a single arm of an antibody, (v) a domain antibody (dAb) fragment, which comprises a single variable domain (Ward, E. S. et al., Nature 341, 544-546 (1989)); (vi) a camelid antibody; (vii) an isolated complementarity determining region (CDR); (viii) a Single Chain Fv Fragment wherein a VH domain and a VL domain are linked by a peptide linker which allows the two domains to associate to form an antigen binding site (Bird et al, Science, 242, 423-426, 1988; Huston et al, PNAS USA, 85, 5879-5883, 1988); (ix) a diabody, which is a bivalent, bispecific antibody in which VH and VL domains are expressed on a single polypeptide chain, but using a linker that is too short to allow for pairing between the two domains on the same chain, thereby forcing the domains to pair with the complementarity domains of another chain and creating two antigen binding sites (WO94/13804; P. Holliger et al Proc. Natl. Acad. Sci. USA 90 6444-6448, (1993)); and (x) a linear antibody, which comprises a pair of tandem Fv segments (VH-CH1-VH-CH1) which, together with complementarity light chain polypeptides, form a pair of antigen binding regions; (xi) multivalent antibody fragments (scFv dimers, trimers and/or tetramers (Power and Hudson, J Immunol. Methods 242: 193-204 9 (2000)); (xii) a minibody, which is a bivalent molecule comprised of scFv fused to constant immunoglobulin domains, CH3 or CH4, wherein the constant CH3 or CH4 domains serve as dimerization domains (Olafsen T et al (2004) Prot Eng Des Sel 17(4):315-323; Hollinger P and Hudson P J (2005) Nature Biotech 23(9): 1126-1136); and (xiii) other non-full length portions of heavy and/or light chains, or mutants, variants, or derivatives thereof, alone or in any combination.

As antibodies can be modified in a number of ways, the term "antibody" should be construed as covering any specific binding member or substance having a binding domain with the required specificity. Thus, this term covers antibody fragments, derivatives, functional equivalents and homologues of antibodies, including any polypeptide comprising an immunoglobulin binding domain, whether natural or wholly or partially synthetic. Chimeric molecules comprising an immunoglobulin binding domain, or equivalent, fused to another polypeptide are therefore included. Cloning and expression of chimeric antibodies are described in EP-A-0120694 and EP-A-0125023 and U.S. Pat. Nos. 4,816,397 and 4,816,567.

An "antibody combining site" is that structural portion of an antibody molecule comprised of light chain or heavy and light chain variable and hypervariable regions that specifically binds antigen.

The phrase "antibody molecule" in its various grammatical forms as used herein contemplates both an intact immunoglobulin molecule and an immunologically active portion of an immunoglobulin molecule.

Exemplary antibody molecules are intact immunoglobulin molecules, substantially intact immunoglobulin molecules and those portions of an immunoglobulin molecule that contains the paratope, including those portions known in the art as Fab, Fab', $F(ab')_2$ and F(v), which portions are preferred for use in the therapeutic methods described herein.

Antibodies may also be bispecific, wherein one binding domain of the antibody is a specific binding member of the invention, and the other binding domain has a different specificity, e.g. to recruit an effector function or the like. Bispecific antibodies of the present invention include wherein one binding domain of the antibody is a specific binding member of the present invention, including a fragment thereof, and the other binding domain is a distinct antibody or fragment thereof, including that of a distinct anti-cancer or anti-tumor specific antibody. The other binding domain may be an antibody that recognizes or targets a particular cell type, as in a neural or glial cell-specific antibody. In the bispecific antibodies of the present invention the one binding domain of the antibody of the invention may be combined with other binding domains or molecules which recognize particular cell receptors and/or modulate cells in a particular fashion, as for instance an immune modulator (e.g., interleukin(s)), a growth modulator or cytokine or a toxin (e.g., ricin) or anti-mitotic or apoptotic agent or factor. Thus, the TGFbeta-3 antibodies of the invention may be utilized to direct or target agents, labels, other molecules or compounds or antibodies in indications such as wound healing, inflammation, cancer or tumors.

The phrase "monoclonal antibody" in its various grammatical forms refers to an antibody having only one species of antibody combining site capable of immunoreacting with a particular antigen. A monoclonal antibody thus typically displays a single binding affinity for any antigen with which it immunoreacts. A monoclonal antibody may also contain an antibody molecule having a plurality of antibody combining sites, each immunospecific for a different antigen; e.g., a bispecific (chimeric) monoclonal antibody.

The term "antigen binding domain" describes the part of an antibody which comprises the area which specifically binds to and is complementary to part or all of an antigen. Where an antigen is large, an antibody may bind to a particular part of the antigen only, which part is termed an epitope. An antigen binding domain may be provided by one or more antibody variable domains. Preferably, an antigen binding domain comprises an antibody light chain variable region (VL) and an antibody heavy chain variable region (VH).

Immunoconjugates or antibody fusion proteins of the present invention, wherein the antibodies, antibody molecules, or fragments thereof, of use in the present invention are conjugated or attached to other molecules or agents further include, but are not limited to such antibodies, molecules, or fragments conjugated to a chemical ablation agent, toxin, immunomodulator, cytokine, cytotoxic agent, chemotherapeutic agent, antimicrobial agent or peptide, cell wall and/or cell membrane disrupter, or drug.

The term "adjuvant(s)" describes a substance, compound, agent or material useful for improving an immune response or immune cell or component stimulation, and may in some instances be combined with any particular antigen in an immunological, pharmaceutical or vaccine composition. Adjuvants can be used to increase the amount of antibody and effector T cells produced and to reduce the quantity of antigen or immune stimulant or modulator and the frequency of injection. Although some antigens are administered without an adjuvant, there are many antigens that lack sufficient immunogenicity to stimulate a useful immune response in the absence of an effective adjuvant. Adjuvants also improve the immune response from "self-sufficient" antigens, in that the immune response obtained may be increased or the amount of antigen administered may be reduced. An adjuvant can serve as a tissue depot that slowly releases the antigen and also as a lymphoid system activator that non-specifically enhances the immune response (Hood et al., *Immunology, Second Ed.,* 1984, Benjamin/Cummings: Menlo Park, California, p. 384). In a preferred aspect an adjuvant is physiologically and/or pharmaceutically acceptable in a mammal, particularly a human. The standard adjuvant for use in laboratory animals is Freund's adjuvant. Freund's Complete adjuvant (FCA) is an emulsion containing mineral oil and killed mycobacteria in saline. Freund's incomplete adjuvant (FIA) omits the mycobacteria. Both FIA and FCA induce good humoral (antibody) immunity, and FCA additionally induces high levels of cell-mediated immunity. However, neither FCA nor FIA are acceptable for clinical use due to the side effects. In particular, mineral oil is known to cause granulomas and abscesses, and Mycobacterium tuberculosis is the agent responsible for tuberculosis. Previously known and utilized adjuvants include, but are not limited to, complete Freund's adjuvant, incomplete Freund's adjuvant, saponin, mineral gels such as aluminum hydroxide, surface active substances such as lysolecithin, pluronic polyols, polyanions, peptides, oil or hydrocarbon emulsions, keyhole limpet hemocyanins, dinitrophenol, and potentially useful human adjuvant such as BCG (bacille Calmette-Guerin) and *Corynebacterium parvum*. Mineral salt adjuvants include but are not limited to: aluminum hydroxide, aluminum phosphate, calcium phosphate, zinc hydroxide and calcium hydroxide. Preferably, the adjuvant composition further comprises a lipid of fat emulsion comprising about 10% (by weight) vegetable oil and about 1-2% (by weight) phospholipids. Preferably, the adjuvant composition further optionally comprises an emulsion form having oily particles dispersed in a continuous aqueous phase, having an emulsion forming polyol in an amount of from about 0.2% (by weight) to about 49% (by weight), optionally a metabolizable oil in an emulsion-forming amount of up to 15% (by weight), and optionally a glycol ether-based surfactant in an emulsion-stabilizing amount of up to about 5% (by weight). There have been many substances that have been tried to be used as adjuvants, such as the lipid-A portion of gram negative bacterial endotoxin, and trehalose dimycolate of mycobacteria. The phospholipid lysolecithin exhibited adjuvant activity (Arnold et al., Eur. J Immunol. 9:363-366, 1979). Some synthetic surfactants exhibited adjuvant activity, including dimethyldioctadecyl ammonium bromide (DDA) and certain linear polyoxypropylenepolyoxyethylene (POP-POE) block polymers (Snippe et al., Int. Arch. Allergy Appl. Immunol. 65:390-398, 1981; and Hunter et al., J. Immunol. 127:1244-1250, 1981).

The term "specific" may be used to refer to the situation in which one member of a specific binding pair will not show any significant binding to molecules other than its specific binding partner(s). The term is also applicable where e.g. an antigen binding domain is specific for a particular epitope which is carried by a number of antigens, in which case the specific binding member carrying the antigen binding domain will be able to bind to the various antigens carrying the epitope.

The term "comprise" is generally used in the sense of include, that is to say permitting the presence of one or more features or components.

The term "consisting essentially of" refers to a product, particularly a peptide sequence, of a defined number of residues which is not covalently attached to a larger product. In the case of the peptide of the invention referred to above, those of skill in the art will appreciate that minor modifications to the N- or C-terminal of the peptide may however be contemplated, such as the chemical modification of the terminal to add a protecting group or the like, e.g. the amidation of the C-terminus.

The term "isolated" refers to the state in which specific binding members of the invention, or nucleic acid encoding such binding members will be, in accordance with the present invention. Members and nucleic acid will be free or substantially free of material with which they are naturally associated such as other polypeptides or nucleic acids with which they are found in their natural environment, or the environment in which they are prepared (e.g. cell culture) when such preparation is by recombinant DNA technology practised in vitro or in vivo. Members and nucleic acid may be formulated with diluents or adjuvants and still for practical purposes be isolated—for example the members will normally be mixed with gelatin or other carriers if used to coat microtitre plates for use in immunoassays, or will be mixed with pharmaceutically acceptable carriers or diluents when used in diagnosis or therapy.

As used herein, "pg" means picogram, "ng" means nanogram, "ug" or "μg" mean microgram, "mg" means milligram, "ul" or "μl" mean microliter, "ml" means milliliter, "l" means liter.

The terms "antibody", "anti-TGFβ3 antibody", "TGF-beta3 antibody", "TGF-β3 antibody", "humanized TGFβ3 antibody", "TGFb3 antibody" and any variants not specifically listed, may be used herein interchangeably, and as used throughout the present application and claims refer to proteinaceous material including single or multiple proteins, and extends to those proteins having the amino acid sequence data described herein and presented in FIGS. 7, 8, 10, 11, 12 and 13 and the profile of activities set forth herein and in the Claims. Exemplary such TGFβ3 antibodies provided herein include antibodies 1901-1A, 1901-1B, 1901-1C and 1901-1D as provided and characterized herein. Antibodies provided herein extend to antibodies or proteins, including antibody fragments, having the amino acid sequence data described herein and presented in FIGS. 7, 8, 10, 11, 12 and 13, including CDR sequences SEQ ID NOs:1, 34, 35, 28-30 and 4, 5, 6, 31-33 and including variable region heavy chain sequences SEQ ID NOs: 18 and 19 and 36 and variable region light chain sequences SEQ ID NOs: 22 and 23, and the profile of activities set forth herein and in the Claims. Accordingly, proteins displaying substantially equivalent or altered activity are likewise contemplated. These modifications may be deliberate, for example, such as modifications obtained through site-directed mutagenesis, or may be accidental, such as those obtained through mutations in hosts that are producers of the complex or its named subunits. Also, the terms "antibody", "anti-TGFβ3 antibody", "TGFbeta3 antibody", "TGF-β3 antibody", "humanized TGFβ3 antibody", and the exemplary antibodies 1901-1A, 1901-1B, 1901-1C and 1901-1D are intended to include within their scope proteins specifically recited herein as well as all substantially homologous analogs and allelic variations.

In an aspect of the invention and particularly provided herein are antibodies which are specific to the TGF-beta isoform TGF-β3. In a particular aspect, the antibodies of the invention are humanized, including wherein antibodies have been modified to increase their similarity to antibody variants produced naturally in humans. Such specific TGF-β3 antibodies bind and recognize TGF-β3 isoform, and do not, or do not significantly, bind or recognize alternative TGF-β isoforms, particularly TGF-β1 and TGF-β2. TGF-β3 specific antibodies of the invention are exemplified by antibodies 1901-1A, 1901-1B, 1901-1C and 1901-1D.

The amino acid residues described herein are preferred to be in the "L" isomeric form. However, residues in the "D" isomeric form can be substituted for any L-amino acid residue, as long as the desired functional property of immunoglobulin-binding is retained by the polypeptide. $NH_2$ refers to the free amino group present at the amino terminus of a polypeptide. COOH refers to the free carboxy group present at the carboxy terminus of a polypeptide. In keeping with standard polypeptide nomenclature, *J. Biol. Chem.*, 243:3552-59 (1969), abbreviations for amino acid residues are shown in the following Table of Correspondence:

TABLE OF CORRESPONDENCE

| SYMBOL | | |
|---|---|---|
| 1-Letter | 3-Letter | AMINO ACID |
| Y | Tyr | tyrosine |
| G | Gly | glycine |
| F | Phe | phenylalanine |
| M | Met | methionine |
| A | Ala | alanine |
| S | Ser | serine |
| I | Ile | isoleucine |
| L | Leu | leucine |
| T | Thr | threonine |
| V | Val | valine |
| P | Pro | proline |
| K | Lys | lysine |
| H | His | histidine |
| Q | Gln | glutamine |
| E | Glu | glutamic acid |
| W | Trp | tryptophan |
| R | Arg | arginine |
| D | Asp | aspartic acid |
| N | Asn | asparagine |
| C | Cys | cysteine |

It should be noted that all amino-acid residue sequences are represented herein by formulae whose left and right orientation is in the conventional direction of amino-terminus to carboxy-terminus. Furthermore, it should be noted that a dash at the beginning or end of an amino acid residue sequence indicates a peptide bond to a further sequence of one or more amino-acid residues. The above Table is presented to correlate the three-letter and one-letter notations which may appear alternately herein.

A "replicon" is any genetic element (e.g., plasmid, chromosome, virus) that functions as an autonomous unit of DNA replication in vivo; i.e., capable of replication under its own control.

A "vector" is a replicon, such as plasmid, phage or cosmid, to which another DNA segment may be attached so as to bring about the replication of the attached segment.

A "DNA molecule" refers to the polymeric form of deoxyribonucleotides (adenine, guanine, thymine, or cytosine) in its either single stranded form, or a double-stranded helix. This term refers only to the primary and secondary structure of the molecule, and does not limit it to any particular tertiary forms. Thus, this term includes double-stranded DNA found, inter alia, in linear DNA molecules (e.g., restriction fragments), viruses, plasmids, and chromosomes. In discussing the structure of particular double-stranded DNA molecules, sequences may be described herein according to the normal convention of giving only the sequence in the 5' to 3' direction along the nontranscribed strand of DNA (i.e., the strand having a sequence homologous to the mRNA).

An "origin of replication" refers to those DNA sequences that participate in DNA synthesis.

A DNA "coding sequence" is a double-stranded DNA sequence which is transcribed and translated into a polypeptide in vivo when placed under the control of appropriate regulatory sequences. The boundaries of the coding sequence are determined by a start codon at the 5' (amino) terminus and a translation stop codon at the 3' (carboxyl) terminus. A coding sequence can include, but is not limited to, prokaryotic sequences, cDNA from eukaryotic mRNA, genomic DNA sequences from eukaryotic (e.g., mammalian) DNA, and even synthetic DNA sequences. A polyadenylation signal and transcription termination sequence will usually be located 3' to the coding sequence.

Transcriptional and translational control sequences are DNA regulatory sequences, such as promoters, enhancers, polyadenylation signals, terminators, and the like, that provide for the expression of a coding sequence in a host cell.

A "promoter sequence" is a DNA regulatory region capable of binding RNA polymerase in a cell and initiating transcription of a downstream (3' direction) coding sequence. For purposes of defining the present invention, the promoter sequence is bounded at its 3' terminus by the transcription initiation site and extends upstream (5' direction) to include the minimum number of bases or elements necessary to initiate transcription at levels detectable above background. Within the promoter sequence will be found a transcription initiation site (conveniently defined by mapping with nuclease S1), as well as protein binding domains (consensus sequences) responsible for the binding of RNA polymerase. Eukaryotic promoters will often, but not always, contain "TATA" boxes and "CAT" boxes. Prokaryotic promoters contain Shine-Dalgarno sequences in addition to the −10 and −35 consensus sequences.

An "expression control sequence" is a DNA sequence that controls and regulates the transcription and translation of another DNA sequence. A coding sequence is "under the control" of transcriptional and translational control sequences in a cell when RNA polymerase transcribes the coding sequence into mRNA, which is then translated into the protein encoded by the coding sequence.

A "signal sequence" can be included before the coding sequence. This sequence encodes a signal peptide, N-terminal to the polypeptide, that communicates to the host cell to direct the polypeptide to the cell surface or secrete the polypeptide into the media, and this signal peptide is clipped off by the host cell before the protein leaves the cell. Signal sequences can be found associated with a variety of proteins native to prokaryotes and eukaryotes.

The term "oligonucleotide," as used herein in referring to the probe of the present invention, is defined as a molecule comprised of two or more ribonucleotides, preferably more than three. Its exact size will depend upon many factors which, in turn, depend upon the ultimate function and use of the oligonucleotide.

The term "primer" as used herein refers to an oligonucleotide, whether occurring naturally as in a purified restriction digest or produced synthetically, which is capable of acting as a point of initiation of synthesis when placed under conditions in which synthesis of a primer extension product, which is complementary to a nucleic acid strand, is induced, i.e., in the presence of nucleotides and an inducing agent such as a DNA polymerase and at a suitable temperature and pH. The primer may be either single-stranded or double-stranded and must be sufficiently long to prime the synthesis of the desired extension product in the presence of the inducing agent. The exact length of the primer will depend upon many factors, including temperature, source of primer and use of the method. For example, for diagnostic applications, depending on the complexity of the target sequence, the oligonucleotide primer typically contains 15-25 or more nucleotides, although it may contain fewer nucleotides.

The primers herein are selected to be "substantially" complementary to different strands of a particular target DNA sequence. This means that the primers must be sufficiently complementary to hybridize with their respective strands. Therefore, the primer sequence need not reflect the exact sequence of the template. For example, a non-complementary nucleotide fragment may be attached to the 5' end of the primer, with the remainder of the primer sequence being complementary to the strand. Alternatively, non-complementary bases or longer sequences can be interspersed into the primer, provided that the primer sequence has sufficient complementarity with the sequence of the strand to hybridize therewith and thereby form the template for the synthesis of the extension product.

As used herein, the terms "restriction endonucleases" and "restriction enzymes" refer to bacterial enzymes, each of which cut double-stranded DNA at or near a specific nucleotide sequence.

A cell has been "transformed" by exogenous or heterologous DNA when such DNA has been introduced inside the cell. The transforming DNA may or may not be integrated (covalently linked) into chromosomal DNA making up the genome of the cell. In prokaryotes, yeast, and mammalian cells for example, the transforming DNA may be maintained on an episomal element such as a plasmid. With respect to eukaryotic cells, a stably transformed cell is one in which the transforming DNA has become integrated into a chromosome so that it is inherited by daughter cells through chromosome replication. This stability is demonstrated by the ability of the eukaryotic cell to establish cell lines or clones comprised of a population of daughter cells containing the transforming DNA. A "clone" is a population of cells derived from a single cell or common ancestor by mitosis. A "cell line" is a clone of a primary cell that is capable of stable growth in vitro for many generations.

Two DNA sequences are "substantially homologous" when at least about 75% (preferably at least about 80%, and most preferably at least about 90 or 95%) of the nucleotides match over the defined length of the DNA sequences. Sequences that are substantially homologous can be identified by comparing the sequences using standard software available in sequence data banks, or in a Southern hybridization experiment under, for example, stringent conditions as defined for that particular system. Defining appropriate hybridization conditions is within the skill of the art.

It should be appreciated that also within the scope of the present invention are DNA sequences encoding specific binding members (antibodies) of the invention which code for e.g. an antibody having amino acid sequence as provided in FIG. 10, 11, 12 or 13, or comprising the CDR domain region sequences set out herein or in FIG. 7, 8, 10, 11, 12 or 13, but which are degenerate thereto. By "degenerate to" is meant that a different three-letter codon is used to specify a particular amino acid. It is well known in the art that the following codons can be used interchangeably to code for each specific amino acid:

| | |
|---|---|
| Phenylalanine (Phe or F) | UUU or UUC |
| Leucine (Leu or L) | UUA or UUG or CUU or CUC or CUA or CUG |
| Isoleucine (Ile or I) | AUU or AUC or AUA |
| Methionine (Met or M) | AUG |
| Valine (Val or V) | GUU or GUC of GUA or GUG |
| Serine (Ser or S) | UCU or UCC or UCA or UCG or AGU or AGC |
| Proline (Pro or P) | CCU or CCC or CCA or CCG |
| Threonine (Thr or T) | ACU or ACC or ACA or ACG |
| Alanine (Ala or A) | GCU or GCG or GCA or GCG |
| Tyrosine (Tyr or Y) | UAU or UAC |
| Histidine (His or H) | CAU or CAC |
| Glutamine (Gln or Q) | CAA or CAG |
| Asparagine (Asn or N) | AAU or AAC |
| Lysine (Lys or K) | AAA or AAG |
| Aspartic Acid (Asp or D) | GAU or GAC |
| Glutamic Acid (Glu or E) | GAA or GAG |
| Cysteine (Cys or C) | UGU or UGC |
| Arginine (Arg or R) | CGU or CGC or CGA or CGG or AGA or AGG |
| Glycine (Gly or G) | GGU or GGC or GGA or GGG |
| Tryptophan (Trp or W) | UGG |
| Termination codon | UAA (ochre) or UAG (amber) or UGA (opal) |

It should be understood that the codons specified above are for RNA sequences. The corresponding codons for DNA have a T substituted for U.

Mutations can be made in the sequences encoding the amino acids, antibody fragments, CDR region sequences set out in FIGS. 7, 8, 10, 11, 12 and/or 13, particularly CDR sequences heavy chain CDRs SEQ ID NOs: 1, 34, 35, 30, 28 29 and/or light chain CDRs SEQ ID NOs: 4, 5, 6, 33, 31, 32, such that a particular codon is changed to a codon which codes for a different amino acid. Such a mutation is generally made by making the fewest nucleotide changes possible. A substitution mutation of this sort can be made to change an amino acid in the resulting protein in a non-conservative manner (for example, by changing the codon from an amino acid belonging to a grouping of amino acids having a particular size or characteristic to an amino acid belonging to another grouping) or in a conservative manner (for example, by changing the codon from an amino acid belonging to a grouping of amino acids having a particular size or characteristic to an amino acid belonging to the same grouping). Such a conservative change generally leads to less change in the structure and function of the resulting protein. A non-conservative change is more likely to alter the structure, activity or function of the resulting protein. The present invention includes sequences containing amino acid changes and substitutions, including conservative changes, which do not significantly alter the activity or binding characteristics of the resulting protein.

The following is one example of various groupings of amino acids:

Amino Acids with Nonpolar R Groups

Alanine, Valine, Leucine, Isoleucine, Proline, Phenylalanine, Tryptophan, Methionine Amino Acids with Uncharged Polar R Groups Glycine, Serine, Threonine, Cysteine, Tyrosine, Asparagine, Glutamine Amino Acids with Charged Polar R Groups (Negatively Charged at pH 6.0)

Aspartic acid, Glutamic acid

Basic Amino Acids (Positively Charged at pH 6.0)

Lysine, Arginine, Histidine (at pH 6.0)

Another grouping may be those amino acids with phenyl groups: Phenylalanine, Tryptophan, Tyrosine Another grouping may be according to molecular weight (i.e., size of R groups):

| | | | |
|---|---|---|---|
| Glycine | 75 | Alanine | 89 |
| Serine | 105 | Proline | 115 |
| Valine | 117 | Threonine | 119 |
| Cysteine | 121 | Leucine | 131 |
| Isoleucine | 131 | Asparagine | 132 |
| Aspartic acid | 133 | Glutamine | 146 |
| Lysine | 146 | Glutamic acid | 147 |
| Methionine | 149 | Histidine (at pH 6.0) | 155 |
| Phenylalanine | 165 | Arginine | 174 |
| Tyrosine | 181 | Tryptophan | 204 |

Particularly preferred substitutions are:

- Lys for Arg and vice versa such that a positive charge may be maintained;
- Glu for Asp and vice versa such that a negative charge may be maintained;
- Ser for Thr such that a free —OH can be maintained; and
- Gln for Asn such that a free $NH_2$ can be maintained.

Exemplary and preferred conservative amino acid substitutions include any of: glutamine (Q) for glutamic acid (E) and vice versa; leucine (L) for valine (V) and vice versa; serine (S) for threonine (T) and vice versa; isoleucine (I) for valine (V) and vice versa; lysine (K) for glutamine (Q) and vice versa; isoleucine (I) for methionine (M) and vice versa; serine (S) for asparagine (N) and vice versa; leucine (L) for methionine (M) and vice versa; lysine (L) for glutamic acid (E) and vice versa; alanine (A) for serine (S) and vice versa; tyrosine (Y) for phenylalanine (F) and vice versa; glutamic acid (E) for aspartic acid (D) and vice versa; leucine (L) for isoleucine (I) and vice versa; lysine (K) for arginine (R) and vice versa.

Amino acid substitutions may also be introduced to substitute an amino acid with a particularly preferable property. For example, a Cys may be introduced a potential site for disulfide bridges with another Cys. A His may be introduced as a particularly "catalytic" site (i.e., His can act as an acid or base and is the most common amino acid in biochemical catalysis). Pro may be introduced because of its particularly planar structure, which induces β-turns in the protein's structure.

Two amino acid sequences are "highly homologous" or "substantially homologous" when at least about 70% of the amino acid residues (preferably at least about 80%, and most preferably at least about 90% or 95% or 98% or 99%) are identical, or represent conservative substitutions. The CDR regions of two antibodies are substantially homologous when one or more amino acids, or one or a few, or one to three, or one or two are substituted with a similar or conservative amino acid substitution, and wherein the antibody/antibodies have the profile of binding and activities of one or more of the antibodies, particularly one or more of antibody 1901-1A, 1901-1B, 1901-1C and/or 1901-1D disclosed herein. An antibody may be substantially homologous wherein one, two or three amino acids, or up to three amino acids, wherein one, two, three or four, or up to four amino acids, in the CDR domain regions are substituted with another amino acid and wherein the antibody retains the profile of antibody binding and activities.

Exemplary CDR domain region amino acid substitutions are provided herein. Thus, in accordance with the invention, antibody CDR domain sequences, particularly the 1901 murine antibody CDR domain sequences, have been modified whereby amino acid substitutions therein and variant CDR domain sequences are provided in the antibodies herein. In accordance with the invention, the antibodies of the present invention comprising new, variant or altered CDR domain sequences from murine 1901 antibody remarkably retain TGFB-3 binding, specificity and neutralization, and possess further improved attributes, including having sequences which have increased similarity to antibody variants produced naturally in humans. Thus, in accordance with the invention TGF-β3 antibodies, particularly TGF-β3 specific antibodies, are provided having heavy chain variable region comprising a CDR1 sequence SSWIH (SEQ ID NO:1), a CDR2 sequence RIYPGDGDTDYSEKFQ (SEQ ID NO:34), and a CDR3 sequence RMITTQAALDY (SEQ ID NO:35) or ARRMITTQAAL (SEQ ID NO:30); a CDR1 sequence SSWIH (SEQ ID NO:1), a CDR2 sequence RIYPGDGDTDYSEKFQ (SEQ ID NO:34), and a CDR3 sequence RMITTQAALDY (SEQ ID NO:35); or a CDR1 sequence GYTFSSSWIH (SEQ ID NO:28), a CDR2 sequence WIGRIYPGDGDTDYSEKFQ (SEQ ID NO:29), and a CDR3 sequence ARRMITTQAAL (SEQ ID NO:30). In a further aspect, antibodies of the invention may comprise a light chain variable region sequence comprising a CDR1 sequence KASQSVINAVA (SEQ ID NO:4), a CDR2 sequence YASNRYT (SEQ ID NO:5), and a CDR3 sequence QQDYSSPY (SEQ ID NO:33); a CDR1 sequence KASQSVINAVA (SEQ ID NO:4), a CDR2 sequence YASNRYT (SEQ ID NO:5), and a CDR3 sequence QQDYSSPY (SEQ ID NO:33) or QQDYSSPYT (SEQ ID NO:6); or a CDR1 sequence KASQSVINAVAWY (SEQ ID NO:31), a CDR2 sequence LLIYYASNRYT (SEQ ID NO:32), and a CDR3 sequence QQDYSSPY (SEQ ID NO:33) or QQDYSSPYT (SEQ ID NO:6).

In an aspect, antibody directed against TGF-β3 is provided comprising a heavy chain variable region comprising CDRs comprising a CDR1 sequence SSWIH (SEQ ID NO:1), a CDR2 sequence RIYPGDGDTDYSEKFQ (SEQ ID NO:34), and a CDR3 sequence comprising the sequence RMITTQAAL (SEQ ID NO:37). In one such aspect, the antibody comprises a heavy chain variable region comprising a CDR1 sequence SSWIH (SEQ ID NO:1), a CDR2 sequence RIYPGDGDTDYSEKFQ (SEQ ID NO:34), and a CDR3 sequence comprising RMITTQAAL (SEQ ID NO:37). In an aspect, the antibody comprises a heavy chain variable region comprising a CDR1 sequence SSWIH (SEQ ID NO:1), a CDR2 sequence RIYPGDGDTDYSEKFQ (SEQ ID NO:34), and a CDR3 sequence RMITTQAAL (SEQ ID NO:37). In a further aspect, antibody further comprising light chain variable region CDRs comprising a CDR1 sequence KASQSVINAVA (SEQ ID NO:4), a CDR2 sequence YASNRYT (SEQ ID NO:5), and a CDR3 sequence QQDYSSPY (SEQ ID NO:33) is provided. In another further aspect, antibody comprising light chain variable region CDRs comprising a CDR1 sequence KASQSVINAVA (SEQ ID NO:4) or KASQSVINAVAWY (SEQ ID NO:31), a CDR2 sequence YASNRYT (SEQ ID NO:5) or LLIYYASNRYT (SEQ ID NO:32), and a CDR3 sequence QQDYSSPY (SEQ ID NO:33) or QQDYSSPYT (SEQ ID NO:6) is provided.

A "heterologous" region of the DNA construct is an identifiable segment of DNA within a larger DNA molecule that is not found in association with the larger molecule in nature. Thus, when the heterologous region encodes a mammalian gene, the gene will usually be flanked by DNA that does not flank the mammalian genomic DNA in the genome of the source organism. Another example of a heterologous coding sequence is a construct where the coding sequence itself is not found in nature (e.g., a cDNA where the genomic coding sequence contains introns, or synthetic sequences having codons different than the native gene). Allelic variations or naturally-occurring mutational events do not give rise to a heterologous region of DNA as defined herein.

A DNA sequence is "operatively linked" to an expression control sequence when the expression control sequence controls and regulates the transcription and translation of that DNA sequence. The term "operatively linked" includes having an appropriate start signal (e.g., ATG) in front of the DNA sequence to be expressed and maintaining the correct reading frame to permit expression of the DNA sequence under the control of the expression control sequence and production of the desired product encoded by the DNA sequence. If a gene that one desires to insert into a recombinant DNA molecule does not contain an appropriate start signal, such a start signal can be inserted in front of the gene.

The term "agent" means any molecule, including polypeptides, antibodies, polynucleotides, chemical compounds and small molecules. In particular the term agent includes compounds such as test compounds or drug candidate compounds.

The term "agonist" refers to a ligand that stimulates the receptor the ligand binds to in the broadest sense.

The term "assay" means any process used to measure a specific property of a compound. A "screening assay" means a process used to characterize or select compounds based upon their activity from a collection of compounds.

The term "preventing" or "prevention" refers to a reduction in risk of acquiring or developing a disease or disorder (i.e., causing at least one of the clinical symptoms of the disease not to develop) in a subject that may be exposed to a disease-causing agent, or predisposed to the disease in advance of disease onset.

The term "prophylaxis" is related to and encompassed in the term 'prevention', and refers to a measure or procedure the purpose of which is to prevent, rather than to treat or cure a disease. Non-limiting examples of prophylactic measures may include the administration of vaccines; the administration of low molecular weight heparin to hospital patients at risk for thrombosis due, for example, to immobilization; and the administration of an anti-malarial agent such as chloroquine, in advance of a visit to a geographical region where malaria is endemic or the risk of contracting malaria is high.

"Therapeutically effective amount" means that amount of a drug, compound, antimicrobial, antibody, or pharmaceutical agent that will elicit the biological or medical response of a subject that is being sought by a medical doctor or other clinician. In particular, with regard to gram-positive bacterial infections and growth of gram-positive bacteria, the term "effective amount" is intended to include an effective amount of a compound or agent that will bring about a biologically meaningful decrease in the amount of or extent of tumor regression and or increase in length of a subject's survival or period disease-free or in remission. The phrase "therapeutically effective amount" is used herein to mean an amount sufficient to prevent, and preferably reduce by at least about 30 percent, more preferably by at least 50 percent, most preferably by at least 90 percent, a clinically significant change in the growth or amount of tumor size, or enhanced survival or disease-free period by at least about 30 percent, more preferably by at least 50 percent, most preferably by at least 90 percent.

The term "treating" or "treatment" of any disease or infection refers, in one embodiment, to ameliorating the disease or infection (i.e., arresting the disease or growth of the infectious agent or bacteria or reducing the manifestation, extent or severity of at least one of the clinical symptoms thereof). In another embodiment "treating" or "treatment" refers to ameliorating at least one physical parameter, which may not be discernible by the subject. In yet another embodiment, "treating" or "treatment" refers to modulating the disease or infection, either physically, (e.g., stabilization of a discernible symptom), physiologically, (e.g., stabilization of a physical parameter), or both. In a further embodiment, "treating" or "treatment" relates to slowing the progression of a disease or reducing an infection.

As used herein the term "fibrotic condition(s)" or "fibrotic diseas(es)" refers to and includes conditions or diseases characterized by excessive or persistent scarring, particularly due to excessive or abnormal production, deposition of extracellular matrix, and are that are associated with the abnormal accumulation of cells and/or fibronectin and/or collagen and/or increased fibroblast recruitment and include but are not limited to fibrosis of individual organs or tissues such as the heart, kidney, liver, joints, lung, pleural tissue, peritoneal tissue, skin, cornea, retina, musculoskeletal and digestive tract. In particular aspects, the term fibrotic diseases refers to idiopathic pulmonary fibrosis (IPF), cystic fibrosis, other diffuse parenchymal lung diseases of different etiologies including iatrogenic drug-induced fibrosis, occupational and/or environmental induced fibrosis, granulomatous diseases (sarcoidosis, hypersensitivity pneumonia), collagen vascular disease, alveolar proteinosis, langerhans cell granulomatosis, lymphangioleiomyomatosis, inherited diseases (Hermansky-Pudlak Syndrome, tuberous sclerosis, neurofibromatosis, metabolic storage disorders, familial interstitial lung disease), radiation induced fibrosis, chronic obstructive pulmonary disease (COPD), scleroderma, bleomycin induced pulmonary fibrosis, chronic asthma, silicosis, asbestos induced pulmonary fibrosis, acute respiratory distress syndrome (ARDS), kidney fibrosis, tubulointerstitium fibrosis, glomerular nephritis, focal segmental glomerular sclerosis, IgA nephropathy, hypertension, Alport syndrome, gut fibrosis, liver fibrosis, cirrhosis, alcohol induced liver fibrosis, toxic/drug induced liver fibrosis, hemochromatosis, nonalcoholic steatohepatitis (NASH), biliary duct injury, primary biliary cirrhosis, infection induced liver fibrosis, viral induced liver fibrosis, autoimmune hepatitis, corneal scarring, hypertrophic scarring, Dupuytren disease, keloids, cutaneous fibrosis, cutaneous scleroderma, systemic sclerosis, spinal cord injury/fibrosis, myelofibrosis, vascular restenosis, atherosclerosis, arteriosclerosis, Wegener's granulomatosis and Peyronie's disease.

The phrase "pharmaceutically acceptable" refers to molecular entities and compositions that are physiologically tolerable and do not typically produce an allergic or similar untoward reaction, such as gastric upset, dizziness and the like, when administered to a human.

As used herein, "pg" means picogram, "ng" means nanogram, "ug" or "μg" mean microgram, "mg" means milligram, "ul" or "μl" mean microliter, "ml" means milliliter, "1" means liter.

B. Detailed Disclosure

The invention provides antibodies directed against transforming growth factor beta 3 (TGF-β3) for diagnostic and therapeutic purposes. In particular, antibodies specific for TGF-β3 are provided, wherein said antibodies recognize and are capable of binding human and mouse TGF-β3, and do not recognize or bind other TGF beta forms, particularly the antibodies do not recognize or bind TGF-β1 or TGF-β2. In particular, the antibodies of the invention are humanized, and are modified or include amino acid substitutions to increase their similarity to antibody variants produced naturally in humans, while retaining or enhancing their TGF-β3 specificity and neutralization, including to enhance their suitability, acceptability and effectiveness in a human and for use in human diseases and conditions. Exemplary such TGF-β3 antibodies are particularly provided herein. Exemplary antibodies include antibodies 1901-1A, 1901-1B, 1901-1C and 1901-1D. Exemplary antibodies include antibodies comprising a heavy chain sequence SEQ ID NO: 18 or SEQ ID NO:19 or SEQ ID NO: 36. Exemplary antibodies include antibodies comprising a heavy chain sequence SEQ ID NO: 18 or SEQ ID NO:19. The invention particularly provides an antibody or active fragment thereof that recognizes and neutralizes TGF-β3, particularly wherein said antibody or active fragment does not recognize or neutralize TGF-β1 or TGF-β2.

In a general aspect, the present invention provides TGF-β3 antibodies directed against human and mouse TGF-β3, which neutralize TGF-β3 activity. In an aspect, such antibodies comprise the heavy chain variable region comprising a CDR1 sequence SSWIH (SEQ ID NO:1), a CDR2 sequence RIYPGDGDTDYSEKFQ (SEQ ID NO:34), and a CDR3 sequence RMITTQAALDY (SEQ ID NO:35) or ARRMITTQAAL (SEQ ID NO:30); a CDR1 sequence SSWIH (SEQ ID NO:1), a CDR2 sequence RIYPGDGDTDYSEKFQ (SEQ ID NO:34), and a CDR3 sequence RMITTQAALDY (SEQ ID NO:35); or a CDR1 sequence GYTFSSSWIH (SEQ ID NO:28), a CDR2 sequence WIGRIYPGDGDTDYSEKFQ (SEQ ID NO:29), and a CDR3 sequence ARRMITTQAAL (SEQ ID NO:30). In a further aspect, antibodies of the invention may comprise a light chain variable region sequence comprising a CDR1 sequence KASQSVINAVA (SEQ ID NO:4), a CDR2 sequence YASNRYT (SEQ ID NO:5), and a CDR3 sequence QQDYSSPY (SEQ ID NO:33); a CDR1 sequence KASQSVINAVA (SEQ ID NO:4), a CDR2 sequence YASNRYT (SEQ ID NO:5), and a CDR3 sequence QQDYSSPY (SEQ ID NO:33) or QQDYSSPYT (SEQ ID NO:6); or a CDR1 sequence KASQSVINAVAWY (SEQ ID NO:31), a CDR2 sequence LLIYYASNRYT (SEQ ID NO:32), and a CDR3 sequence QQDYSSPY (SEQ ID NO:33) or QQDYSSPYT (SEQ ID NO:6). In one such aspect, the invention provides TGF-β3 antibodies comprising a heavy chain sequence SEQ ID NO: 18 or SEQ ID NO:19 or SEQ ID NO:36. In one such aspect, the invention provides TGF-β3 antibodies comprising a heavy chain sequence SEQ ID NO: 18 or SEQ ID NO:19. Exemplary antibodies are provided including antibody 1901-1A, 1901-1B, 1901-1C and 1901-1D. The present invention provides TGF-β3 antibodies directed against human and mouse TGF-β3, which do not cross react with or bind to TGF-β1 and/or TGF-β3 and which specifically neutralize TGF-β3 activity. In a particular aspect, antibody of the present invention blocks TGF-β3-mediated signaling and/or TGF-β3 mediated cell response or cell proliferation. In a particular aspect, the invention provides anti-TGF-β3 specific antibodies 1901-1A, 1901-1B, 1901-1C and 1901-1D. In a further particular aspect the invention provides TGF-β3 specific antibody capable of specifically binding and neutralizing TGF-β3 comprising the heavy chain amino acid sequence as set out in SEQ ID NO:18 or 19 or 36 and in FIG. 10, 11, 12 or 13.

In another aspect, the invention provides an antibody directed against TGF-β3 comprising a heavy chain variable region sequence comprising a CDR1 sequence SSWIH (SEQ ID NO:1), a CDR2 sequence RIYPGDGDTDYSEKFQ (SEQ ID NO:34), and a CDR3 sequence RMITTQAALDY (SEQ ID NO:35), or a CDR1 sequence GYTFSSSWIH (SEQ ID NO:28), a CDR2 sequence WIGRIYPGDGDTDYSEKFQ (SEQ ID NO:29), and a CDR3 sequence ARRMITTQAAL (SEQ ID NO:30), and a light chain variable region comprising a CDR1 sequence KASQSVINAVA (SEQ ID NO:4), a CDR2 sequence YASNRYT (SEQ ID NO:5), and a CDR3 sequence QQDYSSPY (SEQ ID NO:33) or QQDYSSPYT (SEQ ID NO:6); or a CDR1 sequence KASQSVINAVAWY (SEQ ID NO:31), a CDR2 sequence LLIYYASNRYT (SEQ ID NO:32), and a CDR3 sequence QQDYSSPY (SEQ ID NO:33) or QQDYSSPYT (SEQ ID NO:6).

In an aspect, the invention provides an antibody directed against TGF-β3 comprising a heavy chain variable region comprising CDRs comprising a CDR1 sequence SSWIH (SEQ ID NO:1), a CDR2 sequence RIYPGDGDTDYSEKFQ (SEQ ID NO:34), and a CDR3 sequence comprising the sequence RMITTQAAL (SEQ ID NO:37). In one such aspect, the antibody comprises a heavy chain variable region comprising a CDR1 sequence SSWIH (SEQ ID NO:1), a CDR2 sequence RIYPGDGDTDYSEKFQ (SEQ ID NO:34), and a CDR3 sequence comprising RMITTQAAL (SEQ ID NO:37). In an aspect, the antibody comprises a heavy chain variable region comprising a CDR1 sequence SSWIH (SEQ ID NO:1), a CDR2 sequence RIYPGDGDTDYSEKFQ (SEQ ID NO:34), and a CDR3 sequence RMITTQAAL (SEQ ID NO:37). In a further aspect, antibody further comprising light chain variable region CDRs comprising a CDR1 sequence KASQSVINAVA (SEQ ID NO:4), a CDR2 sequence YASNRYT (SEQ ID NO:5), and a CDR3 sequence QQDYSSPY (SEQ ID NO:33) is provided. In another further aspect, antibody comprising light chain variable region CDRs comprising a CDR1 sequence KASQSVINAVA (SEQ ID NO:4) or KASQSVINAVAWY (SEQ ID NO:31), a CDR2 sequence YASNRYT (SEQ ID NO:5) or LLIYYASNRYT (SEQ ID NO:32), and a CDR3 sequence QQDYSSPY (SEQ ID NO:33) or QQDYSSPYT (SEQ ID NO:6) is provided.

In another aspect of the invention, provided herein is an antibody(ies) or fragment(s) thereof that binds to the same epitope of TGF-β (such as particularly, human TGF-β3) as the antibody(ies) described herein. In another embodiment, provided herein is an antibody(ies) or antigen-binding fragment(s) thereof that competes with an antibody or antigen-binding fragment thereof described herein for binding to TGF-β3 (e.g., human TGF-β3). In a specific embodiment, provided herein is an antibody(ies) or antigen-binding fragment(s) thereof that competes with antibody or antigen-binding fragment thereof described herein for binding to TGF-β3 (e.g., human TGF-β3) to the extent that the antibody or antigen-binding fragment thereof described herein self-competes for binding to TGF-β3 (e.g., human TGF-β3).

The unique specificity and affinity of the antibodies and fragments of the invention provides diagnostic and therapeutic uses to identify, characterize and target conditions associated with TGF-β3 expression, activity or activation. In particular, antibodies of the invention targeting TGF-β3 are useful in modulating immune response. In an aspect thereof, antibodies of the invention targeting TGF-β3 are useful in modulating immune response against cancer, cancer or tumor cells, and cancer or tumor antigens. The antibodies have applicability in therapeutic treatment or management of cancer. The antibodies have applicability in enhancing the anti-cancer immune response and in enhancing cancer vaccines. The antibodies have applicability in enhancing the therapeutic effect including the anti-cancer and/or anti-cellular effect of radiation therapy(ies). In a particular aspect the antibodies of the invention are applicable in treatment, management and/or prevention of cancers, including in cancer recurrence and metastasis. Applicable conditions include infectious disease, cancers, host immune response including in transplantation and immune diseases or disorders, such as autoimmune diseases or inflammatory conditions. Applicable cancers include adrenocortical carcinoma, AIDS-related cancers, AIDS-related lymphoma, anal cancer, anorectal cancer, cancer of the anal canal, appendix cancer, childhood cerebellar astrocytoma, basal cell carcinoma, skin cancer (non-melanoma), biliary cancer, extrahepatic bile duct cancer, intrahepatic bile duct cancer, bladder cancer, urinary bladder cancer, bone and joint cancer, osteosarcoma and malignant fibrous histiocytoma, brain cancer, brain tumor, brain stem glioma, cerebellar astrocytoma, cerebral astrocytoma/malignant glioma, ependymoma, medulloblastoma, supratentorial primitive neuroectodeimal tumors, visual pathway and hypothalamic glioma, breast cancer, bronchial adenomas/carcinoids, carcinoid tumor, gastrointestinal, nervous system cancer, nervous system lymphoma, central nervous system cancer, central nervous system lymphoma, cervical cancer, childhood cancers, chronic lymphocytic leukemia, chronic myelogenous leukemia, chronic myeloproliferative disorders, colon cancer, colorectal cancer, cutaneous T-cell lymphoma, lymphoid neoplasm, mycosis fungoides, Seziary Syndrome, endometrial cancer, esophageal cancer, extracranial germ cell tumor, extragonadal germ cell tumor, extrahepatic bile duct cancer, eye cancer, intraocular melanoma, retinoblastoma, gallbladder cancer, gastric (stomach) cancer, gastrointestinal carcinoid tumor, gastrointestinal stromal tumor (GIST), germ cell tumor, ovarian germ cell tumor, gestational trophoblastic tumor glioma, head and neck cancer, hepatocellular (liver) cancer, Hodgkin lymphoma, hypopharyngeal cancer, intraocular melanoma, ocular cancer, islet cell tumors (endocrine pancreas), Kaposi Sarcoma, kidney cancer, renal cancer, kidney cancer, laryngeal cancer, acute lymphoblastic leukemia, acute myeloid leukemia, chronic lymphocytic leukemia, chronic myelogenous leukemia, hairy cell leukemia, lip and oral cavity cancer, liver cancer, lung cancer, non-small cell lung cancer, small cell lung cancer, AIDS-related lymphoma, non-Hodgkin lymphoma, primary central nervous system lymphoma, Waldenstram macroglobulinemia, medulloblastoma, melanoma, intraocular (eye) melanoma, merkel cell carcinoma, mesothelioma malignant, mesothelioma, metastatic squamous neck cancer, mouth cancer, cancer of the tongue, multiple endocrine neoplasia syndrome, mycosis fungoides, myelodysplastic syndromes, myelodysplastic/myeloproliferative diseases, chronic myelogenous leukemia, acute myeloid leukemia, multiple myeloma, chronic myeloproliferative disorders, nasopharyngeal cancer, neuroblastoma, oral cancer, oral cavity cancer, oropharyngeal cancer, ovarian cancer, ovarian epithelial cancer, ovarian low malignant potential tumor, pancreatic cancer, islet cell pancreatic cancer, paranasal sinus and nasal cavity cancer, parathyroid cancer, penile cancer, pharyngeal cancer, pheochromocytoma, pineoblastoma and supratentorial primitive neuroectodermal tumors, pituitary tumor, plasma cell neoplasm/multiple myeloma, pleuropulmonary blastoma, prostate cancer, rectal cancer, renal pelvis and ureter, transitional cell cancer, retinoblastoma, rhabdomyosarcoma, salivary gland cancer, ewing family of sarcoma tumors, Kaposi Sarcoma, soft tissue sarcoma, uterine cancer, uterine sarcoma, skin cancer (non-melanoma), skin cancer (melanoma), merkel cell skin carcinoma, small intestine cancer, soft tissue sarcoma, squamous cell carcinoma, stomach (gastric) cancer, supratentorial primitive neuroectodermal tumors, testicular cancer, throat cancer, thymoma, thymoma and thymic carcinoma, thyroid cancer, transitional cell cancer of the renal pelvis and ureter and other urinary organs, gestational trophoblastic tumor, urethral cancer, endometrial uterine cancer, uterine sarcoma, uterine corpus cancer, vaginal cancer, vulvar cancer, and Wilm's Tumor. In an aspect applicable cancers include or are selected from breast, melanoma, prostate and lung cancer. In an aspect, the TGF-β3 antibodies of the invention have applicability in treatment or modulation of breast, melanoma, prostate or lung cancer.

Evidence of TGFβ production by tumor cells and by myeloid-derived suppressor cells along with TGFβ immune suppressive activity at the tumor site supports that blocking TGFβ, particularly specifically blocking TGF-β3, can enhance antigen uptake, presentation, and activation of antitumor immune response, including wherein the antitumor response is mediated by cancer antigen or other antigen directed T cells and/or mediated by therapeutic vaccines. Thus, in an aspect of the invention TGF-β3 antibody(ies), particularly TGF-β3 neutralizing antibody(ies), may be administered in conjunction with or in a composition of cancer antigen(s) and adjuvant(s), including to patients to promote a more robust priming and activation of the adaptive anti-tumor response to enhance immune therapies directed at cancers. Additional inhibitors to TGFβ activity, such as small molecules, antisense or aptamers can also be used to inhibit TGFβ activity, including or specifically TGF-β3.

Potent anti-tumor immunity requires modulating multiple arms of host immune response and targeting pathways that contributes to tumor cell growth and survival. Combining agents that modulate immune response and arrest tumor growth and progression can generate anticancer immunity and arrest tumor growth to improve clinical outcomes (Vanneman, M (2012) Nature Reviews Cancer (12):237-251). Thus, in an aspect of the invention the anti-TGF-β3 antibody(ies) may be administered alone or in combination with other treatments, therapeutics or agents, either simultaneously or sequentially dependent upon the condition to be treated. Immune modulators may be included in a composition with or administered with TGF-β3 antibody(ies) and/or administered at a different time to enhance immune modulation and/or cancer therapy, including immune therapies directed against cancer. An immune modulator may be an adjuvant. Applicable immune modulators include IDO, TDO (Platten M (2012) Cancer Research 72(21):5435-40), α-galactosyl ceramide and analogs thereof such as threitolceramide (ThrCer) and ThrCer 6, TLR ligands such as poly I:C (TLR3), MPL (TLR4), imiquimod (TLR7), R848 (TLR8) or CpG (TLR9), iCOS, CTLA-4, PD1, PD1 ligand, OX40 and OX40 ligand, Lag3, GITR, GITR ligand interleukins, tumor necrosis factor (TNF) or other growth factors, colony stimulating factors, T cell modulators including modulators of $CD8^+$ T cells, cytokines or hormones which stimulate the immune response or reduction or elimination of cancer cells or tumors (Mellman I (2011) Nature (480): 480-489). Additional immunmodulators are small molecules, antagonist antibodies or agonist antibodies targeting the applicable immune modulators including IDO, TDO, Toll like receptor family or iCOS, CTLA-4, PD1, PD1 ligand, OX40 and OX40 ligand, interleukins, tumor necrosis factor (TNF) or other growth factors, colony stimulating factors, T cell modulators including modulators of $CD8^+$ T cells, cytokines which stimulate the immune response or reduction or elimination of cancer cells or tumors.

Additional immune modulators, including TLR ligands such as poly I:C (TLR3), MPL (TLR4), imiquimod (TLR7), R848 (TLR8) or CpG (TLR9) can be used in combination with TGF-β3 specific neutralizing antibody to produce an enhanced immune stimulation and resulting protection from conditions in which it is desirable for the immune system to respond effectively such as infectious disease or cancer.

TGF-β3 specific antibody(ies) can also be used as immunostimulant(s) or adjuvant(s) in combined use with antigenic materials such as, without limitation, proteins, peptides, or nucleic acids and so forth in order to produce a protective immune response, such as a B-cell and IgG antibody response to the administered antigen. TGF-β3 specific antibody(ies) can also be used as immunostimulant(s) or adjuvant(s) in combined use with antigenic materials such as, without limitation, proteins, peptides, or nucleic acids and so forth in order to produce a protective immune response, such as a T-cell or CTL response to the administered antigen.

Such antigenic materials could be and may include any materials suitable for prevention or therapy of a/the particular disease. Specifically, with regards to cancer, examples of tumor associated peptide and protein antigens that can be administered to induce or enhance an immune response are derived from tumor associated genes and encoded proteins including MAGE-A1, MAGE-A2, MAGE-A3, MAGE-A4, MAGE-A5, MAGE-A6, MAGE-A7, MAGE-A8, MAGE-A9, MAGE-A10, MAGE-A11, MAGE-A12, MAGE-A13, GAGE-1, GAGE-2, GAGE-3, GAGE-4, GAGE-5, GAGE-6, GAGE-7, GAGE-8, BAGE-1, RAGE-1, LB33/MUM-1, PRAME, NAG, MAGE-Xp2 (MAGE-B2), MAGE-Xp3 (MAGE-B3), MAGE-Xp4 (MAGE-B4), tyrosinase, brain glycogen phosphorylase, Melan-A, MAGE-C1, MAGE-C2, NY-ESO-1, LAGE-1, SSX-1, SSX-2(HOM-MEL-40), SSX-1, SSX-4, SSX-5, SCP-1 and CT-7. For example, antigenic peptides characteristic of tumors include those listed in published PCT application WO00/20581 (PCT/US99/21230).

Other TGF-β-related, particularly TGF-β3-related, disorders, diseases, or conditions, which would benefit from treatment with the anti TGF-β3 antibody include diseases characterized by accumulation of extracellular matrix, diseases caused by circulating TGF-β3 or TGF-β3 activated at a local site, conditions caused by suppression of the immune system due to endogenous TGF-β3 production, acute immune deficiencies resulting from severe injuries, burns, and illnesses such as viral or bacterial infections, multi-organ systemic illnesses due to TGF-β3 production or over-production, and TGF-β3-producing tumors. Non-limiting specific examples include neuronal, glial, astrocytal, hypothalamic and other glandular, macrophagal, epithelial, stromal and blastocoelic disorders, fibrosis, scarring, tissue damage such as caused by radiation, and adhesion during wound healing, fibrotic skin disorders such as scleroderma, CNS pathology scar tissue, dermal scarring, keloid scarring, and neural scarring, fibrotic diseases of the peritoneal cavity, lungs, liver, and kidneys such as chronic hepatic fibrosis, acute liver injury, interstitial lung and renal fibrosis, and liver cirrhosis, cystic fibrosis, vascular disorders, e.g., cardiac fibrosis, arterial injury such as atherosclerosis and arteriosclerosis, angiopathy, vasculopathy, nephropathy, systemic sclerosis, infections such as macrophage pathogen infections and viral infections such as hepatitis C and HIV, immunological, angiogenic, and inflammatory disorders and deficiencies such as rheumatoid arthritis, an ocular disorder, especially those involving ocular fibrosis, including proliferative retinopathy, retinal detachment and post-glaucoma drainage surgery such as neural retina, retinal pigment epithelium-choroid and vitreous of the human eye, and cataracts, osteoporosis, adult respiratory distress syndrome, post-myocardial infarction, post-angioplasty restenosis, glomerulonephritis, a diabetes-related condition such as hyperglycemia, diabetes, diabetic kidney disease, diabetic nephropathy, diabetic neuropathy or retinopathy, and macrophage-deficiency diseases.

In another specific embodiment, provided herein is a first antibody or antigen-binding fragment thereof that competes with an antibody or antigen-binding fragment thereof described herein for binding to TGF-β3 (e.g., human TGF-β3), wherein the first antibody or antigen-binding fragment thereof competes for binding in an assay comprising the following steps: (a) incubating TGF-β3 coated ELISA plates with the first antibody or antigen-binding fragment thereof in unlabeled form; (b) adding labeled antibody or antigen-binding fragment thereof described herein to the TGF-β3 coated ELISA plates and incubating TGF-β3 coated ELISA plates; and (c) detecting the binding of the antibody or antigen-binding fragment thereof described herein to TGF-β3. In an aspect, binding of an antibody 1901-1A or antigen binding fragment thereof, antibody 1901-1B or antigen binding fragment thereof, antibody 1901-1C or antigen binding fragment thereof, or antibody 1901-1D or antigen binding fragment thereof is detected after incubation with the first antibody or antigen binding fragment thereof. In an aspect, binding of an antibody comprising the heavy chain variable region sequence SEQ ID NO: 18 or SEQ ID NO:19 or SEQ ID NO:36 or antigen binding fragment thereof is detected after incubation with the first antibody or antigen binding fragment thereof. In an aspect, provided herein is a first antibody or antigen-binding fragment thereof that competes with an antibody or antigen-binding fragment thereof described herein for binding to TGF-β3 (e.g., human TGF-β3), wherein the first antibody or antigen-binding fragment thereof competes for binding in an assay comprising the following steps: (a) incubating TGF-β3 coated ELISA plates with the first antibody or antigen-binding fragment thereof in unlabeled form; (b) adding the biotinylated antibody or antigen-binding fragment thereof described herein to the TGF-β3 coated ELISA plates and incubating TGF-β3 coated ELISA plates; and (c) detecting the binding of the antibody or antigen-binding fragment thereof described herein to TGF-β3. In an aspect hereof, the labeled or biotinylated antibody or antigen binding fragment thereof is selected from antibody 1901-1A or antigen binding fragment thereof, antibody 1901-1B or antigen binding fragment thereof, antibody 1901-1C or antigen binding fragment thereof, or antibody 1901-1D or antigen binding fragment thereof. In an aspect, binding of antibody or antigen binding fragment of one or more of 1901-1A, 1901-1B, 1901-1C or 1901-1D is reduced, in particular is significantly reduced, in the presence of first antibody or antigen-binding fragment thereof in unlabeled form.

In another specific embodiment, provided herein is a first antibody or antigen-binding fragment thereof that competes with an antibody or antigen-binding fragment thereof described herein for binding to TGF-β3 (e.g., human TGF-β3), wherein the competition is exhibited as reduced binding of first antibody or antigen-binding fragment thereof to TGF-β3 (e.g., human TGF-β3) by more than 60% (e.g., 65%, 70%, 75%, 85%, 90%, 95%, or 98%, or between 60% to 65%, 65% to 70%, 70% to 75%, 75% to 80%, 80% to 85%, 85% to 95%, or 95% to 100%). In another specific embodiment, provided herein is a first antibody or antigen-binding fragment thereof that competes with an antibody or antigen-binding fragment thereof described herein for binding to TGF-β3 (e.g., human TGF-β3), wherein the competition is exhibited as reduced binding of antibody or antigen binding fragment of one or more of 1901-1A, 1901-1B, 1901-1C or 1901-1D by more than 60% (e.g., 65%, 70%, 75%, 85%, 90%, 95%, or 98%, or between 60% to 65%, 65% to 70%, 70% to 75%, 75% to 80%, 80% to 85%, 85% to 95%, or 95% to 100%) in the presence and/or after binding of the first antibody or antigen-binding fragment thereof.

In specific aspects, provided herein is an antibody which competes (e.g., in a dose dependent manner) for specific binding to TGF-β3 (e.g., human TGF-β3), with an antibody comprising (i) a VL domain comprising a VL CDR1, VL CDR2, and VL CDR3 having the amino acid sequences of the VL CDRs of an antibody provided in FIG. 10, 11, 12 or 13; and (ii) a VH domain comprising a VH CDR1, VH CDR2, and VH CDR3 having the amino acid sequences of the CDRs of an antibody provided in FIG. 10, 11, 12 or 13.

In a particular embodiment, provided herein is an antibody that competes (e.g., in a dose-dependent manner), for specific binding to TGF-β3 (e.g., human TGF-β3), with an antibody comprising the VH CDRs of antibody 1901-1A, 1901-1B, 1901-1C or 1901-1D. In a particular embodiment, provided herein is an antibody that competes, for specific binding to TGF-β3 (e.g., human TGF-β3), with an antibody comprising the VH and VL CDRs of antibody 1901-1A, 1901-1B, 1901-1C or 1901-1D.

In specific aspects, provided herein is an antibody, or an antigen-binding fragment thereof, which immunospecifically binds to the same epitope as that of an antibody (e.g., 1901-1A, 1901-1B, 1901-1C or 1901-1D) comprising the amino acid sequences described herein (see, e.g., FIGS. 7, 8, 10, 11, 12, 13) for specific binding to TGF-β3 (e.g., human TGF-β3). Assays known to one of skill in the art or described herein (e.g., X-ray crystallography, ELISA assays, etc.) can be used to determine if two antibodies bind to the same epitope.

Panels of monoclonal antibodies recognizing human and murine TGF-β3 can be screened for various properties; i.e., isotype, epitope, affinity, etc. Of particular interest are antibodies that mimic the activity of exemplary antibodies 1901-1A, 1901-1B, 1901-1C or 1901-1D, and have affinity for human and mouse TGF-β3, do not react with TGF-β1 or TGF-β2, and directly affect the activity of TGF-β3, in particular neutralize TGF-β3.

A monoclonal antibody of the present invention may comprise heavy chain variable region, such as exemplified in SEQ ID NO: 18 or SEQ ID NO:19, and optionally light chain variable region. In general, the CDR regions, comprising amino acid sequences substantially as set out as the variant CDR regions of FIGS. 7 and 8, particularly heavy chain CDRs of SEQ ID NOs: 1, 34, 35, 30, 28, 29, optionally with light chain CDRs SEQ ID NOS: 4, 5, 33, 6, 31, 32, will be carried in a structure which allows for binding of the CDR regions to the TGF-β3, and particularly to human and mouse TGF-β3.

By "substantially as set out" it is meant that variable region sequences, and/or particularly the CDR sequences, of the invention will be either identical or highly homologous to the specified regions of FIGS. 7, 8, 10, 11, 12 and/or 13. By "highly homologous" it is contemplated that only a few substitutions, preferably from 1 to 8, preferably from 1 to 5, preferably from 1 to 4, or from 1 to 3, or 1 or 2 substitutions may be made in the variable region sequence and/or in the CDR sequences. The term substantially set out as includes particularly conservative amino acid substitutions which do not materially or significantly affect the specificity and/or activity of the instant antibodies. Conservative and non-conservative amino acid substitutions are contemplated herein for the variable region sequences and also for the CDR region sequences.

Substitutions may be made in the variable region sequence outside of the CDRs so as to retain the CDR sequences. Thus, changes in the variable region sequence or alternative non-homologous or veneered variable region sequences may be introduced or utilized, such that the CDR sequences are maintained and the remainder of the variable region sequence may be substituted.

Alternatively, substitutions may be made particularly in the CDRs. Exemplary CDR sequences for antibody, particularly antibody 1901-1A, 1901-1B, 1901-1C and 1901-1D, of the present invention are set out and described herein including in FIGS. 10, 11, 12 and 13 and in SEQ ID NOs: 1, 34, 35, 28, 29, 30, 4, 5, 6, 31, 32 and 33. The exemplary CDR sequences include substitutions in the CDR sequences, particularly wherein CDR region amino acids of murine 1901 antibody have been altered or substituted. Antibodies of the invention having substitutions as above described and contemplated are selected to maintain the activities and specificity commensurate with the exemplary antibodies, including antibody 1901-1A, 1901-1B, 1901-1C and/or 1901-1D and having the characteristics as set out herein and in the claims.

There are several recognized and known methods and approaches to determine the CDRs in an antibody. The most commonly used CDR identification methods at present are Kabat (Wu T T, Kabat E A (1970) J Exp Med 132:211-250; Kabat E A et al (1983) Sequence of Proteins of Immunological Interest. Bethesda: National Institute of Health), IMGT (Lefranc M P et al (2003) Dev Comp Immunol 27:55-77) and Chothia (Chothia C, Lesk A M (1987) J Mol Biol 196:901-917; Chothia C et al (1989) Nature 342:877-883; Lefranc M P et al (2003) Dev Comp Immunol 27:55-77). Each of these methods has devised a unique residue numbering scheme according to which it numbers the hypervariable region residues and the beginning and ending of each of the six CDRs is then determined according to certain key positions. IMGT was generally utilized in the present studies. While these different approaches may identify slightly offset CDR sequences, they generally provide overlapping sequences and amino acids and can be useful in combination to identify amino acids which should be maintained or conserved and those that may be suitable for variation or alteration while maintaining binding.

A substantial portion of an immunoglobulin variable domain will comprise at least the three CDR regions, together with their intervening framework regions. Preferably, the portion will also include at least about 50% of either or both of the first and fourth framework regions, the 50% being the C-terminal 50% of the first framework region and the N-terminal 50% of the fourth framework region. Additional residues at the N-terminal or C-terminal end of the substantial part of the variable domain may be those not normally associated with naturally occurring variable domain regions. For example, construction of specific binding members of the present invention made by recombinant DNA techniques may result in the introduction of N- or C-terminal residues encoded by linkers introduced to facilitate cloning or other manipulation steps. Other manipulation steps include the introduction of linkers to join variable domains of the invention to further protein sequences including immunoglobulin heavy chains, other variable domains (for example in the production of diabodies) or protein labels as provided herein and/or known to those of skill in the art.

Although in a preferred aspect of the invention specific binding members comprising a pair of binding domains based on sequences substantially set out in FIG. 7, 8, 10, 11, 12 or 13 are preferred, single binding domains based on these sequences, particularly based on the heavy chain and light chain CDRs, form further aspects of the invention. In the case of the binding domains based on the sequence substantially set out in FIG. 7, 8, 10, 11, 12 or 13, such binding domains may be used as targeting agents for TGF-β3, since it is known that immunoglobulin VH domains are capable of binding target antigens in a specific manner.

Portions or domains of the antibodies of the invention are contemplated and incorporated, including any portion or domain, including those modified or fused to reagents, labels or other domains or fragments, wherein the portions or domains retain the characteristics of the antibodies hereof, including TGF-β3 specific binding, and optionally including TGF-β3 specific neutralization, as exemplified in antibody 1901-1A, 1901-1B, 1901-1C and 1901-1D hereof. Antibodies and antibody fragments of the invention include smaller recombinant antibody fragments (for example, classic monovalent antibody fragments (Fab, scFv) and engineered variants (diabodies, triabodies, minibodies and single-domain antibodies) that retain the targeting specificity of the whole antibodies (mAbs) (for review see Hollinger P and Hudson P J (2005) Nature Biotech 23(9):1126-1136). These include for example domain antibody (dAb) fragment, which comprises a single variable domain (Ward, E. S. et al., Nature 341, 544-546 (1989)); camelid antibody; isolated complementarity determining region (CDR); Single Chain Fv Fragments wherein a VH domain and a VL domain are linked by a peptide linker which allows the two domains to associate to form an antigen binding site (Bird et al, Science, 242, 423-426, 1988; Huston et al, PNAS USA, 85, 5879-5883, 1988); a diabody, which is a bivalent, bispecific antibody in which VH and VL domains are expressed on a single polypeptide chain, but using a linker that is too short to allow for pairing between the two domains on the same chain, thereby forcing the domains to pair with the complementarity domains of another chain and creating two antigen binding sites (WO94/13804; P. Holliger et al Proc. Natl. Acad. Sci. USA 90 6444-6448, (1993)); a linear antibody, which comprises a pair of tandem Fv segments (VH-CH1-VH-CH1) which, together with complementarity light chain polypeptides, form a pair of antigen binding regions; multivalent antibody fragments (scFv dimers, trimers and/or tetramers (Power and Hudson, J Immunol. Methods 242: 193-204 9 (2000)); and minibody, which is a bivalent molecule comprised of scFv fused to constant immunoglobulin domains, CH3 or CH4 (for example IgG1 (CH3) and IgE (CH4)), wherein the constant CH3 or CH4 domains serve as dimerization domains (Olafsen T et al (2004) Prot Eng Des Sel 17(4):315-323; Hollinger P and Hudson P J (2005) Nature Biotech 23(9):1126-1136). These smaller antibodies and engineered variants or fragments can be produced more economically and may possess other unique and superior properties for a range of diagnostic and therapeutic applications. For example, scFV2-Fc can accumulate in higher abundance in tumor or tissue, and a minibody is approximately 80 kD and may be ideal for therapy because of higher uptake in tissues, have faster clearance and have better tissue to blood ratios than intact immunoglobulin (150 kDa) or Fab'2 (110 kDa). The antibody fragments may be forged into multivalent and multispecific reagents, linked to therapeutic payloads (such as radionuclides, toxins, enzymes, liposomes and viruses) and engineered for enhanced therapeutic efficacy. Recently, single antibody domains have been engineered and selected as targeting reagents against hitherto immunosilent cavities in enzymes, receptors and infectious agents.

Specific binding members of the present invention may further comprise antibody constant regions or parts thereof. For example, specific binding members based on the sequences of FIG. 7, 8, 10, 11, 12 or 13 may be attached at their C-terminal end to antibody light chain constant domains including human Cκ or Cλ chains, preferably CX, chains. Similarly, specific binding members based on the sequences of FIG. 7, 8, 10, 11, 12 or 13 may be attached at their C-terminal end to all or part of an immunoglobulin heavy chain derived from any antibody isotype, e.g. IgG, IgA, IgE, IgD and IgM and any of the isotype sub-classes, particularly IgG1, IgG2b, and IgG4. IgG1 is preferred.

The antibodies, or any fragments thereof, may be conjugated or recombinantly fused to any cellular toxin, bacterial or other, e.g. pseudomonas exotoxin, ricin, or diphtheria toxin. The part of the toxin used can be the whole toxin, or any particular domain of the toxin. Such antibody-toxin molecules have successfully been used for targeting and therapy of different kinds of cancers, see e.g. Pastan, Biochim Biophys Acta. 1997 Oct. 24; 1333(2):C1-6; Kreitman et al., N Engl J Med. 2001 Jul. 26; 345(4):241-7; Schnell et al., Leukemia. 2000 January; 14(1):129-35; Ghetie et al., Mol Biotechnol. 2001 July; 18(3):251-68.

Bi- and tri-specific multimers can be formed by association of different scFv molecules and have been designed as cross-linking reagents for T-cell recruitment into tumors (immunotherapy), viral retargeting (gene therapy) and as red blood cell agglutination reagents (immunodiagnostics), see e.g. Todorovska et al., J Immunol Methods. 2001 Feb. 1; 248(1-2):47-66; Tomlinson et al., Methods Enzymol. 2000; 326:461-79; McCall et al., J Immunol. 2001 May 15; 166(10):6112-7.

Fully human antibodies can be prepared by immunizing transgenic mice carrying large portions of the human immunoglobulin heavy and light chains. These mice, examples of such mice are the Xenomouse™ (Abgenix, Inc.) (U.S. Pat. Nos. 6,075,181 and 6,150,584), the HuMAb-Mouse™ (Medarex, Inc./GenPharm) (U.S. Pat. Nos. 5,545,806 and 5,569,825), the TransChromo Mouse™ (Kirin) and the KM Mouse™ (Medarex/Kirin), are well known within the art. Antibodies can then be prepared by, e.g. standard hybridoma technique or by phage display. These antibodies will then contain only fully human amino acid sequences. Fully human antibodies can also be generated using phage display from human libraries. Phage display may be performed using methods well known to the skilled artisan, and as provided herein as in Hoogenboom et al and Marks et al (Hoogenboom H R and Winter G. (1992) J Mol Biol. 227(2):381-8; Marks J D et al (1991) J Mol Biol. 222(3): 581-97; and also U.S. Pat. Nos. 5,885,793 and 5,969,108).

Antibodies of the invention may be labelled with a detectable or functional label. Detectable labels include, but are not limited to, radiolabels such as the isotopes $^{3}H$, $^{14}C$, $^{32}P$, $^{35}S$, $^{36}Cl$, $^{51}Cr$, $^{57}CO$, $^{58}Co$, $^{59}Fe$, $^{90}Y$, $^{121}I$, $^{124}I$, $^{121}I$, $^{131}I$, $^{111}In$, $^{117}Lu$, $^{211}At$, $^{198}Au$, $^{67}Cu$, $^{225}Ac$, $^{213}Bi$, $^{99}Tc$ and $^{186}Re$, which may be attached to antibodies of the invention using conventional chemistry known in the art of antibody imaging. Labels also include fluorescent labels (for example fluorescein, rhodamine, Texas Red) and labels used conventionally in the art for MRI-CT imaging. They also include enzyme labels such as horseradish peroxidase, β-glucoronidase, β-galactosidase, urease. Labels further include chemical moieties such as biotin which may be detected via binding to a specific cognate detectable moiety, e.g. labelled avidin. Functional labels include substances which are designed to be targeted to the site of a tumor to cause destruction of tumor tissue. Such functional labels include cytotoxic drugs such as 5-fluorouracil or ricin and enzymes such as bacterial carboxypeptidase or nitroreductase, which are capable of converting prodrugs into active drugs at the site of a tumor.

As used herein, an "epitope" is a term in the art and refers to a localized region of an antigen to which an antibody can specifically bind. An epitope can be, for example, contiguous amino acids of a polypeptide (linear or contiguous epitope) or an epitope can, for example, come together from two or more non-contiguous regions of a polypeptide or polypeptides (conformational, non-linear, discontinuous, or non-contiguous epitope). In certain embodiments, the epitope to which an antibody binds can be determined by, e.g., NMR spectroscopy, X-ray diffraction crystallography studies, ELISA assays, hydrogen/deuterium exchange coupled with mass spectrometry (e.g., MALDI mass spectrometry), array-based oligo-peptide scanning assays, and/or mutagenesis mapping (e.g., site-directed mutagenesis mapping).

In certain aspects, competition binding assays can be used to determine whether an antibody is competitively blocked, e.g., in a dose dependent manner, by another antibody for example, an antibody binds essentially the same epitope, or overlapping epitopes, as a reference antibody, when the two antibodies recognize identical or sterically overlapping epitopes in competition binding assays such as competition ELISA assays, which can be configured in all number of different formats, using either labeled antigen or labeled antibody. In a particular embodiment, an antibody can be tested in competition binding assays with an antibody described herein (e.g. 1901-1A, 1901-1B, 1901-1C, 1901-1D)

In addition, antibodies that recognize and bind to the same or overlapping epitopes of TGF-β3 (e.g., human TGF-β3) can be identified using routine techniques such as an immunoassay, for example, by showing the ability of one antibody to block the binding of another antibody to a target antigen, i.e., a competitive binding assay. Competition binding assays also can be used to determine whether two antibodies have similar binding specificity for an antigen or an epitope, including a particular epitope on an antigen or protein target. Competitive binding can be determined in an assay in which the immunoglobulin under test inhibits specific binding of another antibody to a common antigen or target antigen. In an aspect, in competition binding, the binding of an antibody or antigen-binding fragment of the present invention, including a TGFβ3 antibody described herein, for example including 1901-1A, 1901-1B, 1901-1C, or 1901-1D, is reduced in the presence of the immunoglobulin under test, and thus competitive binding is assessed and determined and/or confirmed.

In certain aspects, competition binding assays can be used to determine whether an antibody is competitively blocked, e.g., in a dose dependent manner, by another antibody for example, an antibody binds essentially the same epitope, or overlapping epitopes, as a reference antibody, when the two antibodies recognize identical or sterically overlapping epitopes in competition binding assays such as competition ELISA assays, which can be configured in all number of different formats, using either labeled antigen or labeled antibody. In a particular embodiment, an antibody can be tested in competition binding assays with a TGF-β3 antibody described herein, for example including 1901-1A, 1901-1B, 1901-1C, or 1901-1D. Competition binding assays are well known in the art. Exemplary competitive binding assays are provided herein. For example, competition is demonstrated between antibodies herein, including as described in the examples and figures.

In specific aspects, provided herein are antibodies, or antigen-binding fragments thereof, which binds to the same epitope as that of an antibody (e.g., any one of antibodies 1901-1A, 1901-1B, 1901-1C, or 1901-1D) comprising the amino acid sequences described herein (see, e.g., FIG. 7, 8, 10, 11, 12 or 13) for specific binding to TGF-β3 (e.g., human TGF-β3). In specific aspects, provided herein are antibodies, or an antigen-binding fragments thereof, which bind to an overlapping epitope with that of an antibody (e.g., any one of antibodies 1901-1A, 1901-1B, 1901-1C, or 1901-1D) comprising the amino acid sequences described herein (see, e.g., FIG. 7, 8, 10, 11, 12 or 13) for specific binding to TGF-β3 (e.g., human TGF-β3). Assays known to one of skill in the art or described herein (e.g., X-ray crystallography, ELISA assays, etc.) can be used to determine if two antibodies bind to the same epitope. Biacore assays can be used to assess and determine competitive binding and also epitope binding. Biacore can be utilized to determine the extent to which different antibodies interact with a single antigen or epitope, to assess protein or antibody-protein interactions, and to determine binding affinity.

TGF-β3 plays an important role in controlling the immune system and is a tumor promoter and a tumor suppressor. Studies of TGF-β3 in cancer provide a rational for blocking TGF-β3 signaling in human cancers for therapeutic effect. Overexpression of TGF-β ligands have been reported in most cancers, including in tumors resistant to conventional chemotherapy, and high levels of these in tumor tissues and/or serum are associated with early metastatic recurrences and/or poor patient outcome (Teicher, B. A. et al (1997) In Vivo 11:463-472; Wojtowicz-Praga, S. (2003) Invest New Drugs 21:21-32; Ito, N., et al. (1995) Cancer Lett 89:45-48; Shariat, S. F., et al (2001) Cancer 92:2985-2992; Shariat, S. F., et al (2001) J Clin Oncol 19:2856-2864; Tsushima, H., et al (2001) Clin Cancer Res 7:1258-1262; Rich, J. N. (2003) Front Biosci 8:e245e260). Animal studies with pan-TGF-β antibody have shown inhibition of tumor recurrence or metastasis in fibrosarcoma, colon cancer, and breast cancer (Terabe M et al (2003) J Exp Med 198:1741-1752; Nam J-S et al (2008) Cancer Res 68(10):3835-3843), and reduced radiation-induced acceleration of metastatic breast cancer (Biswas S et al (2007) 117:1305-1313). Evidence to date strongly supports that blocking TGFβ can enhance antigen uptake, presentation, and activation of antitumor immune response mediated by therapeutic vaccines. Indeed, recent studies have demonstrated that blockade of TGF-β, using mouse TGF-β generic antibody ID11 (which recognizes TGF-β1, TGF-β2 and TGF-β3), synergistically enhances tumor vaccines in animal models via CD8$^+$ T cells (Terabe M et al (2009) Clin Cancer Res 15:6560-6569; Takaku S et al (2010) Int J Cancer 126(7):1666). Radiation therapy has the potential to convert the irradiated tumor into an in situ vaccine (Formanti S C et al (2012) Int J Radiat Oncol Biol Phys 84:870-880). In recent studies, nonspecific TGF-β neutralizing antibody (1D11) administered during radiation therapy increased the ability of the therapy to induce T-cell responses to endogenous tumor antigens in preclinical models of metastatic breast cancer (Vanpoille-Box C et al (2015) Cancer Res 75(11):2232-2242). Additional blockade of PD-1 enhanced the effectiveness of radiation therapy with TGF-β antibody.

TGF-β antibodies have been generated and a particular example denoted 1D11, and its humanized counterpart GC1008, have been evaluated in animal models and early human clinical trials and are provided and disclosed in patent applications including in WO2007076391, WO2005097832, WO2006086469 and U.S. Pat. No. 5,571,714. Antibody 1D11 and its humanized counterpart, however, are generic TGF-beta antibodies, recognizing all TGF-β forms including TGF-β1, TGF-β2 and TGF-β3. Antibody 1D11 and its humanized counterpart do not, therefore, provide specific and directed modulation of TGF-β3.

Monocolonal antibodies derived by hybridoma technique from another species than human, such as mouse, can be humanized, which means that a non-human antibody is genetically engineered to be more human in order to avoid HAMA when infused into humans. Methods for humanization of antibodies are well known within the art, among the more common methods are complementarity-determining region (CDR) grafting and veneering (also known as resurfacing). These methods have been extensively described in the literature and in patents, see e.g.; King "Applications and Engineering of Monoclonal Antibodies" Taylor & Francis, 1998; U.S. Pat. Nos. 5,225,539; 5,530,101; 5,585,089, 5,859,205 and 6,797,492, each incorporated herein by reference. Another common method is the veneering (v) technology (Daugherty et al. (1991). Nucleic Acids Res. 19(9), 2471-6; U.S. Pat. No. 6,797,492; Padlan, E. A. (1991) Mol. Immunol. 28(4-5), 489-98; European Patent No. 519596). Where a replacement of the surface-exposed residues in the framework regions, which differ from those usually found in human antibodies, is performed in order to minimize the immunogenicity of an antibody's variable domains, while preserving ligand-binding properties.

Antibodies including fragments thereof may possess certain diagnostic applications and may for example, be utilized for the purpose of detecting and/or measuring conditions such as cancer, precancerous lesions, conditions related to or resulting from hyperproliferative cell growth or the like.

The radiolabelled specific binding members, particularly antibodies and fragments thereof, are useful in in vitro diagnostics techniques and in in vivo radioimaging techniques and in radioimmunotherapy. In the instance of in vivo imaging, the specific binding members of the present invention may be conjugated to an imaging agent rather than a radioisotope(s), including but not limited to a magnetic resonance image enhancing agent, wherein for instance an antibody molecule is loaded with a large number of paramagnetic ions through chelating groups. Examples of chelating groups include EDTA, porphyrins, polyamines crown ethers and polyoximes. Examples of paramagnetic ions include gadolinium, iron, manganese, rhenium, europium, lanthanium, holmium and ferbium. In a further aspect of the invention, radiolabelled specific binding members, particularly antibodies and fragments thereof, particularly radioimmunoconjugates, are useful in radioimmunotherapy, particularly as radiolabelled antibodies for cancer therapy. In a still further aspect, the radiolabelled specific binding members, particularly antibodies and fragments thereof, are useful in radioimmuno-guided surgery techniques, wherein they can identify and indicate the presence and/or location of cancer cells, precancerous cells, tumor cells, and hyperproliferative cells, prior to, during or following surgery to remove such cells.

Immunoconjugates or antibody fusion proteins of the present invention, wherein the specific binding members, particularly antibodies and fragments thereof, of the present invention are conjugated or attached to other molecules or agents further include, but are not limited to binding members conjugated to a chemical ablation agent, toxin, immunomodulator, cytokine, cytotoxic agent, chemotherapeutic agent or drug.

Radioimmunotherapy (RAIT) has entered the clinic and demonstrated efficacy using various antibody immunoconjugates. $^{131}$I labeled humanized anti-carcinoembryonic antigen (anti-CEA) antibody hMN-14 has been evaluated in colorectal cancer (Behr T M et al (2002) Cancer 94(4Suppl): 1373-81) and the same antibody with $^{90}$Y label has been assessed in medullary thyroid carcinoma (Stein R et al (2002) Cancer 94(1):51-61). Radioimmunotherapy using monoclonal antibodies has also been assessed and reported for non-Hodgkin's lymphoma and pancreatic cancer (Goldenberg D M (2001) Crit Rev Oncol Hematol 39(1-2):195-201; Gold D V et al (2001) Crit Rev Oncol Hematol 39 (1-2) 147-54). Radioimmunotherapy methods with particular antibodies are also described in U.S. Pat. Nos. 6,306,393 and 6,331,175. Radioimmunoguided surgery (RIGS) has also entered the clinic and demonstrated efficacy and usefulness, including using anti-CEA antibodies and antibodies directed against tumor-associated antigens (Kim J C et al (2002) Int J Cancer 97(4):542-7; Schneebaum S et al (2001) World J Surg 25(12):1495-8; Avital S et al (2000) Cancer 89(8): 1692-8; McIntosh D G et al (1997) Cancer Biother Radiopharm 12 (4):287-94).

Adoptive cell transfer (ACT) is emerging as a new pillar in cancer therapy, based on collecting and using patients' own immune cells to treat their cancer. There are several types of ACT, including TILs, TCRs, and CARs (Haanen et al. (2018) J Immunother Cancer 474:449-461). One approach uses immune cells that have penetrated the environment in and around the tumor, known as tumor-infiltrating lymphocytes (TILs). Another approach to ACT involves engineering patients' T cells to express a specific T-cell receptor (TCR) to recognize tumor cell antigens (Mackall et al (2019) Nature Medicine 25:1341-1355). Chimeric antigen receptors (CARs) use portions of synthetic antibodies directed against specific surface cell antigens and CAR T cell therapy has advanced significantly in clinical development. In CAR therapy, T cells are isolated from a patient and genetically engineered to produce CARs so the T cells recognize and attach to a specific antigen on tumor cells. CAR T cell therapy directed against B cell antigen 01319 has demonstrated success in children and young adults with ALL and also in lymphoma patients.

The TGF-β3 antibody of the invention, or a fragment thereof, may further be used for constructing a chimeric antigen receptor (CAR), wherein the CAR comprises the antigen binding domain of the TGF-β3 antibody, a transmembrane domain, a costimulatory signaling region, and a signaling domain. In these and other embodiments, the antigen binding domain may be a Fab or a scFv of the TGF-β3 antibody. In yet a further embodiment, TGF-β3 is present in a tumor microenvironment or on cells in the tumor microenvironment. In yet other embodiments, the costimulatory signaling region comprises the intracellular domain of a costimulatory molecule selected from the group consisting of CD27, CD28, 4-1BB, OX40, CD30, CD40, PD-1, ICOS, lymphocyte function-associated antigen-1 (LFA-1), CD2, CD7, LIGHT, NKG2C, B7-H3, a ligand that specifically binds with CD83, and any combination thereof.

T-cells modified to express chimeric antigen receptor (CAR) and administered alone have been subject to suppression within the hostile tumor microenvironment. As a way of a non-limiting example, further modification of these cells to express secretable scFvs (eg, PD-1, PDL-1, or CTLA-4) (known as Armored CARs) have improved anti-tumor function due to their ability to modulate the tumor microenvironment and resist suppressive factors (for example as described in U.S. Pat. No. 10,124,023 and Brentjens et al (2018) Nat Biotechnol 36(9):847-856). In one such embodiment Armored CARs expressing one or more TGF-β3 antibody of the present invention, including one or more scfv thereof, are contempated, wherein the TGF-β3 antibody enhances the CAR cells activity and blocks immune suppression, including such as suppression by endogenous TGF-β. In another embodiment, the TGF-β3 antibody of the invention could be used in Adoptive Cell Therapy (ACT) where the TGF-β3 antibody, or fragments thereof, would be genetically introduced into T-cells, preferably but not limited to, tumor infiltrating lymphocytes (TILs), isolated from cancer patients, and then such T-cells would be expanded and delivered back into the patients whereby the T-cells would target the tumor and express and secrete the TGF-β antibody, or fragment thereof, in the local tumor microenvironment to counter the immunosuppressive environment there. In another embodiment, exogenous TGF-β3 antibody, or a fragments thereof, can be added to the expanded T-cell population when delivering back into the patients for ACT. As a way of a non-limiting example, exogenous TGF-β3 antibody, or a fragment(s) thereof, can be added to a T-cell population expanded as detailed in WO 2019/086711 before delivery back into the patients for ACT.

The TGF-β3 antibody of the invention could also be used in Adoptive Cell Therapy (ACT) where the TGF-β3 antibody, or fragments thereof, would be genetically introduced into T-cells isolated from cancer patients, and then such T-cells would be expanded and delivered back into a patient whereby the T-cells would target the tumor and express the TGF-β3 antibody, or fragment thereof, in the local tumor microenvironment to counter the immonusuppressive environment there. Preferably the T-cells used would tumor infiltrating lymphocytes (TILs).

In vivo animal models of cancer or animal xenograft studies may be utilized by the skilled artisan to further or additionally screen, assess, and/or verify the specific binding members and antibodies or fragments thereof of the present invention, including further assessing TGF-β3 modulation and inhibition in vivo and inhibiting tumor progression, recurrence, metastasis, or immune response against tumor cells or response to antigens or vaccines, including tumor or cancer antigens or vaccines. Such animal models include, but are not limited to models of immune response, immune modulation, vaccination, cancer, cancer metastasis. Models of cancers whose recurrence or metastasis are associated with elevated levels of TGF-β3 are particularly susceptible to and targeted by the antibodies of the present invention. Such cancers include melanomas, breast, lung and prostate cancer. Exemplary and suitable models are known and readily available to the skilled artisan and include those referenced and/or described herein and known in the art. For example, antibodies or active fragments thereof of the invention may be evaluated in breast cancer models, including tumorigenicity of human breast cancer cells in athymic mice (Arteaga C L et al (1993) Cell Growth Diff 4:193-201) or in Neu-induced mammary tumors (Muraoka-Cok R S et al (2004) Cancer Res 64:2002-2011), or in evaluating metastases of transgenic mammary tumors (Siegel P M et al (2003) Proc Natl Acad Sci USA 100:8430-8435). Also, as an example the anti-tumor effect of TGF-β3 antibody can be examined on a whole cell vaccine in prophylaxis against injected CT26 colon carcinoma tumors in syngeneic mice using a method similar to that reported by Takaku et al (Takaku S et al (2010) Int J Cancer 126(7): 1666).

Antibodies of the present invention may be administered to a patient in need of treatment via any suitable route, including by injection, including intreperitoneally, intramuscularly, subcutaneous, intravenous, into the bloodstream or CSF, or directly into the site of the tumor or by intratumoral administration or intratumoral injection. The precise dose will depend upon a number of factors, including whether the antibody is for diagnosis or for treatment, the size and location of the tumor, the precise nature of the antibody (whether whole antibody, fragment, diabody, etc), and the nature of the detectable or functional label attached to the antibody. Where a radionuclide is used for therapy, a suitable single dose may be about 45 $mCi/m^2$, to a maximum of about 250 $mCi/m^2$. Preferable dosage is in the range of 15 to 40 mCi, with a further preferred dosage range of 20 to 30 mCi, or 10 to 30 mCi. Such therapy may require bone marrow or stem cell replacement. A typical antibody dose for either tumor imaging or tumor treatment will be in the range of from 0.5 to 40 mg, preferably from 1 to 4 mg of antibody in F(ab')2 form. Naked antibodies are preferably administered in doses of 20 to 1000 mg protein per dose, or 20 to 500 mg protein per dose, or 20 to 100 mg protein per dose. This is a dose for a single treatment of an adult patient, which may be proportionally adjusted for children and infants, and also adjusted for other antibody formats, in proportion for example to molecular weight. Treatments may be repeated at daily, twice-weekly, weekly or monthly intervals, at the discretion of the physician.

Pharmaceutical and Therapeutic Compositions

Antibodies and fragments of the present invention will usually be administered in the form of a pharmaceutical composition, which may comprise at least one component in addition to the specific binding member. Thus pharmaceutical compositions according to the present invention, and for use in accordance with the present invention, may comprise, in addition to active ingredient, a pharmaceutically acceptable excipient, carrier, buffer, stabiliser or other materials well known to those skilled in the art. Such materials should be non-toxic and should not interfere with the efficacy of the active ingredient. The precise nature of the carrier or other material will depend on the route of administration, which may be oral, or by injection, e.g. intravenous, or by deposition at a tumor site.

The binding members and antibodies of the present invention, and in a particular embodiment the antibody having sequence represented in FIGS. 7, 8, 10, 11, 12, or active fragments thereof, and single chain, recombinant or synthetic antibodies derived therefrom, and particularly antibody comprising the heavy chain CDR region sequences and the light chain CDR region sequences depicted in FIGS. 7 and 8 or in FIGS. 10, 11, 12 13 or in SEQ ID NOS: 1, 34, 35, 28, 29, 30, 37, 4, 5, 6, 31, 32, 33, can be prepared in pharmaceutical compositions, including a suitable vehicle, carrier or diluent, or including an adjuvant and/or immune modulator, for administration in instances wherein therapy is appropriate, such as to treat cancer or stimulate or enhance immune response, including immune response against cancer. Such pharmaceutical compositions may also include means for modulating the half-life of the binding members, antibodies or fragments by methods known in the art such as pegylation. Such pharmaceutical compositions may further comprise additional antibodies or therapeutic agents.

A composition of the present invention may be administered alone or in combination with other treatments, therapeutics or agents, either simultaneously or sequentially dependent upon the condition to be treated. In addition, the present invention contemplates and includes compositions comprising the binding member, particularly antibody or fragment thereof, herein described and other agents or therapeutics such as anti-cancer agents or therapeutics, anti-mitotic agents, apoptotic agents or antibodies, or immune modulators, or small molecule inhibitors to immune modulators. More generally these anti-cancer agents may be tyrosine kinase inhibitors or phosphorylation cascade inhibitors, post-translational modulators, cell growth or division inhibitors (e.g. anti-mitotics), inhibitors or signal transduction inhibitors. Other treatments or therapeutics may include the administration of suitable doses of pain relief drugs such as non-steroidal anti-inflammatory drugs (e.g. aspirin, paracetamol, ibuprofen or ketoprofen) or opiates such as morphine, or anti-emetics. In addition, the composition may be administered with immune modulators, such as α-galactosyl ceramide, interleukins, tumor necrosis factor (TNF) or other growth factors, colony stimulating factors, cytokines or hormones which stimulate the immune response and reduction or elimination of cancer cells or tumors. The composition may be administered with an immune modulator such as an adjuvant. The composition may also be administered with, or may include combinations along with other anti-TGFβ antibodies, other immunomodulatory antibodies or other anti-tumor antigen antibodies. In an aspect, the composition is administered in combination with another antibody, particularly an anti-tumor antigen antibody.

The present invention also includes antibodies and fragments thereof, which are covalently attached to or otherwise associated with other molecules or agents. These other molecules or agents include, but are not limited to, molecules (including antibodies or antibody fragments) with distinct recognition characteristics, toxins, ligands, and chemotherapeutic agents. In an additional aspect, the antibodies or fragments of the invention may be used to target or direct therapeutic molecules or other agents, for example to target molecules or agents to TGFβ expressing cells, or TGFβ responsive cells, particularly TGF-β3 expressing or responsive cells, for example cells at wound sites, tumor sites, inflammatory areas or cancerous lesions.

Pharmaceutical compositions for oral administration may be in tablet, capsule, powder or liquid form. A tablet may comprise a solid carrier such as gelatin or an adjuvant. Liquid pharmaceutical compositions generally comprise a liquid carrier such as water, petroleum, animal or vegetable oils, mineral oil or synthetic oil. Physiological saline solution, dextrose or other saccharide solution or glycols such as ethylene glycol, propylene glycol or polyethylene glycol may be included.

For intravenous, injection, or injection at the site of affliction, the active ingredient may be in the form of a parenterally acceptable aqueous solution which is pyrogen-free and has suitable pH, isotonicity and stability. Those of relevant skill in the art are well able to prepare suitable solutions using, for example, isotonic vehicles such as Sodium Chloride Injection, Ringer's Injection, Lactated Ringer's Injection. Preservatives, stabilisers, buffers, antioxidants and/or other additives may be included, as required.

A composition may be administered alone or in combination with other treatments, therapeutics or agents, either simultaneously or sequentially dependent upon the condition to be treated. In addition, the present invention contemplates and includes compositions comprising the binding member, particularly antibody or fragment thereof, herein described and other agents or therapeutics such as anti-cancer agents or therapeutics, hormones, anti-mitotic agents, anti-apoptotic agents, antibodies, or immune modulators. More generally these anti-cancer agents may be but are not limited to tyrosine kinase inhibitors or phosphorylation cascade inhibitors, post-translational modulators, cell growth or division inhibitors (e.g. anti-mitotics), or signal transduction inhibitors. Other treatments or therapeutics may include the administration of suitable doses of pain relief drugs such as non-steroidal anti-inflammatory drugs (e.g. aspirin, paracetamol, ibuprofen or ketoprofen) or opiates such as morphine, or anti-emetics. The composition can be administered in combination (either sequentially (i.e. before or after) or simultaneously) with tyrosine kinase inhibitors (including, but not limited to AG1478 and ZD1839, STI571, OSI-774, SU-6668), doxorubicin, temozolomide, cisplatin, carboplatin, nitrosoureas, procarbazine, vincristine, hydroxyurea, 5-fluoruracil, cytosine arabinoside, cyclophosphamide, epipodophyllotoxin, carmustine, lomustine, and/or other chemotherapeutic agents. Thus, these agents may be specific anti-cancer agents, or immune cell response modulators or may be more general anti-cancer and anti-neoplastic agents such as doxorubicin, cisplatin, temozolomide, nitrosoureas, procarbazine, vincristine, hydroxyurea, 5-fluoruracil, cytosine arabinoside, cyclophosphamide, epipodophyllotoxin, carmustine, or lomustine. In addition, the composition may be administered with hormones such as dexamethasone, immune modulators, such as interleukins, tumor necrosis factor (TNF) or other growth factors, colony stimulating factors, cytokines, agonist or antagonist antibodies to regulators of immune response which stimulate, enhance, or derepress the immune response and reduction or elimination of cancer cells or tumors. The composition may also be administered with, or may include combinations along with other anti-tumor antigen antibodies.

In addition, the present invention contemplates and includes therapeutic compositions for the use of the antibody(ies) or fragments in combination with conventional radiotherapy.

The present invention further contemplates therapeutic compositions useful in practicing the therapeutic methods of this invention. A subject therapeutic composition includes, in admixture, a pharmaceutically acceptable excipient (carrier) and one or more of a specific binding member or antibody, polypeptide analog thereof or fragment thereof, as described herein as an active ingredient. In an embodiment, the composition comprises an antigen capable of modulating the specific binding of the present binding member/antibody with a target cell. In an embodiment the composition comprises an antigen or vaccine formulation, particularly a tumor antigen or cancer vaccine.

The preparation of therapeutic compositions which contain polypeptides, analogs or active fragments as active ingredients is well understood in the art. Typically, such compositions are prepared as injectables, either as liquid solutions or suspensions. However, solid forms suitable for solution in, or suspension in, liquid prior to injection can also be prepared. The preparation can also be emulsified. The active therapeutic ingredient is often mixed with excipients which are pharmaceutically acceptable and compatible with the active ingredient. Suitable excipients are, for example, water, saline, dextrose, glycerol, ethanol, or the like and combinations thereof. In addition, if desired, the composition can contain minor amounts of auxiliary substances such as wetting or emulsifying agents, pH buffering agents which enhance the effectiveness of the active ingredient.

A polypeptide, analog or active fragment can be formulated into the therapeutic composition as neutralized pharmaceutically acceptable salt forms. Pharmaceutically acceptable salts include the acid addition salts (formed with the free amino groups of the polypeptide or antibody molecule) and which are formed with inorganic acids such as, for example, hydrochloric or phosphoric acids, or such organic acids as acetic, oxalic, tartaric, mandelic, and the like. Salts formed from the free carboxyl groups can also be derived from inorganic bases such as, for example, sodium, potassium, ammonium, calcium, or ferric hydroxides, and such organic bases as isopropylamine, trimethylamine, 2-ethylamino ethanol, histidine, procaine, and the like.

An alternative paradigm for cancer therapy utilizing intratumoral immunomodulation and intratumoral immunization has been described and reviewed (Marabelle A et al (2014) Clin Cancer Res 20(7):1747-1756). This paradigm may be particularly effective for drug therapies designed to interact with molecules playing a role in the activation of immune cells to reverse cancer-induced immunotolerance and facilitate antitumor immune response, including immunostimulator monoclonal antibodies (Marabelle A et al (2014) Clin Cancer Res 20(7):1747-1756; Mellman I et al (2011) Nature 480:480-489). Application of this paradigm to the antibodies and active fragments of the present invention is an aspect of this invention. Delivery of immunostimulatory monoclonal antibodies directly into the tumor to generate or facilitate a systemic antitumor immune response, including a more potent antitumor response causing less autoimmune toxicity or other side effects and the need for less drug than systemically administered drugs or antibodies, Antibody delivery in adjuvant around established tumor (anti-CTLA-4 Ab delivered in water-in-oil emulsion adjuvant (Montadine ISA51) around colon carcinoma tumor) eradicated the local tumor and prevented distinct tumor development (Fransen M F et al (2013) Cancer Res 19:5381-5389).

The compositions are administered in a manner compatible with the dosage formulation, and in a therapeutically effective amount. The quantity to be administered depends on the subject to be treated, capacity of the subject's immune system to utilize the active ingredient, and degree of peptide/MHC or tumor antigen binding capacity desired. Precise amounts of active ingredient required to be administered depend on the judgment of the practitioner and are peculiar to each individual. Suitable regimes for initial administration and follow on administration are also variable, and may include an initial administration followed by repeated doses at one or more hour intervals by a subsequent injection or other administration. Alternatively, continuous intravenous infusion sufficient to maintain appropriate and sufficient concentrations in the blood or at the site of desired therapy is contemplated.

Diagnostic Assays

The present invention also relates to a variety of diagnostic applications, including methods for detecting the expression of or elevated presence of TGF-β3, TGF-β3-mediated cancer, or cancer more generally, evaluating the presence or amount of TGF-β3-responsive cells, by reference to their ability to be recognized by the present specific binding member(s). Peptide complexes can be identified, targeted, labeled, and/or quantitated on cells, including immune cells and/or tumor cells.

Diagnostic applications of the specific binding members of the present invention, particularly antibodies and fragments thereof, include in vitro and in vivo applications well known and standard to the skilled artisan and based on the present description. Diagnostic assays and kits for in vitro assessment and evaluation of tumor and cancer status, and tumor response or immune response, may be utilized to diagnose, evaluate and monitor patient samples including those known to have or suspected of having cancer, a precancerous condition, a condition related to hyperproliferative cell growth or from a tumor sample. The assessment and evaluation of cancer, tumor and metastatic disease status is also useful in determining the suitability of a patient for a clinical trial of a drug or for the administration of a particular chemotherapeutic agent or specific binding member, particularly an antibody, of the present invention, including combinations thereof, versus a different agent or binding member. This type of diagnostic monitoring and assessment is already in practice utilizing antibodies against the HER2 protein in breast cancer (Hercep Test, Dako Corporation), where the assay is also used to evaluate patients for antibody therapy using Herceptin. In vivo applications include imaging of tumors or assessing cancer status of individuals, including radioimaging.

Preferably, the antibody used in the diagnostic methods of this invention is mouse, human, humanized or recombinant antibody. Preferably, the antibody is a single chain antibody or domain antibody. In addition, the antibody molecules used herein can be in the form of Fab, Fab', $F(ab')_2$ or F(v) portions of whole antibody molecules, particularly Fab.

The presence of TGF-β3 in cells or TGF-β3 responsive cells or TGF-β3 responsive genes or proteins can be ascertained by the usual in vitro or in vivo immunological procedures applicable to such determinations. A number of useful procedures are known. The procedures and their application are all familiar to those skilled in the art and accordingly may be utilized within the scope of the present invention.

In a further embodiment of this invention, commercial test kits suitable for use by a medical specialist may be prepared to determine the presence or absence of aberrant expression of including but not limited to amplified TGF-β3, in suspected target cells. In accordance with the testing techniques discussed above, one class of such kits will contain at least the labeled or its binding partner, for instance an antibody specific thereto, and directions, of course, depending upon the method selected. The kits may also contain peripheral reagents such as buffers, stabilizers, etc.

Accordingly, a test kit may be prepared for the demonstration of the presence of or elevated levels of TGF-β3 or a TGF-β3-responsive element or protein, comprising:

(a) a predetermined amount of at least one labeled immunochemically reactive component obtained by the direct or indirect attachment of the present specific binding member or a specific binding partner thereto, to a detectable label;
(b) other reagents; and
(c) directions for use of said kit.

A test kit may be prepared for the demonstration of the presence of TGF-β3-mediated cancer, particularly selected from breast, lung, liver, prostate, bladder cancer comprising:

(a) a predetermined amount of at least one labeled immunochemically reactive component obtained by the direct or indirect attachment of the present specific binding member or a specific binding partner thereto, to a detectable label;
(b) other reagents; and
(c) directions for use of said kit.

In accordance with the above, an assay system for screening potential drugs effective to modulate the presence or activity of TGF-β3 and/or the activity or binding of the antibody of the present invention may be prepared. The antigen peptide or the binding member or antibody may be introduced into a test system, and the prospective drug may also be introduced into the resulting cell culture, and the culture thereafter examined to observe any changes in the activity of the cells, binding of the antibody, or amount and extent of TGF-β3 due either to the addition of the prospective drug alone, or due to the effect of added quantities of the known agent(s).

Nucleic Acids

The present invention further provides an isolated nucleic acid encoding a specific binding member of the present invention. Nucleic acid includes DNA and RNA. In a preferred aspect, the present invention provides a nucleic acid which codes for a polypeptide of the invention as defined above, including a polypeptide as set out in FIGS. 7, 8, 10, 11, 12 and/or 13, including a polypeptide of SEQ ID NO: 18, 19, 36, 22, and/or 23, or capable of encoding the CDR regions thereof, including SEQ ID NOs: 1, 34, 35, 30, 28, 29, 4, 5, 6, 33, 31 and/or 32.

The present invention also provides constructs in the form of plasmids, vectors, transcription or expression cassettes which comprise at least one polynucleotide as above. The present invention also provides a recombinant host cell which comprises one or more constructs as above. A nucleic acid encoding any specific binding member as provided itself forms an aspect of the present invention, as does a method of production of the specific binding member which method comprises expression from encoding nucleic acid therefor. Expression may conveniently be achieved by culturing under appropriate conditions recombinant host cells containing the nucleic acid. Following production by expression a specific binding member may be isolated and/or purified using any suitable technique, then used as appropriate.

Specific binding members and encoding nucleic acid molecules and vectors according to the present invention may be provided isolated and/or purified, e.g. from their natural environment, in substantially pure or homogeneous form, or, in the case of nucleic acid, free or substantially free of nucleic acid or genes origin other than the sequence encoding a polypeptide with the required function. Nucleic acid according to the present invention may comprise DNA or RNA and may be wholly or partially synthetic.

Systems for cloning and expression of a polypeptide in a variety of different host cells are well known. Suitable host cells include bacteria, mammalian cells, yeast and baculovirus systems. Suitable vectors can be chosen or constructed, containing appropriate regulatory sequences, including promoter sequences, terminator sequences, polyadenylation sequences, enhancer sequences, marker genes and other sequences as appropriate. Vectors may be plasmids, viral e.g. phage, or phagemid, as appropriate.

Thus, a further aspect of the present invention provides a host cell containing nucleic acid as disclosed herein. A still further aspect provides a method comprising introducing such nucleic acid into a host cell. The introduction may employ any available technique. The introduction may be followed by causing or allowing expression from the nucleic acid, e.g. by culturing host cells under conditions for expression of the gene. The present invention also provides a method which comprises using a construct as stated above in an expression system in order to express a specific binding member or polypeptide as above.

Another feature of this invention is the expression of the DNA sequences disclosed herein. As is well known in the art, DNA sequences may be expressed by operatively linking them to an expression control sequence in an appropriate expression vector and employing that expression vector to transform an appropriate unicellular host. A wide variety of host/expression vector combinations may be employed in expressing the DNA sequences of this invention. Useful expression vectors, for example, may consist of segments of chromosomal, non-chromosomal and synthetic DNA sequences. Suitable vectors include derivatives of SV40 and known bacterial plasmids, e.g., *E. coli* plasmids col El, pCR1, pBR322, pMB9 and their derivatives, plasmids such as RP4; phage DNAs, e.g., the numerous derivatives of phage λ, e.g., NM989, and other phage DNA, e.g., M13 and filamentous single stranded phage DNA; yeast plasmids such as the 2u plasmid or derivatives thereof; vectors useful in eukaryotic cells, such as vectors useful in insect or mammalian cells; vectors derived from combinations of plasmids and phage DNAs, such as plasmids that have been modified to employ phage DNA or other expression control sequences; and the like.

Any of a wide variety of expression control sequences—sequences that control the expression of a DNA sequence operatively linked to it—may be used in these vectors to express the DNA sequences of this invention. Such useful expression control sequences include, for example, the early or late promoters of SV40, CMV, vaccinia, polyoma or adenovirus, the lac system, the trp system, the TAC system, the TRC system, the LTR system, the major operator and promoter regions of phage λ, the control regions of fd coat protein, the promoter for 3-phosphoglycerate kinase or other glycolytic enzymes, the promoters of acid phosphatase (e.g., Pho5), the promoters of the yeast α-mating factors, and other sequences known to control the expression of genes of prokaryotic or eukaryotic cells or their viruses, and various combinations thereof.

A wide variety of unicellular host cells are also useful in expressing the DNA sequences of this invention. These hosts may include well known eukaryotic and prokaryotic hosts, such as strains of *E. coli, Pseudomonas, Bacillus, Streptomyces*, fungi such as yeasts, and animal cells, such as CHO, YB/20, NSO, SP2/0, R1.1, B-W and L-M cells, African Green Monkey kidney cells (e.g., COS 1, COS 7, BSC1, BSC40, and BMT10), insect cells (e.g., Sf9), and human cells and plant cells in tissue culture.

It will be understood that not all vectors, expression control sequences and hosts will function equally well to express the DNA sequences of this invention. Neither will all hosts function equally well with the same expression system. However, one skilled in the art will be able to select the proper vectors, expression control sequences, and hosts without undue experimentation to accomplish the desired expression without departing from the scope of this invention.

As mentioned above, a DNA sequence encoding a specific binding member can be prepared synthetically rather than cloned. The DNA sequence can be designed with the appropriate codons for the specific binding member amino acid sequence. In general, one will select preferred codons for the intended host if the sequence will be used for expression. The complete sequence is assembled from overlapping oligonucleotides prepared by standard methods and assembled into a complete coding sequence. Synthetic DNA sequences allow convenient construction of genes which will express specific binding member analogs or "muteins". Alternatively, DNA encoding muteins can be made by site-directed mutagenesis of native specific binding member genes or cDNAs, and muteins can be made directly using conventional polypeptide synthesis.

The invention may be better understood by reference to the following non-limiting Examples, which are provided as exemplary of the invention. The following examples are presented in order to more fully illustrate the preferred embodiments of the invention and should in no way be construed, however, as limiting the broad scope of the invention.

Example 1

Murine TGF Beta-3 Antibodies

Mature mouse and human TGF-ß3 share 100% homology at the protein level which makes it extremely difficult to generate mouse antibodies against both the human and the mouse protein due to immune tolerance. The mouse and human TGF-ß3 amino acid sequences are as follows:

```
Mouse
NCBI Reference Sequence: NP_033394.2
                                  (SEQ ID NO: 7)
aldtnycfrn leenccvrpl yidfrqdlgw

kwvhepkgyy anfcsgpcpy lrsadtthst

vlglyntlnp easaspccvp qdlepltily

yvgrtpkveq lsnmvvksck cs
```

-continued

```
Human
 UniProtKB/Swiss-Prot: P10600.1
                                (SEQ. ID NO: 8)
aldtnycfrn leenccvrpl yidfrqdlgw

kwvhepkgyy anfcsgpcpy lrsadtthst

vlglyntlnp easaspccvp qdlepltily

yvgrtpkveq lsnmvvksck cs
```

TGF-ß3 antibodies were successfully generated previously in mice using an auto-vaccination protocol. A group of mouse anti-TGF-ß3 antibodies were isolated: MTGF-ß3-9/8 (also denoted as MTGF-ß3-9), MTGF-ß3-1203/11 (also denoted as MTGF-ß3-12), MTGF-ß3-1679/2 (also denoted as MTGF-ß3-16), MTGF-ß3-1719/13 (also denoted as MTGF-ß3-17), MTGF-ß3-1901/16 (also denoted as MTGF-ß3-19). The antibodies are all IgG class antibodies; MTGF-ß3-19 an IgG1 antibody, antibodies MTGF-ß3-9, MTGF-ß3-16 and MTGF-ß3-17 are IgG2a antibodies, and antibody MTGF-ß3-12 is an IgG2b. The antibodies, their specificity for TGF-β3 binding and neutralization, and their sequences are described and provided in PCT/US2016/036965, published as WO2016/201282 and U.S. Ser. No. 15/580,746, published as US2018-0148501 A1, which are incorporated herein by reference.

Mouse monoclonal antibody MTGF-ß3-1901/16 (also denoted as MTGF-ß3-19) and particularly denoted herein as antibody 1901 was selected for further development and chimerization and humanization as described in the following examples. TGFβ3 antibody 1901 (MTGF-ß3-1901/16) has a heavy chain variable region sequence comprising a CDR1 sequence SSWIH (SEQ ID NO:1), a CDR2 sequence RIYPGDGDTNYTGKFKG (SEQ ID NO:2), and a CDR3 sequence RMITTQAAMDY (SEQ ID NO:3), and a light chain variable region comprising a CDR1 sequence KASQSVINAVA (SEQ ID NO:4), a CDR2 sequence YASNRYT (SEQ ID NO:5), and a CDR3 sequence QQDYSSPT (SEQ ID NO:6).

Example 2

TGFb signaling, particularly TGF-b3 signaling, in the tumor microenvironment is involved in the negative regulation of effective immune responses to cancer through multiple mechanisms. TGFb blockade may overcome this immune suppression especially when combined with other checkpoint targeting drugs. This is an emerging and promising therapeutic approach in immune oncology. A series of mouse monoclonal antibodies to TGFb were previously generated by immunizing mice with recombinant murine TGF protein isoforms, TGFb1, TGFb2 and TGFb3. Mouse monoclonal antibody clone 1901 was selected for further development based on its highly selective specificity for both human and mouse TGFb3 but not TGFb1 and TGFb2 and its capability to block TGFb3 signaling in vitro and in-vivo potency assays (US 2018/0148501 A1).

A project was initiated for the generation of humanized versions of the mouse TGFb3 antibody 1901 with similar or improved functional in vitro potency as the original mouse mAb. Humanized antibodies could be more acceptable and useful in therapeutic approaches in humans. Employing CDR/FR grafting and functional potency assay-driven sequence mutagenesis technologies, we engineered a series of humanized versions based from the murine mAb 1901. In brief, antibodies were at first expressed as scFv in *E. coli* for initial screening for binding to TGFb3 and then as full length human IgG1 or IgG4 antibodies in a transient mammalian cell system. Purified antibodies were screened by ELISA for blocking murine 1901 binding to TGFb3 and for their in vitro potency to inhibit TGFb induced signaling in a reporter cell line (TMLEC assay). Functional potency assays were performed independently in two laboratories. From this screening, four IgG4 antibodies, LCR1901_VH_1G10m-LCR1901_VK_GLv1_03(F) (1901-1C), LCR1901_VH_1G10m-LCR1901_VK_GLv1_05(H) (1901-1A), LCR1901_VH_1G10m_03(K)-LCR1901_VK_GLv1_03 (F) (1901-1D) and LCR1901_VH_1G10m_03(K)-LCR1901_VK_GLv1_05(H) (1901-1B) with significant higher potency to functionally inhibit TGFb3 signaling in TMLEC were selected for extended in vitro characterization, including binding specificity, binding kinetics, structural and physicochemical characteristics such as small scale expression yields, SEC profiles and thermal stability. Notably, these antibodies are more potent than the original mouse 1901 antibody and also have distinct CDR sequences compared to the mouse 1901 antibody. Thus, new antibodies which are humanized and have novel and distinct heavy and light chain CDRs and which are specific for TGF-β3 have been generated. Based on the characterization profile, antibody LCR1901_VH_1G10m_03(K)-LCR1901_VK_GLv1_05(H) (LCR1901-1B) and antibody LCR1901_VH_1G10m-LCR1901_VK_GLv1_03(F) (LCR1901-1C) were selected for further development.

The detailed Materials and Methods for this Example and the following Examples herein are provided below:

Materials and Methods

Cloning of LCR1901 as scFvs into the pCHV101 Phage Display Vector

VH and VK chains of parental mouse LCR1901 anti-TGFb3 mAb and their humanized CDR-grafted GLv1 variants were designed and synthesized as single open reading frame scFvs and cloned into a phagemid vector (pCHV101). scFv host vectors were digested as follows to liberate the scFv inserts:

| | |
|---|---|
| scFv host vector | 2 µg |
| 10X CutSmart Buffer | 3 µl (1X) |
| Nco1-HF (NEB, Cat #R3193S) | 1 µl (20 units) |
| Sal1-HF (NEB, Cat #R3138S) | 1 µl (20 units) |
| Nuclease-free water | To 30 µl |

The pCHV101 phagemid vector was similarly digested:

| | |
|---|---|
| pCHV101 vector | 2 µg |
| 10X CutSmart Buffer | 3 µl (1X) |
| Nco1-HF (NEB, Cat #R3193S) | 1 µl (20 units) |
| Sal1-HF (NEB, Cat #R3138S) | 1 µl (20 units) |
| Nuclease-free water | To 30 µl |

Digests were incubated at 37° C. for 1 h and electrophoresed on a 1% agarose gel. Insert bands (~770 bp) and linearized pCHV101 vector (~4830 bp) were gel extracted using the Zymoclean Gel DNA recovery Kit (Zymo Research, cat. #D4002) into 20 µl of warm (pre-heated at 65° C.) 0.2× kit elution buffer (EB) diluted in PCR-grade $H_2O$.

Ligations were performed with an insert:vector ratio of 3:1 using the following:

| | |
|---|---|
| 10X T4 DNA Ligase Buffer | 2 µl |
| Insert SMD023b | 30 ng |
| pCHV101 (4.7 kb) | 60 ng |
| T4 DNA Ligase | 1 µl |
| Nuclease-free water | to 20 µl |

The ligations were incubated at room temperature for 20 minutes before transferring 5 µl of the ligation mix into 50 µl of E. Cloni competent cells. The cell/DNA mixture was incubated for 10 min on ice before adding 75 µl of 2×TYG and streaking out 125 µl of the diluted cells onto solid 2×TYAG selective agar plates. For the agar plates, the designation T refers to added tryptone, Y refers to added yeast extract, G refers to added glucose and A refers to added ampicillin antibiotic, using standard art recipes. Plates were incubated overnight at 37° C.

Colonies were picked into 3 ml of liquid 2×TYAG medium and incubated at 37° C. Clone vector DNA was prepared using the Vacuum PureYield plasmid miniprep system Quick protocol (Promega, cat. #FB093) and sequenced using the primers pCHV101_SeqFOR1 (5'-CT-GAAAGGAAGGATATAGAATGTGC-3') (SEQ ID NO:38) and PD1-2 (5'-GTCGTCTTTCCAGACGTTAG-3') (SEQ ID NO: 39).

Phage/scFv ELISA

Miniprep clones containing correct scFv sequences were electroporated into *E. coli* TG1 cells (Lucigen, cat. #60502-1) and plated onto selective 2×TYAG plates and incubated for 18-20 h at 30° C.

Ampicillin resistant colonies were picked into a 96 well U-bottom plate (Greinerbio-one, cat. #650201) filled with 200 µl of 2×TYAG and were incubated overnight at 30° C., 750 rpm, 70% humidity. Cultures were then utilized for scFv and phage ELISAs according to the following protocols:

Expression of Soluble scFv

From the overnight plate, 4 µl of culture/well was transferred into a 96 well U-bottom plate containing 170 µl/well of TB medium supplemented with 0.1% glucose and 100 µg/ml ampicillin. The bacteria were grown for 4 h at 30° C., 750 rpm, 70% humidity. ScFv expression was induced by the addition of 20 µl of IPTG (diluted to 1 mM in TB medium) to obtain a final concentration of 100 µM. The expression of soluble scFvs was performed overnight for 16-18 h at 30° C., 750 rpm, 70% humidity.

Rescue of scFv-Phage

From the overnight plate, 3.5 µl of culture/well was transferred into a 96 well U-bottom plate containing 100 µl/well of 2×TYAG. The bacteria were grown for 4 hours at 30° C., 750 rpm, 70% humidity. To rescue phage particles, 100 µl of 2×TYAG/M13K07 helper phage (Invitrogen, cat. #18311019) (200 µl M13K07 diluted into 10 ml 2×TYAG) (Invitrogen, cat. #18311019) were added to each well and the plate left stationary at 37° C. for 1 h. Infected culture (5 µl/well) was transferred into a new 96 well U-bottom plate filled with 200 µl/well of 2×TY medium, supplemented with 50 µg/ml of kanamycin and 100 µg/ml ampicillin. The rescue of scFv-displaying phage was performed overnight for 16-18 h at 30° C., 750 rpm, 70% humidity.

ELISAs

To perform the ELISA a 96-well maxisorp Nunc-immunoplate (Thermo Scientific, cat. #2022-10) was coated with 50 µl/well of human recombinant TGF-b1 (Acrobiosystems, cat. #TG1-H4212), TGF-b2 (R&D Systems, cat. #302-B2-010) and human recombinant TGF-b3 (Shenandoah Biotechnology, cat. #100-109) at 500 ng/ml in PBS at 4° C. overnight. Wells were blocked by the direct addition of 230 µl of block solution (5% skimmed milk/0.05% Tween20 in PBS) without first washing the plate. Blocking was carried out for 45 min with gentle agitation. Concurrently, the bacterial cultures containing the expressed scFv and the rescued phage were blocked by the direct addition of 120 µl of block solution. The blocked maxisorp plate was washed 3× with PBST (PBS+0.1% Tween20) before applying 150 µl of blocked scFv or phage culture to the wells. Incubation was performed for 1 h at room temperature with gentle agitation before washing of the wells with 4×PBST.

For the scFv ELISA, 100 µl of primary mouse 9E10 anti-cmyc Ab diluted 1/1000 in PBS+1% BSA was added to wells, followed by a 1 h incubation at room temperature with gentle agitation. The plate was washed 4× with PBST before the addition of 100 µl of secondary goat anti-mouse IgG $(Fab)_2$ HRP conjugate (Sigma, cat. #A9917) diluted 1/10000 in PBS+1% BSA. The plate was incubated for 1 h at room temperature with gentle agitation. The ELISA was developed by the addition of 100 µl/well of TMB substrate (ThermoFischer Scientific, cat. #34021), stabilized with 50 µl/well of stop solution (2N sulfuric acid) and absorbance signals read at 450 nm and 620 nm.

For the phage ELISA, 100 µl of primary rabbit anti-fd bacteriophage Ab (Sigma, cat. #B7786) diluted 1/1000 in PBS+1% BSA was added to wells followed by a 1 h incubation at room temperature with gentle agitation. The plate was washed 4× with PBST before the addition of 100 µl of secondary mouse anti-rabbit IgG (Y-chain specific) HRP conjugate (Sigma, cat. #A1949) diluted 1/15000 in PBS+1% BSA. The plate was incubated for 1 h at room temperature with gentle agitation before being washed 5× with PBST followed by 2× with PBS. The ELISA was developed as for the scFv plate above.

Clone Variant Competition Screening (GLv2 VH Library)

A small DNA library of LCR1901_GLv1 VH CDR variants was designed based on an analysis of published germline and proprietary database homologies. The library VH DNA was synthesized by a commercial vendor and cloned en masse into the pCHV101 LCR1901_GLv1 vector, following the excision of the GLv1 VH chain. The resulting library, termed pCHV101 LCR1901_GLv2, comprising the GLv1 VK and mutated VH CDR repertoire was electroporated into *E. coli* TG1 cells alongside parental pCHV101 LCR1901_GLv1 graft vector. Cells were plated out onto 2×TYAG and incubated for 18-20 h at 30° C.

The following day, fresh TG1 colonies containing pCHV101-LCR1901_GLv2 library clones were picked into columns 2-11 of 96-well U-bottom plates (Greinerbio-one, cat. #650201) filled with 200 µl/well of 2×TYAG media. Similarly, TG1 colonies containing the graft parent pCHV101-LCR1901_GLv1 vector were picked into column 1 (no-competition control). Column 12 (background control) contained only 200 µl/well of 2×TYAG media. Plates were incubated overnight at 30° C., 750 rpm, 70% humidity to generate a clone master plate.

The following day, a 96-pin replicator was used to inoculate a 96-well expression plate with cells from the master plate. The expression plate contained 170 µl/well of TB supplemented with 0.1% glucose and 100 µg/ml ampicillin. Cultures were grown for 6 hours at 30° C., 750 rpm, 70% humidity before inducing scFv expression with the addition of 50 µl of IPTG (0.45 mM in TB medium) to obtain a final concentration of 100 µM. Expression of scFv was allowed to proceed overnight at 30° C., 750 rpm, 70% humidity.

Concurrently, a 96-well maxisorp plate (Thermo Scientific, cat. #2022-10) was coated overnight with 50 μl/well of human recombinant TGF-b3 (Shenandoah Biotechnology, cat. #100-109) at a concentration of 250 ng/ml in PBS at 4° C.

The following day, the scFv expression plate was centrifuged to pellet the cells and 75 μl of scFv supernatant was transferred from each well into the corresponding well of a fresh non-binding polypropylene 96 well U-bottom plate. To these samples were added 75 μl of LCR1901_GLv1 mAb (IgG1) competitor antibody at an approximate concentration of 200 ng/ml (prepared in PBS containing 0.2% Tween 20 and 2% BSA) to give a final volume of 150 μl with competitor mAb at 100 ng/ml. This plate is termed the 'competitor dilution plate'.

Following a 15 min equilibration period, 230 μl of block solution (0.05% Tween20, 5% skimmed Milk) was added directly to the wells. Blocking was allowed to proceed for 45 min with gentle agitation.

The TGF-b3 coated maxisorp ELISA plate was washed 3× with PBST (PBS+0.1% Tween20) and 100 μl/well of the scFv/GLv1 mAb mixtures were added from the competitor dilution plate. Incubation at room temperature was allowed to continue for 1 h.

The maxisorp ELISA plate was washed 5× with PBST and the ELISA developed by the addition of 100 μl/well of secondary goat anti-Human IgG-Fc-HRP conjugate antibody (Sino Biological, cat. #SSA001) diluted 1/5000 (1% BSA in PBS+0.1% Tween20). Following a 1 h incubation at room temperature with gentle agitation, 100 μl/well of TMB substrate (ThermoFischer Scientific, cat. #34021) was added. Color development was stopped by the addition of 50 μl/well of 2N sulfuric acid and absorbance read at 450 nm and 620 nm.

Clone Variant Competition Screening (VK Revertant Framework Library)

A scFv clone comprising LCR1901 1G10m VH chain paired with the LCR1901_GLv1 VK chain was used as a starting point. For each chain, the contribution of the parental LCR1901 mouse framework (Fr) regions was investigated. For each chain, three variants were synthesized with either Fr1, Fr2, or Fr3 replaced with the murine parent region. These six chains were combined randomly by sequential batch cloning into pCHV101 to generate a small population of scFv DNA clones containing either one or two murine Fr regions. Following electroporation into TG1, scFvs were expressed and competition screening performed as above on 80 clones selected at random from the 2×TYAG plate, in this case using the LCR1901 murine parent mAb as ELISA competitor, and an anti-murine Fc-HRP secondary development reagent.

Reformatting of scFv VH and VK Chains into IgG1/IgG4

VH chains housed in pCHV101_scFv vectors are amplified with the following PCR primer mixtures (working stocks are 10 μM total oligos).

```
Nco1 FOR pool*
VH_Switch_FOR1
                                    (SEQ ID NO: 40)
GAGGGTGGTTCTGGCGAGTCCAATGCSGCSGCA
(10%) 1 μM

VH_Switch_FOR2
                                    (SEQ ID NO: 41)
GAGGGTGGTTCTGGCGAGTCCAATGCCRYGGCA
(10%) 1 μM

VH_Switch_FOR3
                                    (SEQ ID NO: 42)
GAGGGTGGTTCTGGCGAGTCCAATGCCATGGCA
(80%) 8 μM
```

-continued

```
Sal1 REV pool
HJSal_REV1
                                    (SEQ ID NO: 43)
ATGGACCCTTGGTCGACGCTGAGGAGACGGTGACCAGGGTTC
2.5 μM

HJSal_REV2
                                    (SEQ ID NO: 44)
ATGGACCCTTGGTCGACGCTGAGGAGACGGTGACCGTGGTCCC
2.5 μM

HJSal_REV3
                                    (SEQ ID NO: 45)
ATGGACCCTTGGTCGACGCTGAGGAGACRGTGACCAGGGTSCC
2.5 μM

HJSal_REV4
                                    (SEQ ID NO: 46)
ATGGACCCTTGGTCGACGCTGAAGAGACGGTGACCATTGTCCC
2.5 μM
```

VK chains housed in pCHV101_scFv vectors are amplified with the following PCR primer mixtures (working stocks are 10 μM total oligos).

```
BssH11 FOR pool*
VH_Switch_FOR1
                                    (SEQ ID NO: 47)
CTGGCTCTTGGCGCGGCTAGCCCTGCSATSGCT
(10%) 1 μM

VH_Switch_FOR2
                                    (SEQ ID NO: 48)
CTGGCTCTTGGCGCGGCTAGCCCTGCGMKCGCT
(10%) 1 μM

VH_Switch_FOR3
                                    (SEQ ID NO: 49)
CTGGCTCTTGGCGCGGCTAGCCCTGTGCGCGCT
(80%) 8 μM

Not1 REV pool (kappa)
KJNot_REV1
                                    (SEQ ID NO: 50)
ACCACCAGATGCTGCGGCCGCAGTTCGTTTGATYTCCACCTTGG
2.5 μM

KJNot_REV2
                                    (SEQ ID NO: 51)
ACCACCAGATGCTGCGGCCGCAGTTCGTTTGATCTCCAGCTTGG
2.5 μM

KJNot_REV3
                                    (SEQ ID NO: 52)
ACCACCAGATGCTGCGGCCGCAGTTCGTTTGATATCCACTTTGG
2.5 μM

KJNot_REV4
                                    (SEQ ID NO: 53)
ACCACCAGATGCTGCGGCCGCAGTTCGTTTAATCTCCAGTCGTG
2.5 μM
```

The PCR reactions were set up as follows:

VH—Per Reaction (50 μl)

- 1 μl scFv miniprep (20-30 ng/μL)
- 2 μl VH_Switch_FOR pool (10 μM total oligos)
- 2 μl HJSal_REV pool (10 μM total oligos)
- 2 μl PCR-grade H2O
- 25 μl 2× LongAmp taq master mix (NEB; #M0287)

VK PCR—Per Reaction (50 ul)

- 1 μl pCHV101 scFv miniprep (20-30 ng/μl)
- 2 μl VLK_Switch_FOR pool (10 μM total oligos)
- 2 μl KJNot_REV pool (10 μM total oligos)
- 20 μl PCR-grade $H_2O$
- 25 μl 2× LongAmp taq master mix (NEB; #M0287)

PCR conditions: [94° C.-30 s] initial denaturation followed by 25 cycles of [94° C.-30 s], [60° C.-30 s], [65° C.-1 min]; and a final extension step of [65° C.-5 min]. PCR products were purified by DNA clean & concentrator-5TM (Zymo Research; #D4003) into 12 μl of warm (pre-heated at 65° C.) 0.2× kit elution buffer (EB) diluted in PCR-grade $H_2O$.

The purified PCRs were digest as follow:

| | |
|---|---|
| Purified VH chain PCR | 10 μl |
| 10X CutSmart Buffer | 4 μl (1X) |
| NcoI-HF (NEB, cat. #R3193S) | 2 μl (40 units) |
| SalI-HF (NEB, cat. #R3138S) | 2 μl (40 units) |
| Nuclease-free water | To 40 μl |
| Purified VK chain PCR | 10 μl |
| 10X CutSmart Buffer | 4 μl (1X) |
| BssHII-HF (NEB, cat. #R0199S) | 2 μl (40 units) |
| NotI-HF (NEB, cat. #R3189S) | 2 μl (40 units) |
| Nuclease-free water | To 40 μl |

The IgG expression vectors were digested as follow:

| | |
|---|---|
| pSTEVe5 IgG1 VH expression vector | 10 μl |
| 10X CutSmart Buffer | 4 μl (1X) |
| NcoI-HF (NEB, cat. #R3193S) | 2 μl (40 units) |
| SalI-HF (NEB, cat. #R3138S) | 2 μl (40 units) |
| Nuclease-free water | To 40 μl |
| pSTEVe52 IgG4 VH expression vector | 10 μl |
| 10X CutSmart Buffer | 4 μl (1X) |
| NcoI-HF (NEB, cat. #R3193S) | 2 μl (40 units) |
| SalI-HF (NEB, cat. #R3138S) | 2 μl (40 units) |
| Nuclease-free water | To 40 μl |
| pSTEVe6 VK expression vector | 3 μg |
| 10X CutSmart Buffer | 4 μl (1X) |
| BssHII-HF (NEB, cat. #R0199S) | 2 μl (40 units) |
| NotI-HF (NEB, cat. #R3189S) | 2 μl (40 units) |
| Nuclease-free water | To 40 μl |

The digestions were performed at 37° C. for 1-2 h. The digested PCR products were purified by DNA clean & concentrator-5TM kit (Zymo Research; #D4003) into 20 μl of warm (pre-heated at 65° C.) 0.2× kit elution buffer (EB) diluted in PCR-grade $H_2O$. The digested vectors were electrophoretically resolved on a 0.9% agarose gel and the corresponding linearized vector bands gel extracted using the Zymoclean Gel DNA recovery Kit (Zymo Research, cat. #D4002) into 30 μl of diluted EB.

Ligations were performed at a molar ratio of 3:1 insert: vector,

| | |
|---|---|
| 10X T4 DNA Ligase Buffer | 2 μl |
| VH/VK Insert | 18 ng |
| Expression vectors | 80 ng |
| T4 DNA Ligase | 2 μl |
| Nuclease-free water | To 20 μl |

Ligations were carried out for 2 hr at RT and at 16° C. overnight. Ligation mixtures (2 μl) were combined with 50 μl of E. Cloni competent cells (prepared in house) and incubated on ice for 10 min. After diluting in 75 μl of 2×TYG, transformed cells were streaked out onto selective 2×TYAG plates and incubated overnight at 37° C. Typically, 4 colonies were picked for each construct into 3 ml of 2×TYAG medium and grown at 37° C. overnight. Plasmid minipreps were prepared using the vacuum PureYield plasmid miniprep system quick protocol (PROMEGA, cat. #FB093) and inserts confirmed by sequencing using the primers PD1-5 (5'-GAGGATTTGATATTCACCTGG-3') (SEQ ID NO:54) for the VH chains and PD1-91 (5'-GAATTCGATCAGGACTGAACAGAG-3')(SEQ ID NO:55) for the VK chains. Vector midipreps for HEK cell transfection were prepared for correct expression vector clone chains using 50 ml overnight cultures grown in 2×TYAG at 37° C. and the ZymoPURE™ Plasmid Midiprep Kit (PROMEGA, cat. #D4201).

Antibody Expression—General

Protein expression was done by transient transfection using the HEK293-6E/pTT transient expression system (National Research Council of Canada; obtained under licence). Cells were grown in non-baffled shake Erlenmeyer culture flasks (TriForest, cat #FPC0125S-K) at 120 rpm, 37° C. and 5% CO2. Cells used for transfection were grown to a cell density of $1\times10^6$ cells/ml using F17 medium containing 4 mM GlutaMAX, 0.1% Pluronic® F-68 and 25 μg/ml G418.

The transfection procedure was as follows: 45 ml of HEK293-6E cells at a density of ~$1.0\times10^6$ cells/ml (viability >97%) were transferred to a 250 ml flask. For each required expression culture, 25 μg of expression vector midiprep DNA (12.5 μg for each VK and VH chain pairings) was added to a 15 ml Falcon tube. A volume of transfection medium (F17 medium alone) was added to the tube to give 5 ml final volume and the solution gently mixed by pipetting. To a separate empty 15 ml Falcon tube was added 37.5 μl of pure [neat] FectoPRO™ (Polyplus-Transfection® SA, cat #116-010). The 5 ml of diluted DNA was carefully added to the FectoPRO™ reagent and the solution was mixed by pipetting. After incubating for 20 min at room temperature, the DNA-FectoPRO™ mixture was added to the 250 ml flask containing the cells with gentle swirling to mix. The flask was immediately transferred to a 37° C. humidified shaking incubator (120 rpm) containing 5% $CO_2$. Expression supernatants were harvested after 5 day by centrifuging cells for 3 min at 2500 g and transferring the clarified media to fresh 50 ml Falcon tubes.

IgG Antibody Purification

IgG1 and IgG4 antibodies were purified on an AKTA Pure protein purification system 25 L (GE Healthcare) using a 5 ml HiTrap Mab Select Protein A column (GE Healthcare, cat. #11003494). The column was equilibrated with PBS. After sample loading at a flow rate of 5 ml/min, columns were washed with PBS to remove unbound protein. Antibodies were eluted at a flow rate of 3 ml/min with 0.1 M citrate pH 3.2 and neutralized with Tris before overnight dialysis against PBS (15 ml Slide-A-Lyzer G2 Dialysis Cassettes, 10K MWCO; Thermo Fisher Scientific, cat. #87731). The proteins were then concentrated by centrifugation (Vivaspin 20, 50 KDa MWCO; GE Healthcare, cat. #28932362).

Antibody Expression—2 ml Scale [Yield Analysis]

IgG4 antibody yield analysis was determined using 2 ml transfection cultures as follows: ~$1.0\times10^6$ cells (viability >97%) were transferred to each well of a 12-well plate and F17 complete medium was added to give a final volume of 1 ml. For each expression culture, 0.5 μg of expression vector midiprep DNA (0.25 μg each chain) was transferred to a 1.5 ml Eppendorf tube, followed by 100 μl of F17 medium. The solution was mixed well by pipetting and the solution transferred immediately to a separate Eppendorf tube containing 0.75 μl of pure [neat] FectoPro reagent. The transfection cocktail was incubated at room temperature for 20 minutes before being added carefully to the well containing the cells. The sample was gently swirled to mix and the plate transferred immediately to a 37° C. humidified shaking incubator (120 rpm) containing 5% $CO_2$. The expression media was harvested after 5 days. Each antibody was transfected separately in triplicate to assess comparative crude expression yield in the system.

Fab Antibody Purification

His-tagged Fab antibodies were purified on an AKTA pure protein purification system 25 L (GE Healthcare) using a 5 ml HisTrap Excel column (GE Healthcare, cat. #17-3712-05). The column was equilibrated with IMAC wash buffer pH 7.5 (50 mM Tris, 0.5 mM NaCl, 10 mM Imidazole). After sample loading at a flow rate of 1 ml/min, columns were washed first with IMAC wash buffer and then with IMAC elution buffer pH 7.5 (50 mM Tris, 0.5 mM NaCl, 300 mM Imidazole). Proteins were eluted at a flow rate of 1 ml/min and then dialyzed overnight against PBS (15 ml Slide-A-Lyzer G2 Dialysis Cassettes, 10K MWCO; Thermo Fisher Scientific, cat. #87731). The proteins were then concentrated by centrifugation (Vivaspin 20, 10 KDa MWCO; GE Healthcare, cat. #28932360).

Size Exclusion Chromatography and SDS-PAGE Gel Analysis

The monodispersity/aggregation state of the antibodies was checked by qualitative size-exclusion chromatography (SEC) using a Superdex 200 Increase 5/150GL column (GE Healthcare, cat. #28-9909-45). The column was equilibrated in PBS before loading 100 μl of sample at a flow rate of 0.3 ml/min.

The size and the quality of the antibodies was checked by reducing and non-reducing SDS-PAGE using the NuPAGE® Novex® 4-12% Bis-Tris Protein Gels (Thermo-Fisher LifeTechnologies, cat. #NP0321BOX). MOPS-buffer was used as the running buffer (Thermo-Fisher Life Technologies cat. #). 5 μg of each antibody was mixed with 5 μl of LDS-sample buffer (Thermo-Fisher Life Technologies cat. #)+/−2 μl of sample reducing buffer. The samples were heated at 70° C. for 10 minutes prior to loading. Gels were developed by staining with InstantBlue (Expedeon, cat. #ISB1L).

Thermal Shift Assay

The thermal stability of the anti TGF-beta 3 antibodies was evaluated using the protein thermal shift assay using the 7500 Fast Real Time PCR instrument (Applied Biosystem). The assay involves mixing the antibody with the protein thermal shift TM dye and applying a controlled heating ramp. As the protein begins to denature, the dye interacts with exposed hydrophobic regions and fluoresces more strongly, establishing one or more transition temperatures.

Samples were prepared as follows:

| Component | Volume |
|---|---|
| Protein Thermal Shift ™ Buffer | 5.0 μl |
| Protein diluted in PBS | 12.5 μl |
| Diluted Protein Thermal Shift ™ Dye (8X) | 2.5 μl |
| Total volume for each control reaction | 20.0 μl |

Experimental setup on the 7500 Fast RT-PCR machine:

| SETUP | SETTING |
|---|---|
| Experiment properties | Experiment type: Melt Curve<br>Reagents: Other<br>Ramp speed: Fast or Standard |
| Target properties | Reporter: ROX<br>Quencher: None |
| Plate Layout | Assign targets to all wells in use<br>Passive reference: None |
| Run Method | Reaction volume per well: 20 μl<br>Thermal profile:<br>Step1, Temp: 25° C., Time: 2 minutes<br>Step2, Temp: 99° C., Time: 2 minutes<br>Ramp mode: Continuous<br>Ramp Rate:<br>ViiA ™ 7 System: Step 1: 1.6° C./s,<br>Step 2: 0.5° C./s<br>StepOne ™ and StepOnePlus ™ Systems<br>and 7500 and 7500 Fast Systems: 1% |

The Tm was calculated via the 7500 instrument software using the first derivative versus the temperature plot.

TMLEC Functional Neutralization

The assay is based on TMLEC cells (Transfected Mink Lung Epithelial cell) containing a Luciferase reporter gene as described in Abe M et al Analytical Biochemistry 1994, 216:276-284. The cell line was subcloned multiple times in the lab and subclone 20 was used in these assays. Cells are cultured under 8% CO2 in DMEM supplemented with 10% FCS, and AAG (0.55 mM L-arginine, 0.24 mM L-asparagine, 1.5 mM L-glutamine and 400 ug/ml G418).

TGFbs±antibody dilutions are incubated at 37° in 96 well plates for 4 hours. 100 ul of this «mixture» was then transferred into 96 well flat bottomed opaque ELISA plates suitable for Luciferase activity counting, containing 5×10×4 TMLEC cells/well in 100 ul of the above culture medium) and cultured in the well for at least 1 h.

All TGFß isoforms were used at 500 pg/ml final concentration. Antibody dilutions usually started at 30 ug/ml. Plates are incubated for 20-24 h. Then 100 ul of the well content was carefully removed and replaced by 100 ul Luciferase substrate diluted in the lysis buffer of the Perkin-Elmer Ultra-brite Luciferase kit. Luciferase activity was quantitated immediately in a bioluminescence ELISA reader.

Competitive Binding of IgG4 mAbs (Versus Biotinylated Murine LCR1910 Parent)

Nunc Maxisorb ELISA plates were coated overnight at 8° C. with 0.5 μg/ml hTGF-ß1 (Peter Sun, NIH) or hTGF-ß3 (Shenandoah Biotech) at 0.5 μg/ml in 40 mM glycine buffer pH 9. Plates were washed and blocked with 10% FCS for 1 h at 37° C. In a separate low binding Greiner Bio-One ELISA plate, various concentrations of competing Abs were mixed with a constant concentration of biotinylated parental 13A1 or 1901 at 200 ng/ml in PBS+BSA (10 mg/ml) and then transferred onto the TGF-ß-coated Nunc Maxisorb ELISA plate. After incubation for 2 h at 37° C. plates were washed, Avidine-HRP added and incubated for 1 h at 37° C. Plates washed again, TMB substrate was added and bound biotinylated antibody was quantitated by measuring color development in an ELISA reader at a wave length of 450 nm.

Example 3

Reformatting of Murine 1901 Antibody into scFv and Grafting

Reformatting of Murine Antibody 1901 VH and VL into scFv (LCR1901_scFv), Expression in *E. coli* and Verification of Binding Specificity Mouse antibody 1901 VH and VL domain nucleotide sequences (SEQ ID NOs: 9 and 11 respectively) as described in FIG. 1 were synthesized for expression as scFv in *E. coli*.

ScFv were formatted in the orientation VK-linker-VH. Minor point mutations (VK: 52-54 AGG>CGA and 181-183 CGC>CGG; VH: 118-120 AGG>CGT and 292-297 AGAAGG>CGTCGC) were incorporated at this stage in order to exchange rare Arg codons in the reading frames to potentially improve expression in *E. coli*. The scFv was subsequently cloned into pCHV101, a proprietary phagemid vector allowing the dual expression and secretion of the molecules from *E. coli* as either free scFv (LCR1901_scFv) or as fusions to the pIII coat protein of filamentous bacteriophage (LCR1901_Phage). Both expression modalities preserved strong and specific binding to surface-immobilized recombinant human TGFb3 in ELISA (FIG. 2).

Selection of Human VH for Grafting

IGHV1-69*08 was selected from the IMGT reference directory (imgt.org) and an internal IgM/D sequence database as the closest global human homologous germline VH sequence.

Selection of Human VL for Grafting

IGKV1-39*01 was selected from the IMGT reference directory (imgt.org) and an internal IgM/D sequence database as the closest global human homologous germline VK sequence.

Figure 4:
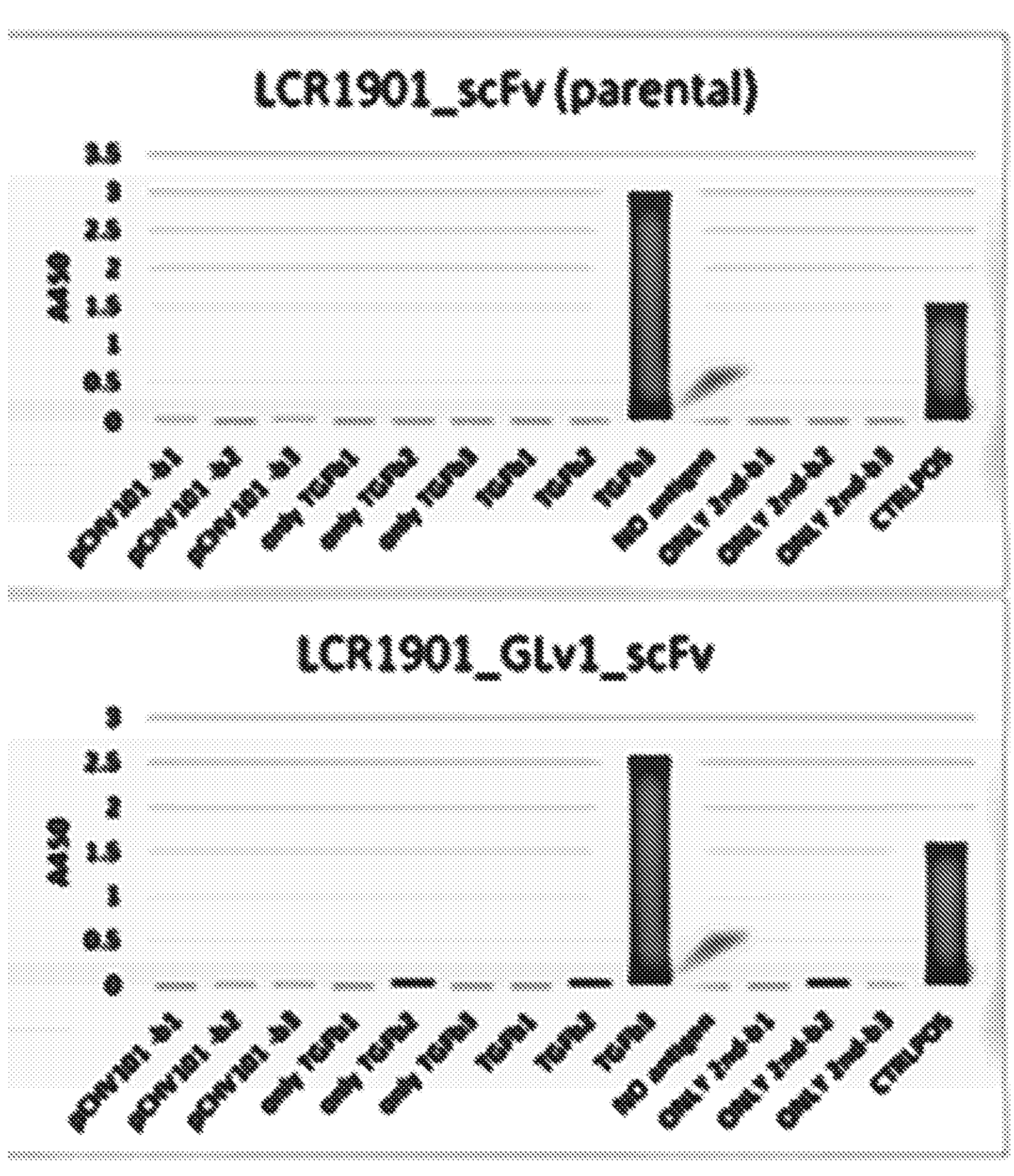
FIG. 4 graphs ELISA results of the parental soluble scFv LCR1901_ScFv and LCR1901_Glv1_scFv and demonstrates that grafting of murine CDRs into human framework preserves binding and fine specificity recognition for TGFb3.

Grafting of Murine CDRs onto Human VH and VL Frameworks, Expression as scFv and Verification of Binding Specificity The six murine CDRs (light chain CDRs: CDR1 KASQSVINAVA (SEQ ID NO:4), CDR2 YASRNYT (SEQ ID NO:5) and CDR3 QQDYSSPYT (SEQ ID NO:6); and heavy chain CDRs: CDR1 SSSWIH (SEQ ID NO:26), CDR2 RIYPGDGDTNYTGKFK (SEQ ID NO:27) and CDR3 RMITTQAAMD (SEQ ID NO:3) were grafted onto the respective human VH and VK framework and Vernier regions, and initially expressed as scFv. ScFv were formatted in the orientation VK-linker-VH. ScFv nucleotide sequences were synthesized by GeneArt (Thermo Fischer Scientific) and were cloned into the pCHV101 phagemid prior to scFv expression in *E. coli* (1901_GLv1_scFv). FIG. 3 shows the amino acid sequence alignment of the murine and grafted 1901_scFv constructs (SEQ ID NOs: 13 and 14 respectively). The six CDRs are denoted in bold. Grafting of the murine CDR regions into the selected human VK and VH framework regions preserves binding specificity for TGFb3 (FIG. 4).

Figure 5:
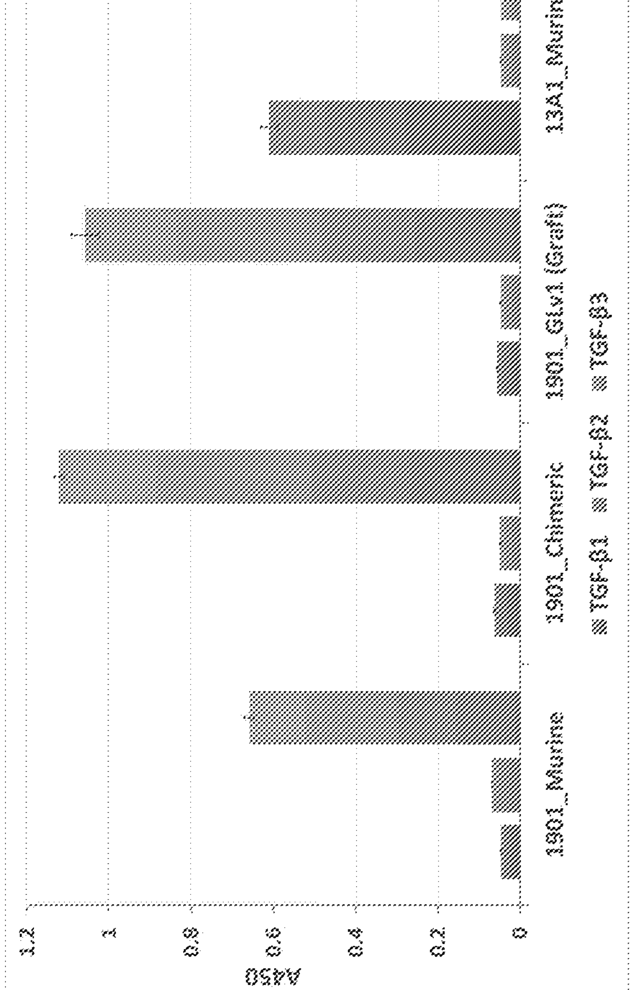
FIG. 5 depicts ELISA results against TGFb1, TGFb2 and TGFb3 of the indicated constructs 1901_Murine, 1901_Chimeric, 1901_Glv1 (graft) and 13A1-Murine (13A1 is a murine anti-TGFb1 antibody). Reformatting of grafted variable domains into a full huIgG1 scaffold preserves TGFb3 binding and fine specificity recognition for TGFb3.

Reformatting from scFv into Human IgG1, Expression in HEK293 Cells and Verification of Binding Specificity Human VK and VH chains were reformatted by fusion to their respective heavy and light human constant domains housed in discrete pTT5-based mammalian expression vectors. The resulting IgG1 heterodimers were expressed to the media via transient co-transfection using small-scale HEK293-6E suspension cell culture. Supernatants containing the grafted antibodies together with the murine chimeras (mouse variable domains fused to human IgG1 Fc) antibody were subjected to TGFβ specificity ELISA alongside the original purified parental murine antibody 1901. Binding specificity for TGFb3 was preserved for both chimeric and grafted human IgG1 1901 antibodies (FIG. 5).

Example 4

Sequence Analysis and Mutations Introduced

Identification and Correction of Potential CDR Sequence Liabilities in LCR1901_GLv1 by Mutagenesis The LCR1901_GLv1 CDR sequences of both the VH and VK chains were subjected to a BLAST homology analysis against both the IMGT variable domain reference collection (imgt.org) and a proprietary database comprising 6 million translated IgM/IgD VH reads obtained from the peripheral blood of healthy donors. A series of residues were identified that may comprise potential physicochemical development risks or are mismatched/rare when considered alongside human residues at the same position (human consensus residues) in an alignment of the top scoring CDR/J homologies (FIG. 6). A small permutation library for the suggested CDR VH variants was constructed and scFv constructs were tested in an ELISA for competitive binding to LCR1901_GLv1. In addition, a small permutated VK mutant library was generated and combined with hits of the above VH mutant library. FIG. 6 summarizes the suggested CDR and junctional residues with potential sequence liabilities, their suggested human consensus residue correction and validation of final selected residue based on a competitive binding assay. The resulting VH is termed LCR1901_VH_1G10 (SEQ ID NO:17) (FIG. 7). The CDRs in LCR1901_VH_1G10 include alterations from the original 1901 antibody and correspond to the following VH CDRs: CDR1 GYTFSSSWIH (SEQ ID NO:28), CDR2 WIGRIYPGDGDTDYSEKFQ SEQ ID NO:29) and CDR3 ARRMITTQAAL (SEQ ID NO:30) (amino acid residues in the CDRs altered from the parent 1901 antibody are underlined).

Additional Mutation in LCR1901_VH_1G10

Residue S123 in the joining region in FR4 was mutated to L123 to correct for hu IGHJ4. The resulting VH is termed LCR1901_VH_1G10m (SEQ ID NO: 17) (FIG. 7). FR2 in the VH chain of LCR1901 was identified as critical for maintaining neutralization potency of the antibody. Subsequently, three residues in FR2 were back-mutated to the original murine residues (R43>K43; A45>R45; and Q48>K48) and the resulting VH is termed LCR1901_VH_1G10m_GLv1_03 (K) (SEQ ID NO:19) (FIG. 7). In an alternative VH sequence, only one residue in the FR2 region was back-mutated to the original murine residues (Q48>K48) and the resulting Vh is termed LCR1901_VH-1G10m_02(J) (SEQ ID NO: 36). LCR1901_VH_1G10m and LCR1901_VH_1G10m_GLv1_03 (K) (and also the LCR1901_VH-1G10m_02(J)) heavy chains retain the altered and variant CDRs of LCR1901_VH_1G10, SEQ ID NOs:28-30 noted above.

Additional Mutations in LCR1901_VK_GLv1 FR Regions

Residue L124 in the joining region in FR4 was mutated to V124 to correct for hu IGKJ4. The resulting VK is termed LCR1901_VK_GLv1 (SEQ ID NO:21) (FIG. 8). FR3 and to a lesser degree FR2 in the VK chain of LCR1901 were identified as critical for maintaining neutralization potency of the antibody. FR reverse point mutation combined with VH-VK chain pairing experiments identified two VK chains with higher TGFb3 neutralization potency than LCR1901_VK_GLv1 (FIG. 8) which are described as follows:

LCR1901_VK_GLv1_03 (F) (SEQ ID NO:22) (FIG. 8) has two back-mutations to the original murine residues in FR2 (K48>Q48 and A49>S49) and five back-mutations to the original murine residues in FR3 (574>D74; 583>Y83; L89>F89; P96>A96 and T101>V101). In addition, in FR3 F99 was adjusted to V99 for a better human "local" match (IGKV4-1*01) than the "global" IGKV1-39*01 initial graft.

LCR1901_VK_GLv1_05 (H) (SEQ ID NO:23) (FIG. 8) has five back-mutations to the original murine residues in FR3 (574>D74; 583>Y83; L89>F89; P96>A96 and T101>V101). In addition, in FR3 F99 was adjusted to V99 for a better human local match (IGKV4-1*01) than the "global" IGKV1-39*01 initial graft.

LCR1901_VK_GLv1, LCR1901_VK_GLv1_03 (F) and LCR1901_VK_GLv1_05 (H) retain the 1901 VL CDRs CDR1 KASQSVINAVAWY (SEQ ID NO:31), CDR2 LLIYYASNRYT (SEQ ID NO:32) and CDR3 QQDYSSPY (SEQ ID NO:33) denoted in bold in FIG. 8.

Human Germline Homology of LCR1901 VH+VK Variants

Global alignment analysis of LCR1901_VH and VK was performed using the IMGT database (imgt.org) and the corresponding human germline homologies were determined for each chain. Germline homologies for each chain was over 80% (range 81-87%) (FIG. 9).

Example 5

Expression of Antibody Variants in Human IgG4 Format

The LCR1901 antibody variants were reformated into human IgG4 (S228P) antibodies and expressed in human IgG4 format. For this purpose human IGHG4*01 was selected as the human Ig constant heavy chain, which was further modified to accommodate an S228P mutation which is recognized and has been shown in the art to stabilize the antibody of potential Fab-arm exchanges (Silva et al, J Biol Chem. 2015 Feb. 27; 290(9):5462-9). Human CK*01 was selected as the human Ig constant light chain. IgG4 heterodimers were expressed to the media via transient co-transfection of heavy and light chain vectors using small scale HEK293-6E suspension cell culture and then purified by Protein A affinity chromatography.

The protein sequences of four LCR1901 IgG4 variants are shown in FIGS. 10-13 as follows:

LCR1901_VH_1G10m-LCR1901_VK_GLv1_03(F) also denoted 1901-1C is provided in FIG. 10. The 1901-1C antibody comprises the heavy chain sequence of LCR1901_VH_1G10m (SEQ ID NO:18), and light chain sequence LCR1901_VK_GLv1_03(F) (SEQ ID NO:22).

LCR1901_VH_1G10m-LCR1901_VK_GLv1_05(H) also denoted as 1901-1A is provided in FIG. 11. The 1901-1A antibody comprises the heavy chain sequence of LCR1901_VH_1G10m (SEQ ID NO:18), and light chain sequence LCR1901_VK_GLv1_05(H) (SEQ ID NO:23).

LCR1901_VH_1G10m_03(K)-LCR1901_VK_GLv1_03 (F) also denoted 1901-1D is provided in FIG. 12. The 1901-1D antibody comprises the heavy chain sequence of LCR1901_VH_1G10m_03(K) (SEQ ID NO:19), and light chain sequence LCR1901_VK_GLv1_03(F) (SEQ ID NO:22).

and LCR1901_VH_1G10m_03(K)-LCR1901_VK_GLv1_05(H) also denoted as 1901-1B is provided in FIG. 13. The 1901-1B antibody comprises the heavy chain sequence of LCR1901_VH_1G10m_03(K) (SEQ ID NO:19), and light chain sequence LCR1901_VK_GLv1_05 (H) (SEQ ID NO:23).

Example 6

Predicted Packing Angles of Variants

The packing torsion angles for the respective antibodies were predicted for each of the LCR1901_VH and VK variants in silico using PAPS (bioinf.org.uk/abs/paps). The predicted values for the initial CDR graft (1901 VH GLv1/1901_VK_GLv1) and the subsequent highly active mutated variants were very similar and differed markedly from the original 1901 murine antibody (FIG. 14).

Example 7

Potency of Antibodies to Neutralize TGFB Signaling

The potency of LCR1901 IgG4 antibodies to neutralize TGFb signaling was determined using TMLEC reporter cells by assessing neutralization of TGFb isoform specific signaling in a TMLEC reporter cell assay. The four IgG4 variants LCR1901_VH_1G10m-LCR1901_VK_GLv1_03 (F) (1901-1C), LCR1901_VH_1G10m-LCR1901_VK_GLv1_05(H) (1901-1A), LCR1901_VH_1G10m_03(K)-LCR1901_VK_GLv1_03(F) (1901-1D) and LCR1901_VH_1G10m_03(K)-LCR1901_VK_GLv1_05 (H) (1901-1B) were highly potent in neutralizing TGFb3 induced luciferase reporter gene product expression in a dose-dependent manner. All four LCR1901 variants were more potent in neutralizing TGFb3 signaling in TMLEC cells than the parental murine antibody 1901 (FIG. 15 and FIG. 16).

In addition, LCR1901 variant antibody having VH sequence LCR1901_VH_1G10m_02(J) (SEQ ID NO:36) and VL sequence LCR1901_VK_GLv1_03(F) (SEQ ID NO:22) was generated and tested for TGFb3 signaling in TMLEC cells and found to be effective in neutralizing (data not shown).

Example 8

TGFB Isoform Specificity

TGFb isoform specificity of LCR1901 IgG4 variants was assessed in a TMLEC reporter assay. The four IgG4 variants LCR1901_VH_1G10m-LCR1901_VK_GLv1_03(F) (1901-1C), LCR1901_VH_1G10m-LCR1901_VK_GLv1_05(H) (1901-1A), LCR1901_VH_1G10m_03(K)-LCR1901_VK_GLv1_03(F) (1901-1D) and LCR1901_VH_1G10m_03(K)-LCR1901_VK_GLv1_05 (H) (1901-1B) were tested and showed highly selective neutralization of TGFb3 isoform induced signaling but no neutralization of TGFb1 and TGFb2 isoform induced expression of the luciferase reporter gene product (FIG. 17).

Example 9

Competitive Binding and Binding Kinetics

The potency of the humanized LCR1901 IgG4 antibody variants to compete with the parental murine antibody for binding to TGFb3 was assessed by ELISA. The four IgG4 variants LCR1901_VH_1G10m-LCR1901_VK_GLv1_03 (F) (1901-1C), LCR1901_VH_1G10m-LCR1901_VK_GLv1_05(H) (1901-1A), LCR1901_VH_1G10m_03(K)-LCR1901_VK_GLv1_03(F) (1901-1D) and LCR1901_VH_1G10m_03(K)-LCR1901_VK_GLv1_05 (H) (1901-1B) competed with the parental murine 1901 antibody for binding to TGFb3 in a dose-dependent manner (FIG. 18).

Characterization of Binding Kinetics of LCR1901 Monovalent Fab Antibodies

The four IgG4 variants LCR1901_VH_1G10m-LCR1901_VK_GLv1_03(F) (1901-1C), LCR1901_VH_1G10m-LCR1901_VK_GLv1_05(H) (1901-1A), LCR1901_VH_1G10m_03(K)-LCR1901_VK_GLv1_03

(F) (1901-1D) and LCR1901_VH_1G10m_03(K)-LCR1901_VK_GLv1_05(H) (1901-1B) were expressed as stable Fab and binding kinetics to TGFb were assessed using plasmon surface resonance (Biacore). Fab binding ELISA data are summarized in FIG. 19 and representative Biacore binding profiles are shown in FIG. 20. Binding affinities of the Fabs were in the pM range.

Example 10

Additional Characterization of Humanized Antibodies

SEC profiling: Molecular integrity (unformulated) of the four IgG4 variants LCR1901_VH_1G10m-LCR1901_VK_GLv1_03(F) (1901-1C), LCR1901_VH_1G10m-LCR1901_VK_GLv1_05(H) (1901-1A), LCR1901_VH_1G10m_03(K)-LCR1901_VK_GLv1_03 (F) (1901-1D) and LCR1901_VH_1G10m_03(K)-LCR1901_VK_GLv1_05(H) (1901-1B) was assessed using analytical size exclusion chromatography (SEC). The four LCR1901 IgG4 antibodies displayed similar elution behaviour. No indication for fragmentation or peak spreading was observed and aggregation levels were low suggesting the IgG4 antibodies are stable and molecularly homogenous. Typical SEC profiles are shown in FIG. 21.

Thermostability: Relative molecular stability of the four IgG4 variants LCR1901_VH_1G10m-LCR1901_VK_GLv1_03(F) (1901-1C), LCR1901_VH_1G10m-LCR1901_VK_GLv1_05(H) (1901-1A), LCR1901_VH_1G10m_03(K)-LCR1901_VK_GLv1_03(F) (1901-1D) and LCR1901_VH_1G10m_03(K)-LCR1901_VK_GLv1_05 (H) (1901-1B) to heat stress was assessed using differential scanning fluorimetry (DSF). The four LCR1901 IgG4 variants showed 2-transition non-cooperative domain melt curves, with an characteristic earlier unfolding of the IgG4 CH2 domain (Tm1). Unfolding of the Fab domains is represented in transition 2 (FIG. 22 and FIG. 23).

Scale-up expression yields: Suitability of the four IgG4 variants LCR1901_VH_1G10m-LCR1901_VK_GLv1_03 (F) (1901-1C), LCR1901_VH_1G10m-LCR1901_VK_GLv1_05(H) (1901-1A), LCR1901_VH_1G10m_03 (K)-LCR1901_VK_GLv1_03(F) (1901-1D) and LCR1901_VH_1G10m_03(K)-LCR1901_VK_GLv1_05 (H) (1901-1B) for potential larger scale expression was assessed using transient expression in a singular mammalian cell system (2 ml scale). The four LCR1901 IgG4 variants were found to express efficiently in a transient singular mammalian cell system. Expression yields are summarized in FIG. 24.

Example 11

The application and use of genetically engineered T cells expressing chimeric antigen receptors (CAR) against cell surface proteins in cancer therapy has provided a new and improved approach to various cancers. In certain instances, T cells modified to express chimeric antigen receptor (CAR) alone have been subject to suppression within the hostile tumor microenvironment, which can limit the efficacy of CAR T cells in some clinical indications. For example, immunosuppressive cytokines (such as IL-6, Il-10 and TGF-β) can provide a favorable environment for tumor growth and also inhibit the tumoricidal activity of endogenous T cells as well as CAR T cells. Studies have shown that inhibition of TGFβ receptor may potentiate CAR T cell activity by inhibiting the immunosuppressive effects of TGFβ on the microenvironment (Vong Q et al (2017) Blood 130:1791).

We sought to evaluate the effects and efficacy of TGFb3 specific antibody to counteract TGFb3-mediated inhibition of CAR T cell activity. CAR T cells directed against mesothelin were assessed against human lung carcinoma cells. CAR T cells directed against epidermal growth factor receptor (EGFR) were evaluated for killing human breast cancer cells.

In the lung carcinoma studies, primary human T cells were transfected with an anti-mesothelin CAR (hP4; described in US2014301993 A1). The T cells and TGFb3 were added and killing of target Meso+H-226 human lung carcinoma cells was evaluated. Addition of TGFb3 antibody 1901-1B was assessed for an effect on cell killing. CART cells alone killed the Meso+ lung target cells. In the presence of TGFb3, cell killing was significantly inhibited. The TGFb3-mediated inhibition of cell killing was abolished upon addition of the TGFb3 specific antibody. Antibody 1901-1B was highly potent even at low concentration (≤50 ng/ml). The results are depicted in FIG. 25, showing in vitro rescue of TGFb3-mediated inhibition of anti-MSLN CAR-T target cell killing by humanized mAb 1901-1B.

A similar study was conducted with CAR T cells directed against EGFR and human breast cancer cells. Primary human T cells (CD3/CD28 activated and expanded peripheral blood mononuclear cells (PBMCs)) were transfected with an anti-EGFR CAR (scFv Panitumumab). The CAR T cells and TGFb3 were added and killing of target EGFR+ MDA-MB-231 human breast cancer cells was evaluated. Addition of TGFb3 antibody 1901-1B was assessed for an effect on cell killing. CAR T cells alone killed the EGFR+ breast cancer target cells. In the presence of TGFb3, cell killing was significantly inhibited. The TGFb3-mediated inhibition of cell killing was abolished upon addition of the TGFb3 specific antibody 1901-1B. The results are depicted in FIG. 26, showing in vitro rescue of TGFb3-mediated inhibition of anti-EGFR CAR-T target cell killing by humanized mAb 1901-1B.

Thus, it has been demonstrated in two distinct cancer cell model systems that inhibition of primary CART cell killing by TGFb3, representing anticipated cell therapy inhibition by endogenous TGFb3, can be reversed by administration of TGFb3 isoform-specific mAb 1901-1B.

Methods

Target cell lines and primary effector cells: Human endogenous antigen-positive target cell lines H226 (lung carcinoma, MSLN$^+$, ATCC® CRL-5826™) and MDA-MB-231 (breast adenocarcinoma, EGFR$^+$, ATCC® HTB-26™), were maintained in RPMI-1640 Glutamax (Gibco BRL Life Technologies, Inc., Gaithersburg, MD) containing 10% fetal bovine serum (FBS) and Pen/Strep at a concentration of 100 IU/ml. Cells were maintained in a humidified atmosphere containing 5% carbon dioxide ($CO_2$) at 37° C. Buffy coats were obtained from healthy volunteers from the (Interregional Blood transfusion SRC, Switzerland) blood bank. Peripheral blood mono-nucleated cells (PBMCs) were isolated from fresh buffy coats by density centrifugation using Lymphoprep (Axonlab).

Generation of CAR-modified T cells: CAR expression cassettes were housed in a pRRL lentiviral vector backbone. The organization of elements was typical of second generation CARs with the scFv appended to hCD28 [extracellular spacer region, TM, and signaling domain] and hCD3zeta. Monomeric GFP was incorporated in direct fusion downstream of CD3zeta to allow direct assessment of transfection efficiency. The hP4 scFv utilized for the anti-MSLN CAR was generated based on patent US2014301993 A1. The anti-EGFR scFv was reverse engineered from the published Panitumumab sequence (WO2012138997).

Virus production was performed by transient co-transfection of HEK293T producer cells with pRRL-CAR and packaging plasmids (pCMVR8.74 and pMD2.G; Didier Trono lab, EPFL) using Turbofect transfection reagent (Life Technologies). Virus-containing supernatant was harvested after 48 h and concentrated by ultracentrifugation.

PBMCs were plated ($0.5\times10^6$ per well) in a non-tissue culture-treated 24-well plate that had been pre-coated with CD3 clone OKT3 (1 μg/mL; ThermoFisher) and CD28 clone CD28.2 (2 μg/mL; ThermoFisher) anti-human antibodies. Cells were cultured in complete media RPMI-1640+GlutaMAX (ThermoFisher) supplemented with 10% FBS and human recombinant human IL2 (50 IU/mL, Glaxo IMB) for 2 days. On day 3, freshly prepared lentiviral supernatants were used to transduce the CD3/CD28-activated PBMCs and they were maintained in complete media supplemented with human recombinant human IL2 (50 IU/mL, Glaxo IMB) for a further 2 days. On day 5, the expanded PBMCs were supplemented with complete media containing 10 ng/ml of IL-7 and IL-15 (Miltenyi Biotec Inc.) and incubated for 1-2 weeks at 37° C., 5% $CO_2$ until they were used for the killing assay. Subsequently, cells were split and fed every 2-3 days with fresh media plus IL-7/IL-15. Transfection efficiencies of ~40% (anti-MSLN CAR) and 50% (anti-EGFR CAR) were determined based on the proportion of $GFP^+$ cells.

Kinetic cytotoxicity assays: H226 target cells (100 μL/well) were seeded in 96-well plates at a density of $0.015\times10^6$ cells/mL in complete medium. The following day, cell density had reached $0.02\times10^6$ cells/well. Supernatant was removed and 50 μL (500 nM) of CytotoxRED dead-cell staining reagent (Incucyte, Essen Bioscience) was added to each well. Effector anti-MSLN CAR cells ($2\times10^6$ cells/mL) in complete medium were combined with 1 μL of stock TGFβ3 (MILAN Analytica AG; 500 ng/mL) to give a concentration of 2 ng/mL, or left untreated. Treated/untreated CAR cells (50 μL) were added to each well, resulting in a 5:1 E:T ratio +/−1 ng/mL TGFβ3. The anti-TGFβ3 neutralizing (reversal) potential of hIgG4 1901_1B antibody was determined by its co-inclusion at a final concentration of 500 ng/mL. Plates were returned to the incubator for 30 min to allow the combined cells and dye to settle and equilibrate, before being transferred to the Incucyte system for 3 days. Cell death was monitored as an increase in red fluorescence and analyzed with the IncuCyte® integrated analysis software (Incucyte, ZOOM2016A). Kill slopes were determined using the Total Red Image Integrated Intensity per Image data.

Anti-EGFR CAR-mediated killing was similarly determined for MDA-MB-231, however, in this case target cells were pre-stained 24 h prior to plating with 1 μM of Cytolight rapidRED cytoplasmic staining dye (Essen Bioscience). Stained cells were seeded in 96-well plates at a density of $0.015\times10^6$ cells/mL in complete medium. The following day, cell density had reached $0.02\times10^6$ cells/well. Supernatant was removed and 100 μL/well of effector anti-EGFR CAR cells ($2\times10^6$ cells/mL)+/−1 ng/mL TGFβ3 was added to achieve a 5:1 E:T ratio. The anti-TGFb3 neutralizing (reversal) potential of hIgG4 1901_1B antibody was determined by its co-inclusion at a final concentration of 500 ng/mL. Plates were returned to the incubator for 30 min to equilibrate, before being transferred to the Incucyte system for 3 days. Cell death was monitored as a decreased count of stained target cell red fluorescence and analyzed with the IncuCyte® integrated analysis software (Incucyte, ZOOM2016A). Kinetic progress curves were determined using normalized Total Red Object Area (μm2/well) data.

Example 12

Studies were conducted to demonstrate that the variant TGF-β3 antibodies can be transduced into T cells and secreted. T cells were transfected with vector encoding anti-TGF-β3 antibody with an N-terminal signal sequence for secretion. The T cells (Jurkat) expressed and secreted antibody, which was active and bound target TGF-β3.

Methods

Jurkat transfection with anti-TGF/3 scFv-Fc fusion constructs: For evaluation of potential T cell secretion, Jurkat T cells were transfected with a pRRL-based lentiviral vector (Origin: Didier Trono Lab, EPFL) containing an anti-TGFβ3 (1901_1B) scFv-Fc(hIgG4) open reading frame with an N-terminal secretory pathway signal sequence. Controls comprised either un-transfected or an irrelevant isotype control transfected scFv-Fc. One week after transfection, the cells were plated in 6-well plates at a density of $2\times10^6$ cells/ml and cultured in RPMI containing 10% FBS for 24 h at 37° C., 5% $CO_2$. Cells were then gently pelleted by centrifugation and the supernatant collected for subsequent ELISA.

Enzyme-linked immunosorbent assay (ELISA): A 96-well plate (Nunc Maxisorp, Thermo Fisher Scientific, #442404) was coated with 100 μl of TGFβ3 (Milan Analytica, #002003) at a concentration of 0.5 μg/ml in PBS over-night at 4° C. Next day, the plates were directly blocked with 230 μl of 5% skimmed milk/PBST (0.1% Tween in PBS) for 1 h under gentle agitation. Following blocking, plates were washed 3× with PBST and 100 μl of Jurkat supernatant (diluted with 1% BSA in PBST) was added to allow binding of any secreted anti-TGFβ3 scFv-Fc to the plate bound TGFβ3 antigen. Incubation was at RT for 1 h with gentle agitation. Wells were washed 3× with PBST and 100 μl of MP-conjugated secondary antibody Goat anti-Human IgG-Fc-HRP (Sino Biological, #SSA001-200) was added at a concentration 0.2 μg/ml, under gentle agitation for 1 h. Then, plates were washed 5× with PBST and 2× with PBS. Following the washing steps, the colorimetric read-out was developed with TMB substrate reagent (Biolegend, #34029) and stabilized with 2N sulfuric acid. Absorbance was measured at 45C) nm and 620 nm on a BioTek Synergy plate reader.

The results of Jurkat-secreted anti-TGFβ3 antibody (1901_1B) versus immuobilized TGFβ3 are depicted in FIG. 27. No binding was observed with isotype control antibody. Serial dilutions of the secreted 1901-1B antibody bound the TGF-β3 and at levels comparable to added exogenous 1901-1B antibody. These results demonstrate that the variant TGFβ3 antibodies can be expressed in and secreted by lymphoid cells, including T cells, and secreted antibody is effective to bind TGFβ3. Lymphoid cells engineered to express the TGFβ3 antibodies of the invention are useful in numerous applications, including in cancer therapy and immune modulation.

This invention may be embodied in other forms or carried out in other ways without departing from the spirit or essential characteristics thereof. The present disclosure is therefore to be considered as in all aspects illustrated and not restrictive, the scope of the invention being indicated by the appended Claims, and all changes which come within the meaning and range of equivalency are intended to be embraced therein.

Various references are cited throughout this Specification, each of which is incorporated herein by reference in its entirety.

What is claimed is:

1. An isolated antibody or antigen-binding fragment thereof which recognizes human and mouse transforming growth factor beta 3 (TGF-β3), which neutralizes activity of TGF-β3, and which does not recognize or bind human or mouse TGF-β1 or TGF-β2, wherein the antibody or fragment comprises a heavy chain variable region sequence comprising a CDR1 sequence SSWIH (SEQ ID NO:1), a CDR2 sequence RIYPGDGDTDYSEKFQ (SEQ ID NO:34), and a CDR3 sequence RMITTQAALDY (SEQ ID NO: 35) and a light chain variable region sequence comprising a CDR1 sequence KASQSVINAVA (SEQ ID NO:4), a CDR2 sequence YASNRYT (SEQ ID NO: 5), and a CDR3 sequence QQDYSSPY (SEQ ID NO:33);

and wherein the antibody or fragment comprises the heavy chain variable region sequence:

(a) LCR1901_VH_1G10m (SEQ ID NO:18) or variants thereof having at least 90% amino acid identity to the sequence LCR1901_VH_1G10m (SEQ ID NO:18), wherein said variants retain TGF-β3 reactivity and neutralization;

(b) LCR1901_VH_1G10m_03 (K) (SEQ ID NO:19) or variants thereof having at least 90% amino acid identity to the sequence LCR1901_VH_1G10m_03 (K) (SEQ ID NO:19), wherein said variants retain TGF-β3 reactivity and neutralization; or (c) LCR1901_VH_1G10m_02 (J) (SEQ ID NO:36) or variants thereof having at least 90% amino acid identity to the sequence LCR1901_VH_1G10m_02 (J) (SEQ ID NO:36), wherein said variants retain TGF-β3 reactivity and neutralization;

and the light chain variable region sequence:

(d) LCR1901_VK_GLv1_03 (F) (SEQ ID NO:22) or variants thereof having at least 90% amino acid identity to the sequence LCR1901_VK_GLv1_03 (F) (SEQ ID NO:22), wherein said variants retain TGF-β3 reactivity and neutralization; or (e) LCR1901_VK_GLv1_05 (H) (SEQ ID NO:23) or variants thereof having at least 90% amino acid identity to the sequence LCR1901_VK_GLv1_05 (H) (SEQ ID NO:23), wherein said variants retain TGF-β3 reactivity and neutralization.

2. The isolated antibody of claim 1 which is selected from:

(a) antibody 1901-1C comprising the heavy chain sequence of LCR1901_VH_1G10m (SEQ ID NO:18), and light chain sequence LCR1901_VK_GLv1_03 (F) (SEQ ID NO:22);

(b) antibody 1901-1A comprising the heavy chain sequence of LCR1901_VH_1G10m (SEQ ID NO:18), and light chain sequence LCR1901_VK_GLv1_05 (H) (SEQ ID NO:23);

(c) antibody 1901-1D comprising the heavy chain sequence of LCR1901_VH_1G10m_03 (K) (SEQ ID NO: 19), and light chain sequence LCR1901_VK_GLv1_03 (F) (SEQ ID NO:22); and (d) antibody 1901-1B comprising the heavy chain sequence of LCR1901_VH_1G10m_03 (K) (SEQ ID NO: 19), and light chain sequence LCR1901_VK_GLv1_05 (H) (SEQ ID NO:23).

3. The isolated antibody or fragment of claim 1 which is a humanized or chimeric antibody or fragment thereof.

4. The isolated antibody or fragment of claim 1 which is an antibody or fragment thereof wherein said isolated antibody is the form of an antibody F(ab')2, scFv fragment, domain antibody, minibody, diabody, triabody or tetrabody.

5. The isolated antibody or fragment of claim 1 further comprising a detectable or functional label.

6. The isolated antibody or fragment of claim 5, wherein said detectable or functional label is a covalently attached drug or a radiolabel.

7. An isolated nucleic acid which comprises a sequence encoding an antibody or fragment of claim 1.

8. A method of preparing an antibody or fragment as defined in claim 1 which comprises expressing the nucleic acid of claim 7 under conditions to bring about expression of said antibody or fragment, and recovering the antibody or fragment.

9. A pharmaceutical composition comprising an antibody or fragment as defined in claim 1 and a pharmaceutically acceptable vehicle, carrier or diluent.

10. An immunological composition comprising an antibody or fragment as defined in claim 1 and a pharmaceutically acceptable vehicle, carrier or diluent, optionally comprising an adjuvant and/or one or more antigen, an immunoregulatory antibody, or a small molecule inhibitor to an immune modulator.

* * * * *